US008288430B2

(12) United States Patent
Zemolka et al.

(10) Patent No.: US 8,288,430 B2
(45) Date of Patent: Oct. 16, 2012

(54) SPIRO(5.5)UNDECANE DERIVATIVES

(75) Inventors: Saskia Zemolka, Aachen (DE); Stefan Schunk, Aachen (DE); Klaus Linz, Wachtberg (DE); Wolfgang Schröder, Aachen (DE); Werner Englberger, Stolberg (DE); Fritz Theil, Berlin (DE); Birgit Roloff, Berlin (DE)

(73) Assignee: Grunenthal GmbH, Aachen (DE)

( * ) Notice: Subject to any disclaimer, the term of this patent is extended or adjusted under 35 U.S.C. 154(b) by 537 days.

(21) Appl. No.: 12/410,605

(22) Filed: Mar. 25, 2009

(65) Prior Publication Data
US 2009/0247505 A1 Oct. 1, 2009

(30) Foreign Application Priority Data

Mar. 27, 2008 (EP) .................... 08005804

(51) Int. Cl.
*A61K 31/403* (2006.01)
*C07D 209/02* (2006.01)
*C07D 209/96* (2006.01)
(52) U.S. Cl. .................... 514/409; 514/411; 548/411
(58) Field of Classification Search .................. 548/411; 514/409, 411
See application file for complete search history.

(56) References Cited

U.S. PATENT DOCUMENTS

| 3,328,412 | A | 6/1967 | Atkinson et al. |
| 4,065,573 | A | 12/1977 | Lednicer |
| 4,115,589 | A | 9/1978 | Lednicer |
| 4,291,039 | A | 9/1981 | Van Dyke, Jr. et al. |
| 4,366,172 | A | 12/1982 | Lednicer |
| 4,575,508 | A | 3/1986 | Steiner et al. |
| 5,328,905 | A | 7/1994 | Hamminga et al. |
| 5,631,265 | A | 5/1997 | Audia et al. |
| 5,760,051 | A | 6/1998 | Audia et al. |
| 5,869,691 | A | 2/1999 | Audia et al. |
| 6,998,409 | B2 | 2/2006 | Sundermann et al. |
| 7,276,518 | B2 | 10/2007 | Sundermann et al. |
| 7,332,519 | B2 | 2/2008 | Hinze et al. |
| 7,485,634 | B2 | 2/2009 | Martin et al. |
| 7,507,758 | B2 | 3/2009 | Sundermann et al. |
| 7,547,707 | B2 | 6/2009 | Hinze et al. |
| 7,595,311 | B2 | 9/2009 | Busch et al. |
| 7,799,931 | B2 | 9/2010 | Hinze et al. |
| 7,960,404 | B2 | 6/2011 | Schunk et al. |
| 7,977,370 | B2 | 7/2011 | Zemolka et al. |
| 8,053,576 | B2 | 11/2011 | Hinze et al. |
| 8,133,992 | B2 | 3/2012 | Martin et al. |
| 8,143,257 | B2 | 3/2012 | Choi et al. |
| 2003/0236250 | A1 | 12/2003 | Pineiro et al. |
| 2004/0023947 | A1 | 2/2004 | Martin et al. |
| 2005/0192333 | A1 | 9/2005 | Hinze et al. |
| 2005/0267107 | A1 | 12/2005 | Sundermann et al. |
| 2006/0004034 | A1 | 1/2006 | Hinze et al. |
| 2006/0235012 | A1 | 10/2006 | Davidson et al. |
| 2007/0149557 | A1 | 6/2007 | Collins et al. |
| 2008/0125475 | A1 | 5/2008 | Linz et al. |
| 2008/0221141 | A1 | 9/2008 | Friderichs et al. |
| 2008/0261956 | A1 | 10/2008 | Choi et al. |
| 2008/0280942 | A1 | 11/2008 | Diaz-Fernandez et al. |
| 2009/0042866 | A1 | 2/2009 | Lennox et al. |
| 2009/0156626 | A1 | 6/2009 | Hinze et al. |
| 2009/0163716 | A1 | 6/2009 | Hinze et al. |
| 2009/0247505 | A1 | 10/2009 | Zemolka et al. |
| 2009/0247530 | A1 | 10/2009 | Nolte et al. |
| 2009/0247561 | A1 | 10/2009 | Zemolka et al. |
| 2009/0247573 | A1 | 10/2009 | Zemolka et al. |
| 2009/0247591 | A1 | 10/2009 | Zemolka et al. |
| 2009/0326218 | A1 | 12/2009 | Martin et al. |
| 2010/0009986 | A1 | 1/2010 | Zemolka et al. |
| 2010/0048553 | A1 | 2/2010 | Schunk et al. |
| 2010/0048554 | A1 | 2/2010 | Schunk et al. |
| 2010/0173824 | A1 | 7/2010 | Busch et al. |
| 2011/0015220 | A1 | 1/2011 | Linz et al. |
| 2011/0059999 | A1 | 3/2011 | Frormann et al. |

FOREIGN PATENT DOCUMENTS

| AR | 071066 | | 5/2010 |
| AR | 071067 | | 5/2010 |
| AR | 071068 | | 5/2010 |
| AR | 073841 | | 12/2010 |
| AU | 2009228637 | | 10/2009 |
| AU | 2009228642 | | 10/2009 |
| AU | 2009228643 | | 10/2009 |
| AU | 2009228645 | | 10/2009 |
| AU | 2009228647 | | 10/2009 |
| AU | 2009228648 | | 10/2009 |
| CA | 2446461 | A1 | 11/2002 |
| CA | 2550868 | A1 | 7/2005 |
| CA | 2658376 | A1 | 1/2008 |
| CA | 2658379 | A1 | 1/2008 |
| CA | 2718209 | | 10/2009 |
| CA | 2718209 | A1 | 10/2009 |
| CA | 2719735 | | 10/2009 |
| CA | 2719736 | | 10/2009 |
| CA | 2719739 | | 10/2009 |

(Continued)

OTHER PUBLICATIONS

Dorwald F. A. Side Reactions in Organic Synthesis, 2005, Wiley: VCH, Weinheim p. IX of Preface.*
Maddox et al, J. Med. Chem., 1965, 8, pp. 230-235.
Elliott et al., Bioorg. Ned. Chem. Lett., EN: 16; pp. 2006-2929.
Jirkovsky et al.; J. Hetrocycl. Chem. 12, 1975, pp. 937-940.
Beck et al.; J. Chem. Soc. Perkin 1, 1992, pp. 813-822.
Shinada et al., Tetrahedron Letters, 39, 1996, pp. 7099-7102.
Garden et al., Tetrahedron, 58, 2002, pp. 8399-8412.
Katritzky et al.; Synthesis 1989, pp. 66-69.
Bandini et al., J. Org. Chem., 67, 15, 2002; pp. 5386-5389.
Davis et al., J. Med. Chem., 35, 1, 1992, pp. 177-184.
Yamagishi et al., J. Med. Chem. 35, 11, 1992, pp. 2085-2094.
Gleave et al., Bioorg. Med. Chem. Lett., 8, 10, 1998, pp. 1231-1236.
Sandmeyer, Helv. Chim. Acta; 2, 1919; pp. 239.
Katz et al., J. Med. Chem. 31, 6, 1988; pp. 1244-1250.

(Continued)

*Primary Examiner* — Rita Desai
(74) *Attorney, Agent, or Firm* — Norris McLaughlin & Marcus, PA

(57) ABSTRACT

The invention relates to compounds that have an affinity to the μ-opioid receptor and the ORL 1-receptor, methods for their production, medications containing these compounds and the use of these compounds for the treatment of pain and other conditions.

7 Claims, No Drawings

FOREIGN PATENT DOCUMENTS

| | | |
|---|---|---|
| CA | 2719742 | 10/2009 |
| CA | 2719743 | 10/2009 |
| CA | 2446461 C | 4/2011 |
| DE | 28 39 891 | 4/1979 |
| DE | 28 39 891 A1 | 4/1979 |
| EP | 2260022 | 10/2009 |
| EP | 2257526 | 12/2010 |
| EP | 2260021 | 12/2010 |
| EP | 2260042 | 12/2010 |
| EP | 2271613 | 1/2011 |
| EP | 2280941 | 2/2011 |
| GB | 1 055 203 | 1/1967 |
| KR | 20100132048 | 12/2010 |
| KR | 20100136521 | 12/2010 |
| MX | 2010009955 | 9/2010 |
| MX | 2010010337 | 10/2010 |
| MX | 2010010339 | 10/2010 |
| MX | 2010010407 | 10/2010 |
| MX | 2010010446 | 11/2010 |
| MX | 2010010448 | 11/2010 |
| PE | 16502009 | 11/2009 |
| PE | 16572009 | 11/2009 |
| PE | 18222009 | 12/2009 |
| PE | 18232009 | 12/2009 |
| PE | 16892009 | 11/2011 |
| WO | 01 87838 | 11/2001 |
| WO | 02 90330 | 5/2002 |
| WO | 02 090317 | 11/2002 |
| WO | 02090317 A1 | 11/2002 |
| WO | 03 008370 | 1/2003 |
| WO | 03 008731 | 1/2003 |
| WO | 03 080557 | 1/2003 |
| WO | 2004 043899 | 5/2004 |
| WO | 2004 043900 | 5/2004 |
| WO | 2004 043902 | 5/2004 |
| WO | 2004 043909 | 5/2004 |
| WO | 2004 043949 | 5/2004 |
| WO | 2004 043967 | 5/2004 |
| WO | 2005 063769 | 7/2005 |
| WO | 2005 066183 | 7/2005 |
| WO | 2005 110970 | 11/2005 |
| WO | 2005 110971 | 11/2005 |
| WO | 2005 110973 | 11/2005 |
| WO | 2005 110974 | 11/2005 |
| WO | 2005 110975 | 11/2005 |
| WO | 2005 110976 | 11/2005 |
| WO | 2005 110977 | 11/2005 |
| WO | 2006 018184 | 2/2006 |
| WO | 2006058088 | 6/2006 |
| WO | 2006065479 | 6/2006 |
| WO | 2006065480 | 6/2006 |
| WO | 2006 108565 | 10/2006 |
| WO | 2007 079927 | 7/2007 |
| WO | 2007 079928 | 7/2007 |
| WO | 2007 079930 | 7/2007 |
| WO | 2007 079931 | 7/2007 |
| WO | 2007079931 A1 | 7/2007 |
| WO | 2007 124903 | 11/2007 |
| WO | 2007 124930 | 11/2007 |
| WO | 2008 009415 | 1/2008 |
| WO | 2008 009416 | 1/2008 |
| WO | 2008040481 A1 | 4/2008 |
| WO | 2008101659 A1 | 8/2008 |
| WO | 2008101660 A1 | 8/2008 |
| WO | 2009 118169 | 3/2009 |
| WO | 2009090317 | 7/2009 |
| WO | 2009118163 | 10/2009 |
| WO | 2009118163 A1 | 10/2009 |
| WO | 2009118168 | 10/2009 |
| WO | 2009118168 A1 | 10/2009 |
| WO | 2009118171 | 10/2009 |
| WO | 2009118171 A1 | 10/2009 |
| WO | 2009118173 | 10/2009 |
| WO | 2009118173 A1 | 10/2009 |
| WO | 2009118174 | 10/2009 |

OTHER PUBLICATIONS

Bac et al., Tetrahedron Letters, vol. 29, No. 23, 1988, pp. 2819-2822.
Ma et al., J. Org. Chem. 66, 2001, pp. 4525-4542.
Kato et al., J. Fluorine Chem. 99, 1, 1999; pp. 5-8.
Corey et al.; Tetrahedron Letters, No. 36, 1972, pp. 3769-3772.
Harned et al.; Tetrahedron, No. 61, 2005, pp. 12093-12099.
Katritzky et al., Synthesis, Dec. 1992, pp. 1295-1298.
Kudzma et al., J. Med. Chem. No. 32, 1989, pp. 2534-2542.
Layer, B.F. Goodrich Co., Research Center, Dec. 7, 1962, pp. 489-510.
Bavetsias et al., J. Med. Chjem., No. 43, 2000, pp. 1910-1926.
Prashad et al., Tetahedron LEtters, No. 46, 2005, pp. 5455-5458.
Regitz et al.; Chem. Ber., No. 101, 1968, pp. 3734-3743.
Shiner et al., J. am. Chem. Soc., 103, 1981, pp. 436-442.
Xia et al., Organic Letters, vol. 7, No. 7, 2005, pp. 1315-1318.
Messina et al., Tetrahedron, Asymmetry 11, 2000, pp. 1681-1685.
Greene et al., Protective Groups in Organic Synthesis; Wiley Interscience Publication; 3rd Edition, 1999.
Williams et al., J. Org. Chem., 45, 1980, pp. 5082-5088.
Piper et al., Journal of Medicinal Chemistry, US American Chemical Society, Washington, No. 9, Jan. 1, 1966; pp. 911-920.
Gilbert, et al., Journal of American Chemical Society, No. 72, 1950, pp. 2411-2417.
Chu et al., Tetrahedron, Elsevier Science Publishers, Amsterdam, NL, No. 62, 2006, pp. 5536-5548.
Catterall et al., The Journal of Biological Chemistry, vol. 256, No. 17, Sep. 1981, pp. 8922-8927.
Dirat et al., Tetrahedron Letters, No. 47, 2006, pp. 1295-1298.
Hamzé et al., J. Org. Chem., No. 68, 2003, pp. 7316-7321.
Hashmi et al., Organic Letters, vol. 6, No. 23, 2004, pp. 4391-4394.
Morwick et al., Organic Letters, vol. 4, No. 16, 2002, pp. 2665-2668.
Thompson et al., Journal of Medical Chemistry, vol. 41, No. 21, 1998, pp. 3923-3927.
D'Amour et al., "A Method for Determining Loss of Pain Sensation", The Biologic Research Laboratory, pp. 74-79, Jan. 27, 1941.
Finlayson et al., "[3H]Dofetilide Binding in SHSY5Y and HEK293 Cells Expressing a HERG-like K+ Channel?", European Journal of Pharmacology, vol. 412, pp. 203-212, (2001).
Kim et al., "An Experimental Model for Peripheral Neuropathy Produced by Segmental Spinal Nerve Ligation in the Rat", Elsevier Science Publishers B.V., No. 50, pp. 355-363, (1992).
Lednicer et al., "4-Amino-4-arylcyclohexanones and Their Derivatives, a Novel Class of Analgesics. 1. Modification of the Aryl Ring", The Upjohn Company, Research Laboratories, Aug. 7, 1979.
Gaspar et al. Mild Cobalt-Catalyzed Hydrocyanation of Olefins with Tosyl Cyanide. Angew. Chemie. Int. Ed. 2007, vol. 46, pp. 4519-4522.
Lednicer et al., J. Med. Chem., 23, 1980, 424-430.
Lee, et al., Bull. Korean Chem. Soc. 25, 2004, 207-212.
Jenck, et al, "Orphanin FQ acts as an anxiolytic to attenuate behavioral responses to stress"; Proc. Natl. Acad. Sci. USA, vol. 94, Dec. 1997, pp. 14854-14858.
King et al, "Spinal analgesic activity of orphanin FQ/nociceptin and its fragments", Neuroscience Letters 223 (1997), pp. 113-116.
Meunier, et al, "Isolation and structure of the endogenous agonist of opioid receptor-like ORL1 receptor", Nature, vol. 377, Oct. 12, 1995, pp. 532-535.
Mogil, et al, "Orphanin FQ is a Functional Anti-Opioid Peptide"; Neuroscience, vol. 75, No. 2, 1996, pp. 333-337.
Reinscheid, et al, "Orphanin FQ: A Neuropepetide that Activates an Opioidlike G Protein-Coupled Receptor", Science, vol. 270, Nov. 3, 1995, pp. 792-794.
Rose et al, Can J. Chem., 74, 1996, 1836-1844.
Abdulla et al, "Axotomy Reduces the Effect of Analgesic Opioids Yet Increases the Effect of Nociceptin on Dorsal Root Ganglion Neurons"; The Journal of Nocisciene, Dec. 1, 1998, 18 (23), pp. 9685-9694.
Manabe et al, "Facilitation of long-term potentiation and memory in mice lacking nociceptin receptors"; Nature, vol. 394, Aug. 6, 1998, pp. 577-581.

Nishi et al, "Unrestrained nociceptive response and disregulation of hearing ability in mice lacking the nociceptin/orphaninFQ receptor"; The EMBO Journal, vol. 16, No. 8, 1997, pp. 1858-1864.

Calo, et al, "Pharmacology of nociceptin and its receptor: a novel therapeutic target"; British Journal of Pharmacology (2000) 129, pp. 1261-1283.

Patani et al Chem rev. 1996, vol. 96, p. 3147-3176.

Ardati, Mol. Pharmacol., 51, 1997, pp. 816-824.

* cited by examiner

SPIRO(5.5)UNDECANE DERIVATIVES

The invention relates to substituted spirocyclic cyclohexane derivatives that have an affinity to the μ-opioid receptor and the ORL 1-receptor, methods for their production, medications containing these compounds and the use of these compounds for the production of medications.

Spirocyclic cyclohexane derivatives that have an affinity to the μ-opioid receptor and the ORL 1-receptor are known in the prior art. In this context, reference can be made, for example, to the following documents in their full scope WO2004/043967, WO2005/063769, WO2005/066183, WO2006/018184, WO2006/108565, WO2007/124903 and WO2008/009416.

However, the known compounds are not satisfactory in every respect and there is a need for further compounds with comparable or better properties.

Thus, in appropriate binding assays the known compounds occasionally exhibit a certain affinity to the hERG ion channel, the L-type calcium ion channel (phenylalkylamine, benzothiazepine, dihydropyridine binding sites) or to the sodium channel in the BTX assay (batrachotoxin), which can be respectively interpreted as an indication of cardiovascular side-effects. Moreover, many of the known compounds exhibit only a slight solubility in aqueous media, which can adversely affect the bioavailability, inter alia. In addition, the chemical stability of the known compounds is often merely inadequate. Thus, the compounds occasionally do not exhibit an adequate pH, UV or oxidation stability, which can adversely affect the storage stability and also the oral bioavailability, inter alia. Moreover, the known compounds have an unfavourable PK/PD (pharmacokinetic/pharmacodynamic) profile in some instances, which can be displayed, for example, in too long a duration of effect.

The metabolic stability of the known compounds also appears to be in need of improvement. An improved metabolic stability can point to an increased bioavailability. A weak or absent interaction with transporter molecules that participate in the absorption and excretion of medicinal substances should be considered an indication of an improved bioavailability and possibly low interactions of medications. Moreover, the interactions with the enzymes involved in the breakdown and excretion of medicinal substances should also be as low as possible, since such test results also indicate that low interactions of medications or none at all are possibly to be expected.

Moreover, the known compounds at times exhibit an only low selectivity with respect to the kappa-opioid receptor, which is responsible for side-effects such as e.g. dysphoria, sedation and diuresis.

The object forming the basis of the invention is to provide compounds that are suitable for pharmaceutical purposes and have advantages over the compounds of the prior art.

This object is achieved by the compounds described hereinbelow.

It has been surprisingly found that substituted derivatives can be produced that have an affinity to the μ-opioid receptor and the ORL 1-receptor.

The invention relates to compounds of the general formula (1)

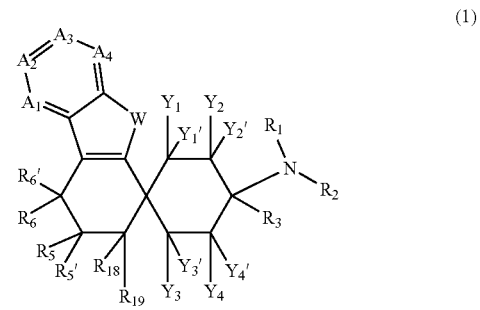

wherein
$A_1$ stands for —N= or —$CR_7$=,
$A_2$ stands for —N= or —$CR_8$=,
$A_3$ stands for —N= or —$CR_9$=,
$A_4$ stands for —N= or —$CR_{10}$=;
on condition that at most two of the residues $A_1$, $A_2$, $A_3$ and $A_4$, preferably 0, 1 or 2 of the residues $A_1$, $A_2$, $A_3$ and $A_4$, stand for —N=;
$Y_1$, $Y_1'$, $Y_2$, $Y_2'$, $Y_3$, $Y_3'$, $Y_4$ and $Y_4'$ are respectively selected independently of one another from the group comprising —H, —F, —Cl, —Br, —I, —CN, —$NO_2$, —CHO, —$R_0$, —C(=O)$R_0$, —C(=O)H, —C(=O)—OH, —C(=O)$OR_0$, —C(=O)$NH_2$, —C(=O)$NHR_0$, —C(=O)$N(R_0)_2$, —OH, —$OR_0$, —OC(=O)H, —OC(=O)$R_0$, —OC(=O)$OR_0$, —OC(=O)$NHR_0$, —OC(=O)$N(R_0)_2$, —SH, —$SR_0$, —$SO_3H$, —S(=O)$_{1-2}$—$R_0$, —S(=O)$_{1-2}$$NH_2$, —$NH_2$, —$NHR_0$, —$N(R_0)_2$, —$N^+(R_0)_3$, —$N^+(R_0)_2O^-$, —NHC(=O)$R_0$, —NHC(=O)$OR_0$, —NHC(=O)$NH_2$, —NHC(=O)$NHR_0$ and —NHC(=O)$N(R_0)_2$; preferably are respectively selected independently of one another from the group comprising —H, —F, —Cl, —CN and —$C_{1-8}$-aliphatic; or $Y_1$ and $Y_1'$, or $Y_2$ and $Y_2'$, or $Y_3$ and $Y_3'$, or $Y_4$ and $Y_4'$ jointly stand for =O;
W stands for —N—, —O— or —S—, preferably for $NR_4$ or —O—;
$R_0$ respectively independently stands for —$C_{1-8}$-aliphatic, —$C_{3-12}$-cycloaliphatic, -aryl, -heteroaryl, —$C_{1-8}$-aliphatic-$C_{3-12}$-cycloaliphatic, —$C_{1-8}$-aliphatic-aryl, —$C_{1-8}$-aliphatic-heteroaryl, —$C_{3-8}$-cycloaliphatic-$C_{1-8}$-aliphatic, —$C_{3-8}$-cycloaliphatic-aryl or —$C_{3-8}$-cycloaliphatic-heteroaryl;
$R_1$ and $R_2$, independently of one another, stand for —H or —$R_0$; or $R_1$ and $R_2$ together stand for —$CH_2CH_2OCH_2CH_2$—, —$CH_2CH_2NR_{11}CH_2CH_2$— or —$(CH_2)_{3-6}$—;
$R_3$ stands for —$R_0$;
$R_4$ stands for —H, —$R_0$, —$COR_{12}$ or —S(=O)$_2R_{12}$;
$R_5$, $R_5'$, $R_6$, $R_6'$, $R_7$, $R_8$, $R_9$, $R_{10}$, $R_{18}$ and $R_{19}$ respectively independently of one another stand for —H, —F, —Cl, —Br, —I, —$NO_2$, —$CF_3$, —$OR_{13}$, —$SR_{13}$, —S(=O)$_2R_{13}$, —S(=O)$_2OR_{13}$, —S(=O)$_2NR_{14}R_{15}$, —CN, —C(=O)$OR_{13}$, —C(=O)$NR_{13}$, —C(=O)$NR_0OR_0$, —$NR_{14}R_{15}$, —NHC(=O)$R_0$, —NHC(=O)$NHR_0$, —NHC(=O)$N(R_0)_2$, —NHC(=O)$OR_0$, —NHS(=O)$_{1-2}R_0$, =O or —$R_0$; or $R_5$ and $R_6$ jointly stand for —(CH$_2$)$_{2-6}$—, wherein individual hydrogen atoms can also be replaced by —F, —Cl, —Br, —I, —$NO_2$, —$CF_3$, —$OR_{13}$, —CN or —$C_{1-6}$-aliphatic;
$R_{11}$ respectively independently stands for —H, —$R_0$ or —C(=O)$R_0$;
$R_{12}$ respectively independently stands for —H, —$R_0$, —$OR_{13}$, or —$NR_{14}R_{15}$;
$R_{13}$ respectively independently stands for —H or —$R_0$;

$R_{14}$ and $R_{15}$ independently of one another stand for —H or —$R_0$; or $R_{14}$ and $R_{15}$ together stand for —$CH_2CH_2OCH_2CH_2$—, —$CH_2CH_2NR_{16}CH_2CH_2$— or —$(CH_2)_{3-6}$—;

$R_{16}$ stands for —H or —$C_{1-6}$-aliphatic;

wherein

"aliphatic" respectively is a branched or unbranched, saturated or a mono- or polyunsaturated, unsubstituted or mono- or polysubstituted, aliphatic hydrocarbon residue;

"cycloaliphatic" respectively is a saturated or a mono- or polyunsaturated, unsubstituted or mono- or polysubstituted, alicyclic, mono- or multicyclic hydrocarbon residue, the number of ring-carbon atoms of which preferably lies in the specified range (i.e. "$C_{3-8}$-cycloaliphatic" preferably has 3, 4, 5, 6, 7 or 8 ring-carbon atoms);

wherein with respect to "aliphatic" and "cycloaliphatic", "mono- or polysubstituted" is understood to mean the mono- or polysubstitution, e.g. the mono-, di-, tri- or complete substitution, of one or more hydrogen atoms by substituents selected independently of one another from the group comprising —F, —Cl, —Br, —I, —CN, —$NO_2$, —CHO, =O, —$R_0$, —C(=O)$R_0$, —C(=O)H, —C(=O)OH, —C(=O)O$R_0$, —C(=O)$NH_2$, —C(=O)$NHR_0$, —C(=O)N($R_0$)$_2$, —OH, —O$R_0$, —OC(=O)H, —OC(=O)$R_0$, —OC(=O)O$R_0$, —OC(=O)$NHR_0$, —OC(=O)N($R_0$)$_2$, —SH, —S$R_0$, —$SO_3H$, —S(=O)$_{1-2}$—$R_0$, —S(=O)$_{1-2}$$NH_2$, —$NH_2$, —$NHR_0$, —N($R_0$)$_2$, —$N^+$($R_0$)$_3$, —$N^+$($R_0$)$_2$$O^-$, —NHC(=O)$R_0$, —NHC(=O)O$R_0$, —NHC(=O)$NH_2$, —NHC(=O)$NHR_0$, —NHC(=O)N($R_0$)$_2$, —Si($R_0$)$_3$, —PO(O$R_0$)$_2$;

"aryl", respectively independently, stands for a carbocyclic ring system with at least one aromatic ring, but without heteroatoms in this ring, wherein, if necessary, the aryl residues can be condensed with further saturated, (partially) unsaturated or aromatic ring systems, and each aryl residue can be present in unsubstituted or mono- or polysubstituted form, wherein the aryl substituents can be the same or different and in any desired and possible position of the aryl;

"heteroaryl" stands for a 5-, 6- or 7-membered cyclic aromatic residue, which contains 1, 2, 3, 4 or 5 heteroatoms, wherein the heteroatoms, the same or different, are nitrogen, oxygen or sulphur, and the heterocycle can be unsubstituted or mono- or polysubstituted; wherein in the case of the substitution on the heterocycle the substituents can be the same or different and can be in any desired and possible position of the heteroaryl; and wherein the heterocycle can also be part of a bi- or polycyclic system;

wherein with respect to "aryl" and "heteroaryl", "mono- or polysubstituted" is understood to mean the mono- or polysubstitution of one or more hydrogen atoms of the ring system by substituents selected from the group comprising —F, —Cl, —Br, —I, —CN, —$NO_2$, —CHO, =O, —$R_0$, —C(=O)$R_0$, —C(=O)H, —C(=O)OH, —C(=O)O$R_0$, —C(=O)$NH_2$, —C(=O)$NHR_0$, —C(=O)—N($R_0$)$_2$, —OH, —O(CH$_2$)$_{1-2}$O—, —O$R_0$, —OC(=O)H, —OC(=O)$R_0$, —OC(=O)O$R_0$, —OC(=O)$NHR_0$, —OC(=O)N($R_0$)$_2$, —SH, —S$R_0$, —$SO_3H$, —S(=O)$_{1-2}$—$R_0$, —S(=O)$_{1-2}$$NH_2$, —$NH_2$, —$NHR_0$, —N($R_0$)$_2$, —$N^+$($R_0$)$_3$, —$N^+$($R_0$)$_2$$O$—, —NHC(=O)$R_0$, —NHC(=O)O$R_0$, —NH—C(=O)$NH_2$, —NHC(=O)$NHR_0$, —NHC(=O)—N($R_0$)$_2$, —Si($R_0$)$_3$, —PO(O$R_0$)$_2$; wherein any N-ring atoms present can be respectively oxidised (N-oxide);

in the form of a single stereoisomer or mixture thereof, the free compounds and/or their physiologically compatible salts.

In the combination of different residues, e.g. $R_0$, $R_7$, $R_8$, $R_9$ and $R_{10}$, and also the combination of residues at substituents thereof such as e.g. —O$R_{13}$, —S$R_{13}$, —$SO_2R_{13}$ or —COO$R_{13}$, a substituent, e.g. $R_{13}$, can assume different meanings within a substance for two or more residues, e.g. $R_0$, $R_7$, $R_8$, $R_9$ and $R_{10}$.

The compounds according to the invention exhibit favourable binding to the ORL 1-receptor and the μ-opioid receptor.

In a preferred embodiment, the compounds according to the invention have an affinity ratio of ORL1/μ of at least 0.1. The ORL1/μ ratio is defined as $1/[K_{i(ORL1)}/K_{i(\mu)}]$. It is particularly preferred if the ORL1/μ ratio amounts to at least 0.2 or at least 0.5, more preferred at least 1.0 or at least 2.0, further preferred at least 3.0 or at least 4.0, most preferred at least 5.0 or at least 7.5 and in particular at least 10 or at least 15. In a preferred embodiment the ORL1/μ ratio lies in the range of 0.1 to 30, more preferred 0.1 to 25.

In another preferred embodiment, the compounds according to the invention have an ORL1/μ affinity ratio of more than 30, more preferred at least 50, further preferred at least 100, most preferred at least 200 and in particular at least 300.

The compounds according to the invention preferably have a $K_i$ value on the μ-opioid receptor of at maximum 500 nM, more preferred at maximum 100 nM, further preferred at maximum 50 nM, most preferred at maximum 10 nM and in particular at maximum 1.0 nM.

Methods for determining the $K_i$ value on the μ-opioid receptor are known to the person skilled in the art. The determination is preferably conducted as described in association with the examples.

It has surprisingly been shown that compounds with affinity to the ORL 1- and μ-opioid receptor, in which the ratio of ORL 1 to μ defined by $1/[K_{i(ORL1)}/K_{i(\mu)}]$ lies in the range of 0.1 to 30, preferably 0.1 to 25, have a pharmacological profile that has significant advantages compared to the other opioid receptor ligand:

1. The compounds according to the invention exhibit an efficacy in acute pain models that is at times comparable with the usual stage-3 opioids. However, they are distinguished at the same time by a significantly better compatibility compared to classic μ-opioids.
2. In contrast to common stage-3 opioids, the compounds according to the invention exhibit a significantly higher efficacy in mono- and polyneuropathic pain models, which is attributable to a synergy of ORL 1- and μ-opioid components.
3. In contrast to common stage-3 opioids, the compounds according to the invention exhibit in neuropathic animals a substantial, preferably a complete, separation of antiallodynic or antihyperalgesic effect and antinociceptive effect.
4. In contrast to common stage-3 opioids, in animal models the compounds according to the invention exhibit a significant increase in efficacy for chronic inflammatory pain (carageenan- or CFA-induced hyperalgesia, visceral inflammatory pain, amongst others) compared to acute pain.
5. In contrast to common stage-3 opioids, side-effects typical of μ-opioids (respiratory depression, opioid-induced hyperalgesia, physical dependence/withdrawal, psychic dependence/addiction, among others) are significantly reduced or preferably not observed with the compounds according to the invention in the therapeutically effective dose range.

In view of the reduced μ-opioid side-effects, on the one hand, and the increased efficacy in chronic, preferably neuropathic pain, on the other hand, the mixed ORL 1/μ agonists are thus distinguished by significantly increased safety margins compared to pure μ-opioids. This results in a significantly increased "therapeutic window" in the treatment of pain conditions, preferably chronic pain, more preferred neuropathic pain.

In a preferred embodiment of the compounds according to the invention $A_1$, $A_2$, $A_3$ and $A_4$ differ from —N=. In another preferred embodiment of the compounds according to the invention three of the residues $A_1$, $A_2$, $A_3$ and $A_4$ differ from —N= and the remaining residue is the same as —N=. Preferably $A_1$, $A_2$ and $A_3$ differ from —N=; or $A_1$, $A_2$, and $A_4$ differ from —N=; or $A_1$, $A_3$, and $A_4$ differ from —N=; or $A_2$, $A_3$ and $A_4$ differ from —N=. In another preferred embodiment of the compounds according to the invention two of the residues $A_1$, $A_2$, $A_3$ and $A_4$ differ from —N= and the other two residues are —N=. Preferably, $A_1$ and $A_2$ are —N= and $A_3$ and $A_4$ differ from —N=; or $A_2$ and $A_3$ are —N= and $A_1$ and $A_4$ differ from —N=; $A_3$ and $A_4$ are —N= and $A_1$ and $A_2$ differ from —N=; or $A_1$ and $A_3$ are —N= and $A_2$ and $A_4$ differ from —N=; or $A_1$ and $A_4$ are —N= and $A_2$ and $A_3$ differ from —N=; or $A_2$ and $A_4$ are —N= and $A_1$ and $A_3$ differ from —N=.

Preferably, $Y_1$, $Y_1'$, $Y_2$, $Y_2'$, $Y_3$, $Y_3'$, $Y_4$ and $Y_4'$ are respectively selected independently of one another from the group comprising —H, —F, —Cl, —Br, —I, —CN, —NH$_2$, —NH—C$_{1-6}$-aliphatic, —NH—C$_{3-8}$-cycloaliphatic, —NH—C$_{1-6}$-aliphatic-OH, —N(C$_{1-6}$-aliphatic)$_2$, —N(C$_{3-8}$-cycloaliphatic)$_2$, —N(C$_{1-6}$-aliphatic-OH)$_2$, —NO$_2$, —NH—C$_{1-6}$-aliphatic-C$_{3-8}$-cycloaliphatic, —NH—C$_{1-6}$-aliphatic-aryl, —NH—C$_{1-6}$-aliphatic-heteroaryl, —NH-aryl, —NH-heteroaryl, —SH, —S—C$_{1-6}$-aliphatic, —S—C$_{3-8}$-cycloaliphatic, —S—C$_{1-6}$-aliphatic-C$_{3-8}$-cycloaliphatic, —S—C$_{1-6}$-aliphatic-aryl, —S—C$_{1-6}$-aliphatic-heteroaryl, —S-aryl, —S-heteroaryl, —OH, —O—C$_{1-6}$-aliphatic, —O—C$_{3-8}$-cycloaliphatic, —O—C$_{1-6}$-aliphatic-OH, —O—C$_{1-6}$-aliphatic-C$_{3-8}$-cycloaliphatic, —O—C$_{1-6}$-aliphatic-aryl, —O—C$_{1-6}$-aliphatic-heteroaryl, —O-aryl, —O-heteroaryl, —O—C(=O)C$_{1-6}$-aliphatic, —O—C(=O)C$_{3-8}$-cycloaliphatic, —O—C(=O)C$_{1-6}$-aliphatic-OH, —O—C(=O)C$_{1-6}$-aliphatic-C$_{3-8}$-cycloaliphatic, —O—C(=O)C$_{1-6}$-aliphatic-aryl, —O—C(=O)C$_{1-6}$-aliphatic-heteroaryl, —O—C(=O)aryl, —O—C(=O)heteroaryl, —C$_{1-6}$-aliphatic, —C$_{3-8}$-cycloaliphatic, —C$_{1-6}$-aliphatic-C$_{3-8}$-cycloaliphatic, —C$_{1-6}$-aliphatic-aryl, —C$_{1-6}$-aliphatic-heteroaryl, -aryl, -heteroaryl, —C(=O)C$_{1-6}$-aliphatic, —C(=O)C$_{3-8}$-cycloaliphatic, —C(=O)C$_{1-6}$-aliphatic-C$_{3-8}$-cycloaliphatic, —C(=O)C$_{1-6}$-aliphatic-aryl, —C(=O)C$_{1-6}$-aliphatic-heteroaryl, —C(=O)aryl, —C(=O)heteroaryl, —CO$_2$H, —CO$_2$—C$_{1-6}$-aliphatic, —CO$_2$—C$_{3-8}$-cycloaliphatic, —CO$_2$—C$_{1-6}$-aliphatic-C$_{3-8}$-cycloaliphatic, —CO$_2$—C$_{1-6}$-aliphatic-aryl, —CO$_2$—C$_{1-6}$-aliphatic-heteroaryl, —CO$_2$-aryl, —CO$_2$-heteroaryl; or $Y_1$ and $Y_1'$, or $Y_2$ and $Y_2'$, or $Y_3$ and $Y_3'$, or $Y_4$ and $Y_4'$ jointly stand for =O. Preferably, $Y_1$, $Y_1'$, $Y_2$, $Y_2'$, $Y_3$, $Y_3'$, $Y_4$ and $Y_4'$ are respectively selected independently of one another from the group comprising —H, —F, —Cl, —Br, —I, —CN, —NH$_2$ and —OH.

In a preferred embodiment one of the residues $Y_1$, $Y_1'$, $Y_2$, $Y_2'$, $Y_3$, $Y_3'$, $Y_4$ and $Y_4'$ differs from —H and the remaining residues stand for —H.

It is particularly preferred if $Y_1$, $Y_1'$, $Y_2$, $Y_2'$, $Y_3$, $Y_3'$, $Y_4$ and $Y_4'$ respectively stand for —H.

Preferred embodiments of the compounds according to the invention of the general formula (1) have the general formula (2), (3), (4) or (5):

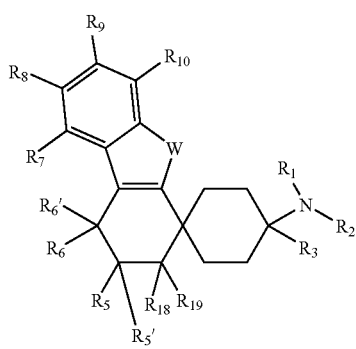

(2)

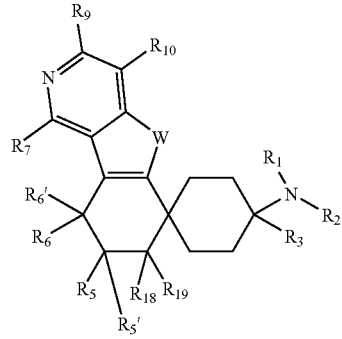

(3)

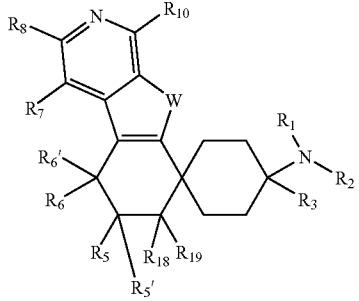

(4)

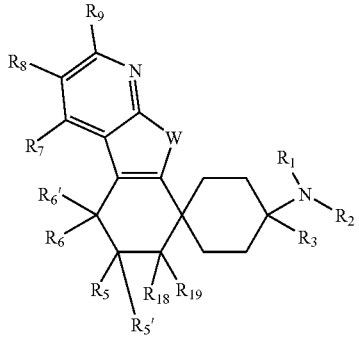

(5)

In a preferred embodiment of the compounds according to the invention W is W —NR$_4$—.

$R_0$ respectively independently stands for —C$_{1-8}$-aliphatic, —C$_{3-12}$-cycloaliphatic, -aryl, -heteroaryl, —C$_{1-8}$-aliphatic-C$_{3-12}$-cycloaliphatic, —C$_{1-8}$-aliphatic-aryl, —C$_{1-8}$-aliphatic-heteroaryl, —C$_{3-8}$-cycloaliphatic-C$_{1-8}$-aliphatic, —C$_{3-8}$-cycloaliphatic-aryl or —C$_{3-8}$-cycloaliphatic-heteroaryl. In this case, —C$_{1-8}$-aliphatic-C$_{3-12}$-cycloaliphatic, —C$_{1-8}$-aliphatic-aryl or —C$_{1-8}$-aliphatic-heteroaryl mean that the residues —C$_{3-12}$-cycloaliphatic, -aryl or -heteroaryl are respectively bonded via a bivalent bridge —C$_{1-8}$-aliphatic-. Preferred examples of —C$_{1-8}$-aliphatic-aryl are —CH$_2$—C$_6$H$_5$, —CH$_2$CH$_2$—C$_6$H$_5$, and —CH=CH—C$_6$H$_5$. In addition, —C$_{3-8}$-cycloaliphatic-C$_{1-8}$-aliphatic, —C$_{3-8}$-cycloaliphatic-aryl or —C$_{3-8}$-cycloaliphatic-heteroaryl mean that the residues —C$_{1-8}$-aliphatic, -aryl or -heteroaryl are respectively bonded via a bivalent bridge —C$_{3-8}$-cycloaliphatic-. A preferred example of —C$_{3-8}$-cycloaliphatic-aryl is -cyclopropyl-phenyl.

$R_1$ and $R_2$, independently of one another, preferably stand for —H; —C$_{1-6}$-aliphatic; —C$_{3-8}$-cycloaliphatic, —C$_{1-6}$-aliphatic-aryl, —C$_{1-6}$-aliphatic-C$_{3-8}$-cycloaliphatic or —C$_{1-6}$-aliphatic-heteroaryl; or residues $R_1$ and $R_2$ together form a ring and represent —CH$_2$CH$_2$OCH$_2$CH$_2$—, —CH$_2$CH$_2$NR$_{11}$CH$_2$CH$_2$— or —(CH$_2$)$_{3-6}$—.

It is more preferred if $R_1$ and $R_2$, independently of one another, stand for —H; —$C_{1-5}$-aliphatic; or residues $R_1$ and $R_2$ together form a ring and represent —$CH_2CH_2OCH_2CH_2$—, —$CH_2CH_2$—$NR_{11}$—$CH_2CH_2$— or —$(CH_2)_{3-6}$—, wherein $R_{11}$ preferably represents —H or —$C_{1-5}$-aliphatic.

Particularly preferred are compounds, in which $R_1$ and $R_2$, independently of one another, stand for —$CH_3$ or —H, wherein $R_1$ and $R_2$ do not represent —H simultaneously; or $R_1$ and $R_2$ form a ring and represent —$(CH_2)_{3-4}$—

The compounds most especially preferred are those, in which $R_1$ and $R_2$ stand for —$CH_3$.

$R_3$ preferably stands for —$C_{1-8}$-aliphatic, —$C_{3-8}$-cycloaliphatic, -aryl, -heteroaryl; or for -aryl, -heteroaryl or —$C_{3-8}$-cycloaliphatic respectively bonded via a —$C_{1-3}$-aliphatic group.

It is particularly preferred if $R_3$ stands for -ethyl, -propyl, -butyl, -pentyl, -hexyl, -heptyl, -cyclopentyl, -cyclohexyl, -phenyl, -benzyl, -naphthyl, -anthracenyl, -thiophenyl, -benzothiophenyl, -furyl, -benzofuranyl, -benzodioxolanyl, -indolyl, -indanyl, -benzodioxanyl, -pyrrolyl, -pyridyl, -pyrimidyl or -pyrazinyl, respectively unsubstituted or mono- or polysubstituted; —$C_{5-6}$-cycloaliphatic, -phenyl, -naphthyl, -anthracenyl, -thiophenyl, -benzothiophenyl, -pyridyl, -furyl, -benzofuranyl, -benzodioxolanyl, -indolyl, -indanyl, -benzodioxanyl, -pyrrolyl, -pyrimidyl, -triazolyl or -pyrazinyl, respectively unsubstituted or mono- or polysubstituted, bonded via a saturated, unbranched —$C_{1-3}$-aliphatic group.

It is more preferred if $R_3$ stands for -propyl, -butyl, -pentyl, -hexyl, -phenyl, -furyl, -thiophenyl, -naphthyl, -benzyl, -benzofuranyl, -indolyl, -indanyl, -benzodioxanyl, -benzodioxolanyl, -pyridyl, -pyrimidyl, -pyrazinyl, -triazolyl or -benzothiophenyl, respectively unsubstituted or mono- or polysubstituted; -phenyl, -furyl or -thiophenyl, respectively unsubstituted or mono- or polysubstituted, bonded via a saturated, unbranched —$C_{1-3}$-aliphatic group.

It is further preferred if $R_3$ stands for -propyl, -butyl, -pentyl, -hexyl, -phenyl, -phenethyl, -thiophenyl, -pyridyl, -triazolyl, -benzothiophenyl or -benzyl, respectively substituted or unsubstituted, particularly preferred for -propyl, -3-methoxypropyl, -butyl, -pentyl, -hexyl, -phenyl, -3-methylphenyl, -3-fluorophenyl, -benzo[1,3]-dioxolyl, -thienyl, -benzothiophenyl, -4-chlorobenzyl, -benzyl, -3-chlorobenzyl, -4-methylbenzyl, -2-chlorobenzyl, -4-fluorobenzyl, -3-methylbenzyl, -2-methylbenzyl, -3-fluorobenzyl, -2-fluorobenzyl, -1-methyl-1,2,4-triazolyl or -phenethyl.

It is especially preferred if $R_3$ stands for -butyl, -ethyl, -3-methoxypropyl, -benzothiophenyl, -phenyl, -3-methylphenyl, -3-fluorophenyl, -benzo[1,3]-dioxolyl, -benzyl, -1-methyl-1,2,4-triazolyl, -thienyl or -phenethyl.

It is most preferred if $R_3$ stands for -phenyl, -benzyl or -phenethyl, respectively unsubstituted or mono- or polysubstituted on the ring; —$C_{1-5}$-aliphatic, —$C_{4-6}$-cycloaliphatic, -pyridyl, -thienyl, -thiazolyl, -imidazolyl, -1,2,4 triazolyl or -benzimidazolyl, unsubstituted or mono- or polysubstituted.

It is particularly preferred if $R_3$ stands for -phenyl, -benzyl, -phenethyl, -thienyl, -pyridyl, -thiazolyl, -imidazolyl, -1,2,4 triazolyl, -benzimidazolyl or -benzyl, unsubstituted or mono- or polysubstituted with —F, —Cl, —Br, —CN, —$CH_3$, —$C_2H_5$, —$NH_2$, —$NO_2$, —SH, —$CF_3$, —OH, —$OCH_3$, —$OC_2H_5$ or —$N(CH_3)_2$; -ethyl, -n-propyl, -2-propyl, -allyl, -n-butyl, -iso-butyl, -sec-butyl, -tert-butyl, -n-pentyl, -iso-pentyl, -neo-pentyl, -n-hexyl, -cyclopentyl or -cyclohexyl, respectively unsubstituted or mono- or polysubstiuiert with —OH, —$OCH_3$ or —$OC_2H_5$, wherein -thienyl, -pyridyl, -thiazolyl, -imidazolyl, -1,2,4-triazolyl and -benzimidazolyl are preferably unsubstituted.

It is particularly preferred if $R_3$ stands for -phenyl, unsubstituted or mono-substituted with —F, —Cl, —CN, —$CH_3$; -thienyl; -ethyl, -n-propyl or -n-butyl, unsubstituted or mono- or polysubstituted with —$OCH_3$, —OH or —$OC_2H_5$, in particular with —$OCH_3$.

$R_4$ preferably stands for —H; —$C_{1-6}$-aliphatic, -aryl, -heteroaryl, —$C_{1-6}$-aliphatic-aryl, —$C_{1-6}$-aliphatic-heteroaryl or —$C_{1-6}$-aliphatic-cycloaliphatic, —$COR_{12}$ or —$SO_2R_{12}$. It is particularly preferred if $R_4$ stands for —H.

It is preferred if $R_5$ and $R_5'$ respectively independently of one another stand for —H, —F, —Cl, —Br, —I, —$NO_2$, —$CF_3$, —$OR_{13}$, —$SR_{13}$, —$S(=O)_2R_{13}$, —$S(=O)_2OR_{13}$, —$S(=O)NR_{14}R_{15}$, —CN, —$C(=O)OR_{13}$, —$C(=O)NR_{13}$, —$C(=O)NR_0OR_0$, —$NR_{14}R_{15}$, —$NHC(=O)R_0$, —$NHC(=O)NHR_0$, —$NHC(=O)N(R_0)_2$, —$NHC(=O)OR_0$, —$NHS(=O)_{1-2}R_0$, or —$R_0$; or $R_5$ and $R_5'$ jointly stand for =O. It is more preferred if $R_5$ and $R_5'$ respectively independently of one another stand for —H, —F, —Cl, —Br, —I, —$NO_2$, —$C_{1-6}$-aliphatic, —$C_{3-8}$-cycloaliphatic, -aryl, -heteroaryl, —$C_{1-6}$-aliphatic-aryl, —$C_{1-6}$-aliphatic-heteroaryl, —$C_{1-6}$-aliphatic-$C_{3-8}$-cycloaliphatic, —$NR_{14}R_{15}$, —$NHC(=O)R_0$, —$NHC(=O)NHR_0$, —$NHC(=O)OR_0$, —$COOR_{13}$, —$CONR_{13}$ or —$OR_{13}$.

In a preferred embodiment $R_5$ and $R_5'$ stand for —H. In another preferred embodiment $R_5$ stands for —H and $R_5'$ differs from —H. In another preferred embodiment both $R_5$ and $R_5'$ differ from —H.

It is additionally preferred if $R_5$ stands for —H, —$C_{1-5}$-aliphatic or —$COOR_{13}$. It is particularly preferred if $R_5$ stands for —$CH_3$, —$CH_2OH$, —COOH or —$COOCH_3$. It is most particularly preferred if $R_5$ stands for —H.

Preferably, $R_6$ and $R_6'$ respectively independently of one another stand for —H, —F, —Cl, —Br, —I, —$NO_2$, —$CF_3$, —$OR_{13}$, —$SR_{13}$, —$S(=O)_2R_{13}$, —$S(=O)_2OR_{13}$, —$S(=O)NR_{14}R_{15}$, —CN, —$C(=O)OR_{13}$, —$C(=O)NR_{13}$, —$C(=O)NR_0OR_0$, —$NR_{14}R_{15}$, —$NHC(=O)R_0$, —$NHC(=O)NHR_0$, —$NHC(=O)N(R_0)_2$, —$NHC(=O)OR_0$, —$NHS(=O)_{1-2}R_0$, or —$R_0$; or $R_6$ and $R_6'$ jointly stand for =O. Preferably, $R_6$ and $R_6'$ respectively independently of one another stand for —H, —F, —Cl, —$NO_2$, —$CF_3$, —$OR_{13}$, —$SR_{13}$, —$S(=O)_2R_{13}$, —$S(=O)_2OR_{13}$, —CN, —$COOR_{13}$, —$NR_{14}R_{15}$, —$C_{1-5}$-aliphatic, —$C_{3-8}$-cycloaliphatic, -aryl- or heteroaryl; or -aryl, —$C_{3-8}$-cycloaliphatic or -heteroaryl respectively bonded via $C_{1-3}$-aliphatic; or $R_5$ and $R_6$ preferably jointly represent —$(CH_2)_n$— with n=2, 3, 4, 5 or 6, wherein individual hydrogen atoms can also be replaced by —F, —Cl, —Br, —I, —$NO_2$, —$CF_3$, —$OR_{13}$, —CN or —$C_{1-5}$-aliphatic.

In a preferred embodiment $R_6$ and $R_6'$ stand for —H. In another preferred embodiment $R_6$ stands for —H and $R_6'$ differs from —H. In another preferred embodiment both $R_6$ and $R_6'$ differ from —H.

Compounds, in which $R_6$ stands for —H, —$C_{1-5}$-aliphatic, -aryl or -aryl bonded via a —$C_{1-3}$-aliphatic group (bridge), are also preferred. It is particularly preferred if $R_6$ stands for —H, —$CH_3$, -phenyl or -benzyl. It is most particularly preferred if $R_6$ stands for —H.

$R_7$, $R_8$, $R_9$ and $R_{10}$, respectively independently of one another, preferably stand for —H, —F, —Cl, —Br, —I, —$NO_2$, —$CF_3$, —$OR_{13}$, —$SR_{13}$, —$SO_2R_{13}$, —$SO_2OR_{13}$, —CN, —$COOR_{13}$, —$NR_{14}R_{15}$; —$C_{1-5}$-aliphatic, —$C_{3-8}$-cycloaliphatic; -aryl or -heteroaryl; or -aryl, —$C_{3-8}$-cycloaliphatic or -heteroaryl respectively bonded via —$C_{1-3}$-aliphatic.

It is more preferred if $R_7$, $R_8$, $R_9$ and $R_{10}$, respectively independently of one another, stand for —H, -methyl, -ethyl, -propyl, -butyl, -pyridyl, —O-benzyl, —F, —Cl, —Br, —I, —$CF_3$, —OH, —$OCH_3$, —$NH_2$, —COOH, —CO—$OCH_3$, —$NHCH_3$, —$N(CH_3)_2$ or —$NO_2$.

It is particularly preferred if $R_7$, $R_8$, $R_9$ and $R_{10}$, respectively independently of one another, stand for —H, —F, —OH, —$CH_3$, —Cl, —$OCH_3$, —Br or —$NO_2$.

In a preferred embodiment $R_7$, $R_8$, $R_9$ and $R_{10}$ stand for —H.

In another preferred embodiment three of the residues $R_7$, $R_8$, $R_9$ and $R_{10}$ stand for —H and the remaining residue, preferably $R_8$ or $R_9$, differs from —H, preferably is —F, —Cl, —OH or —$OCH_3$.

In another preferred embodiment two of the residues $R_7$, $R_8$, $R_9$ and $R_{10}$ stand for —H and the two remaining residues differ from —H.

$R_{11}$, preferably stands for —H, —$C_{1-5}$-aliphatic, —$C_{3-8}$-cycloaliphatic, -aryl, -heteroaryl, —$C_{1-6}$-aliphatic-aryl, —$C_{1-6}$-aliphatic-$C_{3-8}$-cycloaliphatic, —$C_{1-6}$-aliphatic-heteroaryl, —C(=O)aryl, —C(=O)heteroaryl, or —C(=O)$C_{1-6}$-aliphatic.

$R_{12}$ preferably stands for —H, —$C_{1-5}$-aliphatic, —$C_{3-8}$-cycloaliphatic, -aryl- or -heteroaryl, or -aryl, —$C_{3-8}$-cycloaliphatic or -heteroaryl respectively bonded via —$C_{1-3}$-aliphatic, or for —$OR_{13}$ or —$NR_{14}R_{15}$. It is particularly preferred if $R_{12}$ is -aryl, preferably phenyl, bonded via —$C_2$-aliphatic, preferably via —$CH_2CH_2$— or —CH=CH—.

$R_{13}$ preferably stands for —H, —$C_{1-5}$-aliphatic, —$C_{3-8}$-cycloaliphatic, -aryl or -heteroaryl; or -aryl, —$C_{3-8}$-cycloaliphatic or -heteroaryl respectively bonded via —$C_{1-3}$-aliphatic.

$R_{14}$ and $R_{15}$, independently of one another, preferably stand for —H, —$C_{1-5}$-aliphatic, —$C_{3-8}$-cycloaliphatic, -aryl or -heteroaryl; or -aryl, —$C_{3-8}$-cycloaliphatic or -heteroaryl respectively bonded via —$C_{1-3}$-aliphatic; or $R_{14}$ and $R_{15}$ together form —$CH_2CH_2OCH_2CH_2$—, —$CH_2CH_2N$—$R_{16}CH_2CH_2$— or —$(CH_2)_{3-6}$—.

$R_{16}$ preferably stands for —H or —$C_{1-5}$-aliphatic.

$R_{18}$ and $R_{19}$ independently of one another preferably stand for —H, —F, —Cl, —Br, —I, —$NO_2$, —$CF_3$, —$OR_{13}$, —$SR_{13}$, —$S(=O)_2R_{13}$, —$S(=O)_2OR_{13}$, —$S(=O)_2NR_{14}R_{15}$, —CN, —$C(=O)OR_{13}$, —C(=O)—$NR_{13}$, —$C(=O)NR_0OR_0$, —$NR_{14}R_{15}$, —NHC(=O)$R_0$, —NHC(=O)$NHR_0$, —NHC(=O)$N(R_0)_2$, —NHC(=O)$OR_0$, —$NHS(=O)_{1-2}R_0$, or —$R_0$; or $R_{18}$ and $R_{19}$ stand jointly for =O. Preferably, $R_{18}$ and $R_{19}$ respectively independently of one another stand for —H, —F, —Cl, —$NO_2$, —$CF_3$, —$OR_{13}$, —$SR_{13}$, —$S(=O)_2R_{13}$, —$S(=O)_2OR_{13}$, —CN, —$COOR_{13}$, —$NR_{14}R_{15}$, —$C_{1-5}$-aliphatic, —$C_{1-5}$-aliphatic-OH, —$C_{3-8}$-cycloaliphatic, -aryl or -heteroaryl; or -aryl, —$C_{3-8}$-cycloaliphatic or -heteroaryl respectively bonded via $C_{1-3}$-aliphatic. It is more preferred if $R_{18}$ and $R_{19}$, respectively independently of one another, stand for —H, —$C_{1-5}$-aliphatic, —$C_{3-8}$-cycloaliphatic, -aryl or -heteroaryl; or -aryl, —$C_{3-8}$-cycloaliphatic or -heteroaryl respectively bonded via —$C_{1-3}$-aliphatic.

In a preferred embodiment $R_{18}$ and $R_{19}$ stand for —H. In another preferred embodiment $R_{18}$ stands for —H and $R_{19}$ differs from —H. In another preferred embodiment both $R_{18}$ and $R_{19}$ differ from —H.

For the purposes of the description hydrocarbon residues are divided into aliphatic hydrocarbon residues and aromatic hydrocarbon residues.

Aliphatic hydrocarbon residues are themselves divided into non-cyclic aliphatic hydrocarbon residues (="aliphatic") and cyclic aliphatic hydrocarbon residues, i.e. alicyclic hydrocarbon residues (="cycloaliphatic"). Cycloaliphatic compounds can be monocyclic or multicyclic. Alicyclic hydrocarbon residues ("cycloaliphatic") comprise both pure aliphatic carbocycles and aliphatic heterocycles, i.e.—unless expressly specified —"cycloaliphatic" comprises pure aliphatic carbocycles (e.g. cyclohexyl), pure aliphatic heterocycles (e.g. piperidyl or piperazyl) and also non-aromatic, multicyclic, possibly mixed, systems (e.g. decalinyl, decahydroquinolinyl).

Aromatic hydrocarbons are themselves divided into carbocyclic aromatic hydrocarbons (="aryl") and heterocyclic aromatic hydrocarbons (="heteroaryl").

The classification of multicyclic, at least partially aromatic systems preferably depends on whether at least one aromatic ring of the multicyclic system has at least one heteroatom (usually N, O or S) in the ring. If at least one such heteroatom is present in this ring, this is preferably a "heteroaryl" (even if a further carbocyclic aromatic or non-aromatic ring with or without heteroatom is possibly present as additionally present cycle of the multicyclic system); if such a heteroatom is not present in any of the possibly several aromatic rings of the multicyclic system, then this is preferably "aryl" (even if a ring heteroatom is present in a possibly additionally present non-aromatic cycle of the multicyclic system).

Therefore, the following priority in the classification applies within the cyclic substituents: heteroaryl>aryl>cycloaliphatic.

For the purposes of the description monovalent and multivalent, i.e. bivalent, hydrocarbon residues are not distinguished between conceptually, i.e. depending on the context, "$C_{1-3}$-aliphatic" covers e.g. —$C_{1-3}$-alkyl, —$C_{1-3}$-alkenyl and —$C_{1-3}$-alkinyl, as well as e.g. —$C_{1-3}$-alkylene-, —$C_{1-3}$-alkenylene- and $C_{1-3}$-alkinylene.

Aliphatic is preferably respectively a branched or unbranched, saturated or a mono- or polyunsaturated, unsubstituted or mono- or polysubstituted, aliphatic hydrocarbon residue. Where aliphatic is mono- or polysubstituted, the substituents are selected independently of one another from the group comprising —F, —Cl, —Br, —I, —CN, —$NO_2$, —CHO, =O, —$R_0$, —C(=O)$R_0$, —C(=O)OH, —C(=O)$OR_0$, —C(=O)$NH_2$, —C(=O)$NHR_0$, —C(=O)$N(R_0)_2$, —OH, —$OR_0$, —OC(=O)H, —OC(=O)$R_0$, —OC(=O)$OR_0$, —OC(=O)$NHR_0$, —OC(=O)$N(R_0)_2$, —SH, —$SR_0$, —$SO_3H$, —$S(=O)_{1-2}$—$R_0$, —$S(=O)_{1-2}NH_2$, —$NH_2$, —$NHR_0$, —$N(R_0)_2$, —$N^+(R_0)_3$, —$N^+(R_0)_2O^-$, —NHC(=O)$R_0$, —NHC(=O)$OR_0$, —NHC(=O)$NH_2$, —NHC(=O)$NHR_0$, —NHC(=O)$N(R_0)_2$, —$Si(R_0)_3$, —$PO(OR_0)_2$. Thus, "aliphatic" covers acyclic saturated or unsaturated hydrocarbon residues that can be branched or straight-chain, i.e. alkanyls, alkenyls and alkinyls. In this case, alkenyls have at least one C=C double bond and alkinyls have at least one C≡C triple bond. Preferred unsubstituted monovalent aliphatics comprise —$CH_3$, —$CH_2CH_3$, —$CH_2CH_2CH_3$, —$CH(CH_3)_2$, —$CH_2CH_2CH_2CH_3$, —$CH(CH_3)CH_2CH_3$, —$CH_2CH(CH_3)_2$, —$C(CH_3)_3$, —$CH_2CH_2CH_2$—$CH_2CH_3$ and —$CH_2CH_2CH_2CH_2CH_2CH_3$; but also —CH=$CH_2$, —C≡CH, —$CH_2CH$=$CH_2$, —CH=$CHCH_3$, —$CH_2C$≡CH, —C≡$CCH_3$ and —CH=CHCH=$CH_2$. Preferred unsubstituted bivalent aliphatics comprise —$CH_2$—, —$CH_2CH_2$—, —$CH_2CH(CH_3)$—, —$CH(CH_3)$—$CH_2$—, —$CH_2CH_2CH_2$—, —$CH(CH_3)CH_2CH_2$—, —$CH_2CH(CH_3)$—$CH_2$—, —$CH_2CH_2CH(CH_3)$—, —CH—$(CH_2CH_3)CH_2$— and —$CH_2CH_2$—$CH_2CH_2$—; but also —CH=CH—, —C≡C—, —$CH_2CH$=CH—, —CH=$CHCH_2$—, —$CH_2C$≡C— and —C≡$CCH_2$—. Preferred substituted monovalent aliphatics comprise —$CH_2F$, —$CHF_2$, —$CF_3$, —$CH_2CF_3$, —$CF_2CF_3$, —$CH_2OH$, —$CH_2CH_2OH$, —$CH_2CHOHCH_3$, —$CH_2OCH_3$, —$CH_2CH_2OCH_3$ and —$CH_2N(CH_3)_2$. Preferred substituted bivalent aliphatics comprise —$CF_2$—, —$CF_2CF_2$—, —CH$_2$CHOH—, —CHOHCH$_2$— and —CH$_2$CHOHCH$_2$—. -Methyl-, -ethyl-, -n-propyl- and -n-butyl- are particularly preferred.

Cycloaliphatic is preferably respectively a saturated or a mono- or polyunsaturated, unsubstituted or mono- or polysubstituted, aliphatic (i.e. not aromatic), mono- or multicyclic hydrocarbon residue. The number of ring-carbon atoms preferably lies in the specified range (i.e. a "C$_{3-8}$-cycloaliphatic" preferably has 3, 4, 5, 6, 7 or 8 ring-carbon atoms). For the purposes of the description "C$_{3-8}$-cycloaliphatic" is preferably a cyclic hydrocarbon with 3, 4, 5, 6, 7 or 8 ring-carbon atoms, saturated or unsaturated, but not aromatic, wherein possibly one or two carbon atoms are replaced independently of one another by a heteroatom S, N or O. Where cycloalkyl is mono- or polysubstituted, the substituents are selected independently of one another from the group comprising —F, —Cl, —Br, —I, —CN, —NO$_2$, —CHO, =O, —R$_0$, —C(=O)R$_0$, —C(=O)OH, —C(=O)OR$_0$, —C(=O)NH$_2$, —C(=O)NHR$_0$, —C(=O)N(R$_0$)$_2$, —OH, —OR$_0$, —OC(=O)H, —OC(=O)R$_0$, —OC(=O)OR$_0$, —OC(=O)NHR$_0$, —OC(=O)—N(R$_0$)$_2$, —SH, —SR$_0$, —SO$_3$H, —S(=O)$_{1-2}$—R$_0$, —S(=O)$_{1-2}$NH$_2$, —NH$_2$, —NHR$_0$, —N(R$_0$)$_2$, —N$^+$(R$_0$)$_3$, —N$^-$(R$_0$)$_2$O$^-$, —NHC(=O)R$_0$, —NHC(=O)OR$_0$, —NHC(=O)NH$_2$, —NHC(=O)NHR$_0$, —NHC(=O)N(R$_0$)$_2$, —Si(R$_0$)$_3$, —PO(OR$_0$)$_2$. Advantageously, C$_{3-8}$-cycloaliphatic is selected from the group comprising cyclopropyl, cyclobutyl, cyclopentyl, cyclohexyl, cycloheptyl, cyclooctyl, cyclopentenyl, cyclohexenyl, cycloheptenyl and cyclooctenyl, but also tetrahydropyranyl, dioxanyl, dioxolanyl, morpholinyl, piperidinyl, piperazinyl, pyrazolinonyl and pyrrolidinyl.

In association with "aliphatic" or "cycloaliphatic", "mono- or polysubstituted" is preferably understood to mean the mono- or polysubstitution, e.g. the mono-, di-, tri- or 4-substitution, of one or more hydrogen atoms by —F, —Cl, —Br, —I, —OH, —OC$_{1-6}$-alkyl, —OC(=O)C$_{1-6}$-alkyl, —SH, —NH$_2$, —NHC$_{1-6}$-alkyl, —N(C$_{1-6}$-alkyl)$_2$, —C(=O)OC$_{1-6}$-alkyl or —C(=O)OH. Particularly preferred substituents are —F, —Cl, —OH, —SH, —NH$_2$ and —C(=O)OH.

Polysubstituted residues are understood to be those residues that are polysubstituted, e.g. twice or three times either at different or at the same atoms, e.g. three times at the same C-atom, as in the case of —CF$_3$ or —CH$_2$CF$_3$, or at different sites, as in the case of —CH(OH)—CH=CH—CHCl$_2$. The polysubstitution can occur with the same or with different substituents. A substituent may also be substituted itself. Thus, -Oaliphatic also covers —OCH$_2$CH$_2$O—CH$_2$CH$_2$OH, amongst others. It is preferred if aliphatic or cycloaliphatic is substituted with —F, —Cl, —Br, —I, —CN, —CH$_3$, —C$_2$H$_5$, —NH$_2$, —NO$_2$, —SH, —CF$_3$, —OH, —OCH$_3$, —OC$_2$H$_5$ or —N(CH$_3$)$_2$. It is most particularly preferred if aliphatic or cycloaliphatic is substituted with —OH, —OCH$_3$ or —OC$_2$H$_5$.

Aryl preferably respectively independently stands for a carbocyclic ring system with at least one aromatic ring, but without heteroatoms in this ring, wherein the aryl residues can possibly be condensed with further saturated, (partially) unsaturated or aromatic ring systems and each aryl residue can be present in unsubstituted or mono- or polysubstituted form, wherein the aryl substituents are the same or different and can be in any desired and possible position of the aryl. Preferred aryls are phenyl, naphthyl, anthracenyl, phenanthrenyl, fluoranthenyl, fluoroenyl, indanyl and tetralinyl. Phenyl and naphthyl are particularly preferred. Where aryl is mono- or polysubstituted, the aryl substituents can be the same or different and be in any desired and possible position of the aryl, and are selected independently of one another from the group comprising —F, —Cl, —Br, —I, —CN, —NO$_2$, —CHO, =O, —R$_0$, —C(=O)R$_0$, —C(=O)OH, —C(=O)OR$_0$, —C(=O)NH$_2$, —C(=O)NHR$_0$, —C(=O)N(R$_0$)$_2$, —OH, —O(CH$_2$)$_{1-2}$O—, —OR$_0$, —OC(=O)H, —OC(=O)R$_0$, —OC(=O)OR$_0$, —OC(=O)NHR$_0$, —OC(=O)N(R$_0$)$_2$, —SH, —SR$_0$, —SO$_3$H, —S(=O)$_{1-2}$—R$_0$, —S(=O)$_{1-2}$NH$_2$, —NH$_2$, —NHR$_0$, —N(R$_0$)$_2$, —N$^+$(R$_0$)$_3$, —N$^+$(R$_0$)$_2$O$^-$, —NHC(=O)R$_0$, —NHC(=O)OR$_0$, —NHC(=O)NH$_2$, —NHC(=O)NHR$_0$, —NHC(=O)N(R$_0$)$_2$, —Si(R$_0$)$_3$, —PO(OR$_0$)$_2$. Preferred substituted aryls are 2-fluorophenyl, 3-fluorophenyl, 4-fluorophenyl, 2,3-difluorophenyl, 2,4-difluorophenyl, 3,4-difluorophenyl, 2-chlorophenyl, 3-chlorophenyl, 4-chlorophenyl, 2,3-dichlorophenyl, 2,4-dichlorophenyl, 3,4-dichlorophenyl, 2-methoxy-phenyl, 3-methoxy-phenyl, 4-methoxy-phenyl, 2,3-dimethoxy-phenyl, 2,4-dimethoxy-phenyl, 3,4-dimethoxy-phenyl, 2-methyl-phenyl, 3-methyl-phenyl, 4-methyl-phenyl, 2,3-dimethyl-phenyl, 2,4-dimethyl-phenyl and 3,4-dimethyl-phenyl.

Heteroaryl preferably stands for a 5-, 6- or 7-membered cyclic aromatic residue that contains 1, 2, 3, 4 or 5 heteroatoms, wherein the heteroatoms, the same or different, are nitrogen, oxygen or sulphur, and the heterocycle can be unsubstituted or mono- or polysubstituted; wherein in the case of the substitution on the heterocycle, the substituents can be the same or different and can be in any desired and possible position of the heteroaryl; and wherein the heterocycle can also be part of a bi- or polycyclic system. "Heteroaryl" is preferably selected from the group comprising pyrrolyl, indolyl, furyl (furanyl), benzofuranyl, thienyl (thiophenyl), benzothienyl, benzothiadiazolyl, benzooxadiazolyl, benzothiazolyl, benzooxazolyl, benzotriazolyl, benzodioxolanyl, benzodioxanyl, phthalazinyl, pyrazolyl, imidazolyl, thiazolyl, oxazolyl, isoxazoyl, pyridinyl, pyridazinyl, pyrimidinyl, pyrazinyl, pyranyl, indazolyl, purinyl, indolizinyl, quinolinyl, isoquinolinyl, quinazolinyl, carbazolyl, phenazinyl, phenothiazinyl or oxadiazolyl, wherein the bonding can occur via any desirable and possible ring member of the heteroaryl residue. Where heteroaryl is mono- or polysubstituted, the heteroaryl substituents can be the same or different and can be in any desirable and possible position of the heteroaryl, and are selected independently of one another from the group comprising —F, —Cl, —Br, —I, —CN, —NO$_2$, —CHO, =O, —R$_0$, —C(=O)R$_0$, —C(=O)OH, —C(=O)OR$_0$, —C(=O)—NH$_2$, —C(=O)NHR$_0$, —C(=O)N(R$_0$)$_2$, —OH, —O(CH$_2$)$_{1-2}$O—, —OR$_0$, —OC(=O)H, —OC(=O)R$_0$, —OC(=O)OR$_0$, —OC(=O)NHR$_0$, —OC(=O)N(R$_0$)$_2$, —SH, —SR$_0$, —SO$_3$H, —S(=O)$_{1-2}$—R$_0$, —S(=O)$_{1-2}$NH$_2$, —NH$_2$, —NHR$_0$, —N(R$_0$)$_2$, —N$^+$(R$_0$)$_3$, —N$^+$(R$_0$)$_2$O$^-$, —NH—C(=O)R$_0$, —NHC(=O)OR$_0$, —NHC(=O)NH$_2$, —NHC(=O)NHR$_0$, —NHC(=O)N(R$_0$)$_2$, —Si(R$_0$)$_3$, —PO(OR$_0$)$_2$.

With respect to "aryl" or "heteroaryl", "mono- or polysubstituted" are understood to mean the mono- or polysubstitution, e.g. di-, tri-, 4- or 5-substitution, of one or more hydrogen atoms of the ring system.

Particularly preferred are the (hetero)aryl substituents selected independently of one another from —F, —Cl, —Br, —I, —CN, —CHO, —CO$_2$H, —NH$_2$, —NO$_2$, —NHR$_0$, —N(R$_0$)$_2$, —N$^+$(R$_0$)$_3$, —N$^+$(R$_0$)$_2$O$^-$, —SH, —SR$_0$, —OH, —OR$_0$, —C(=O)R$_0$, —CO$_2$R$_0$, —C(=O)NH$_2$, —C(=O)NHR$_0$, —C(=O)N(R$_0$)$_2$, —S(=O)$_{1-2}$R$_0$, —S(=O)$_2$NH$_2$, —SO$_3$H, =O or —R$_0$. Preferred substituents are —F, —Cl, —Br, —I, —OH, —OC$_{1-6}$-alkyl, —O—C(=O)—C$_{1-6}$-alkyl, —SH, —NH$_2$, —NHC$_{1-6}$-alkyl, —N(C$_{1-6}$-alkyl)$_2$, —C(=O)OC$_{1-6}$-alkyl or —C(=O)OH. Particularly preferred substituents are —F, —Cl, —OH, —SH, —NH$_2$ and —C(=O)OH.

The compounds according to the invention can be present in the form of a single stereoisomer or mixture thereof, the free compounds and/or their physiologically compatible salts and/or solvates.

The compounds according to the invention occur on the cyclohexane ring in the form of stereoisomers, depending on the substitution pattern (cis/trans, Z/E or syn/anti isomers).

In a preferred embodiment, the diastereomer excess of the cis-isomer amounts to at least 50% de, more preferred at least 75% de, more preferred at least 90% de, most preferred at least 95% de, and in particular at least 99% de. In another preferred embodiment, the diastereomer excess of the trans-isomer amounts to at least 50% de, more preferred at least 75% de, more preferred at least 90% de, most preferred at least 95% de, and in particular at least 99% de. The two diastereomers differ in their polarity, and therefore in the following the non-polar diastereomer is different from the polar diastereomer. The two diastereomers (in the case of two stereo centres) are present in the form of enantiomer pairs (RR+SS or RS+SR).

Suitable methods for separating the isomers (diastereomers) are known to the person skilled in the art. Column chromatography, preparative HPLC and crystallisation processes can be given as examples. The polarity is, for example, responsible for the sequence in which the two diastereomers are eluted in thin-film chromatography (no reversed phase conditions).

The compounds according to the invention can be chiral or achiral, depending on the substitution pattern.

If the compounds according to the invention are chiral, then they are preferably present as racemate or in concentrated form of an enantiomer. In a preferred embodiment the enantiomer excess(ee) of the S-enantiomer amounts at least 50% ee, more preferred at least 75% ee, more preferred at least 90% ee, most preferred at least 95% ee, and in particular at least 99% ee. In another preferred embodiment, the enantiomer excess (ee) of the R-enantiomer amounts to at least 50% ee, more preferred at least 75% ee, more preferred at least 90% ee, most preferred at least 95% ee, and in particular at least 99% ee.

Suitable methods for separating the enantiomers are known to the person skilled in the art. Preparative HPLC on chiral stationary phases and conversion into diastereomeric intermediates can be given as examples. The conversion into diastereomeric intermediates can occur, for example, as salt formation by means of chiral, enantiomer-pure acids. After separation of the diastereomers thus formed, the salt can then be converted into the free base or another salt again.

Unless expressly specified, each reference to the compounds according to the invention covers all isomers (e.g. stereoisomers, diastereomers, enantiomers) in any desired mixture ratio.

Unless expressly specified, each reference to the compounds according to the invention covers the free compounds (i.e. the forms that are not present in the form of salt) and all physiologically compatible salts.

For the purposes of the description, physiologically compatible salts of the compounds according to the invention are present as salts with anions or acids of the respective compound with inorganic or organic acids, which are physiologically compatible—in particular on application in humans and/or mammals.

Examples of physiologically compatible salts of specific acids are salts of: hydrochloric acid, hydrobromic acid, sulphuric acid, methane sulphonic acid, formic acid, acetic acid, oxalic acid, succinic acid, malic acid, tartaric acid, mandelic acid, fumaric acid, lactic acid, citric acid, glutamic acid, saccharinic acid, monomethyl sebacic acid, 5-oxo-proline, hexane-1-sulphonic acid, nicotinic acid, 2-, 3- or 4-aminobenzoic acid, 2,4,6-trimethyl benzoic acid, α-liponic acid, acetylglycine, acetylsalicylic acid, hippuric acid and/or aspartic acid. The hydrochloride, citrate and hemicitrate are particularly preferred.

Physiologically compatible salts with cations or bases are salts of the respective compound—as anion with at least one, preferably inorganic, cation, which are physiologically compatible—in particular on application in humans and/or mammals. Particularly preferred are the salts of the alkali and earth alkali metals, also ammonium salts, but in particular (mono-) or (di-) sodium, (mono-) or (di-) potassium, magnesium or calcium salts.

The compounds according to the invention are defined by substituents, e.g. by $R_1$, $R_2$ and $R_3$ (substituents of the first generation), which are themselves possibly substituted (substituents of the second generation). Depending on the definition, these substituents of the substituents can themselves be substituted again (substituents of the third generation). If, for example, $Y_1$=—$R_0$, wherein —$R_0$=—$C_{1-8}$-aliphatic (substituent of the first generation), then —$C_{1-8}$-aliphatic can itself be substituted, e.g. with —$OR_0$, wherein $R_0$=-aryl (substituent of the second generation). This gives the functional group —$C_{1-8}$-aliphatic-Oaryl. -Aryl can then in turn be substituted again, e.g. with —Cl (substituent of the third generation). This then gives overall the functional group —$C_{1-8}$-aliphatic-Oaryl-Cl.

In a preferred embodiment, the substituents of the third generation cannot be substituted again, i.e. there are then no substituents of the fourth generation.

In another preferred embodiment, the substituents of the second generation cannot be substituted again, i.e. there are then already no substituents of the third generation. In other words, in this embodiment the functional groups for $R_0$ to $R_{19}$ can possibly be respectively substituted, but the respective substituents cannot then themselves be substituted again.

In another preferred embodiment, the substituents of the first generation can not be substituted again, i.e. there are then neither substituents of the second generation nor substituents of the third generation. In other words, in this embodiment the functional groups for $R_0$ to $R_{19}$ are not respectively substituted.

Compounds are preferred, wherein "aliphatic substituted" or "cycloaliphatic substituted" means aliphatic or cycloaliphatic substituted with —F, —Cl, —Br, —I, —CN, —CH$_3$, —C$_2$H$_5$, —NH$_2$, —NO$_2$, —SH, —CF$_3$, —OH, —OCH$_3$, —OC$_2$H$_5$ or —N(CH$_3$)$_2$; and "aryl substituted" or "heteroaryl substituted" means aryl or heteroaryl substituted with —F, —Cl, —Br, —I, —CN, —CH$_3$, —C$_2$H$_5$, —NH$_2$, —NO$_2$, —SH, —CF$_3$, —OH, —OCH$_3$, —OC$_2$H$_5$ or —N(CH$_3$)$_2$, in the form of the racemate; the enantiomers, diastereomers, mixtures of the enantiomers or diastereomers or a single enantiomer or diastereomer; the bases and/or salts of physiologically compatible salts or cations.

For a preferred embodiment of the compounds according to the invention, it applies that $R_1$ and $R_2$ jointly form a ring and stand for —CH$_2$CH$_2$CH$_2$— or —CH$_2$CH$_2$CH$_2$CH$_2$—. Particularly preferred are compounds, in which $R_1$ and $R_2$ form a ring and jointly represent —CH$_2$CH$_2$CH$_2$—.

Moreover, compounds are also preferred, in which $R_3$ stands for phenyl, benzyl or phenethyl, respectively unsubstituted or mono- or polysubstituted on the ring; —C$_{1-5}$-alkyl, unsubstituted or mono- or polysubstituted; —C$_{4-6}$-cycloalkyl, unsubstituted or mono- or polysubstituted; -pyridyl, -thienyl, -thiazolyl, -imidazolyl, -1,2,4 triazolyl or -benzimidazolyl, unsubstituted or mono- or polysubstituted.

Particularly preferred are compounds, in which $R_3$ stands for -phenyl, -benzyl, -phenethyl, -thienyl, -pyridyl, -thiazolyl, -imidazolyl, -1,2,4 triazolyl, -benzimidazolyl or -benzyl, unsubstituted or mono- or polysubstituted with —F, —Cl, —Br, —CN, —CH$_3$, —C$_2$H$_5$, —NH$_2$, —NO$_2$, —SH, —CF$_3$, —OH, —OCH$_3$, —OC$_2$H$_5$ or —N(CH$_3$)$_2$; -ethyl, -n-propyl, -2-propyl, -allyl, -n-butyl, -iso-butyl, -sec-butyl, -tert-butyl, -n-pentyl, -iso-pentyl, -neo-pentyl, -n-hexyl, -cyclopentyl or -cyclohexyl, respectively unsubstituted or mono- or polysubstituted with —OH, —OCH$_3$ or —OC$_2$H$_5$, wherein -thienyl, -pyridyl, -thiazolyl, -imidazolyl, -1,2,4 triazolyl and -benzimidazolyl are preferably unsubstituted; in particular -phenyl, unsubstituted or mono-substituted with —F, —Cl, —CN, —CH$_3$; -thienyl; -ethyl, -n-propyl or -n-butyl, unsubstituted or mono- or polysubstituted with —OCH$_3$, —OH or —OC$_2$H$_5$, in particular with —OCH$_3$.

For a preferred embodiment of the compounds according to the invention, it applies that $R_5$ stands for —H, —CH$_3$, —COOH, —COOCH$_3$, —CH$_2$O-phenyl, wherein the phenyl residue can be substituted with —F, —Cl, —Br, —I, —CN, —CH$_3$, —C$_2$H$_5$, —NH$_2$, —NO$_2$, —SH, —CF$_3$, —OH, —OCH$_3$, —OC$_2$H$_5$ or —N(CH$_3$)$_2$, or for —CH$_2$OH. Particularly preferred are compounds, in which $R_5$ stands for H.

Also particularly preferred are compounds, in which $R_6$ can represent —H; -methyl, -ethyl, —CF$_3$, -benzyl or -phenyl, wherein the benzyl or phenyl residue can be substituted with —F, —Cl, —Br, —I, —CN, —CH$_3$, —C$_2$H$_5$, —NH$_2$, —NO$_2$, —SH, —CF$_3$, —OH, —OCH$_3$, —OC$_2$H$_5$ or —N(CH$_3$)$_2$. Particularly preferred are spirocyclic cyclohexane derivatives, in which $R_6$ represents H.

Additionally preferred are compounds, in which $R_7$, $R_8$, $R_9$ and $R_{10}$ independently of one another represent —H; —C$_{1-5}$-Alkyl, branched or unbranched, unsubstituted or mono- or polysubstituted; —F, —Cl, —Br, —I, —CF$_3$, —OH, —OCH$_3$, —NH$_2$, —COOH, —COOCH$_3$, —NHCH$_3$, -thienyl, -pyrimidinyl, -pyridyl, —N(CH$_3$)$_2$ or —NO$_2$; preferably one of the residues $R_7$, $R_8$, $R_9$ and $R_{10}$ stands for —H; —C$_{1-5}$-alkyl, branched or unbranched, unsubstituted or mono- or polysubstituted; for —F, —Cl, —Br, —I, —OH, —OCH$_3$, —COOH, —COOCH$_3$, —NH$_2$, —NHCH$_3$ or —N(CH$_3$)$_2$ or —NO$_2$, whereas the remaining residues are —H; or two of the residues $R_7$, $R_8$, $R_9$ and $R_{10}$ independently of one another stand for —H; —C$_{1-5}$-Alkyl, branched or unbranched, unsubstituted or mono- or polysubstituted; for —F, —Cl, —Br, —I, —OH, —OCH$_3$, —COOH, —COOCH$_3$, —NH$_2$, —NHCH$_3$ or —N(CH$_3$)$_2$ or —NO$_2$, whereas the remaining residues are —H. Particularly preferred are spirocyclic cyclohexane derivatives, in which $R_7$, $R_8$, $R_9$ and $R_{10}$ independently of one another stand for —H, —F, —OH, —Cl or —OCH$_3$.

Preferred embodiments of the compounds according to the invention of the general formulae (2) have the general formula (2.1) or (2.2) or (2.3) or (2.4):

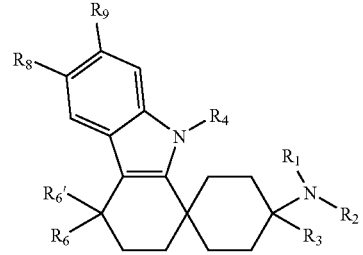 (2.1)

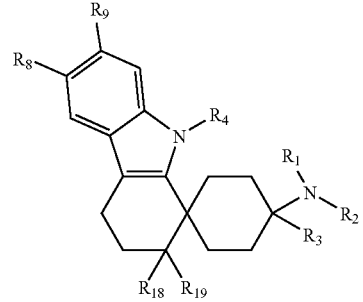 (2.2)

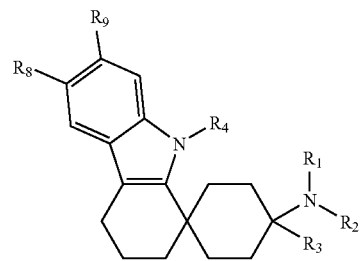 (2.3)

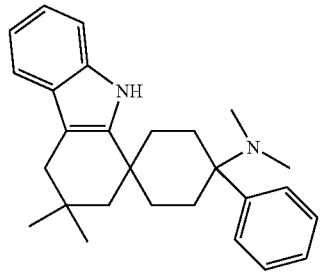 (2.4)

Particularly preferred representatives of the compounds of the general formulae (2.1), (2.2), (2.3) or (2.4) are specified below:

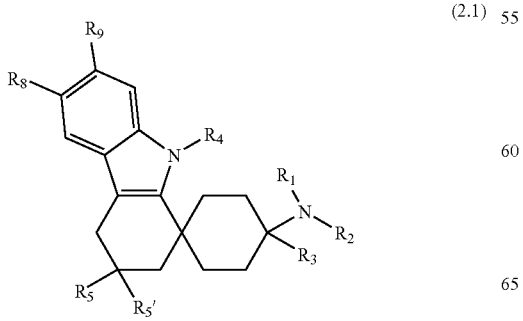 E1

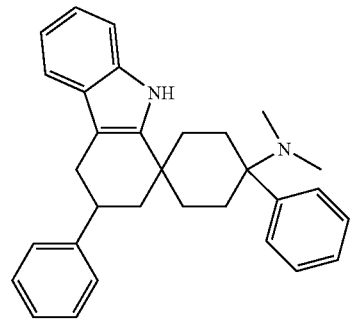 E2

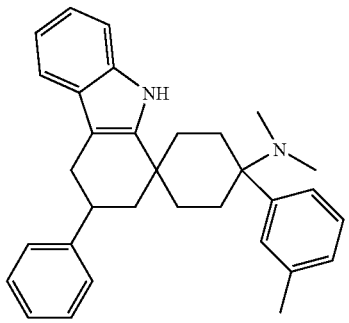

E3

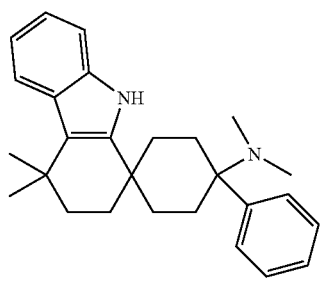

E4

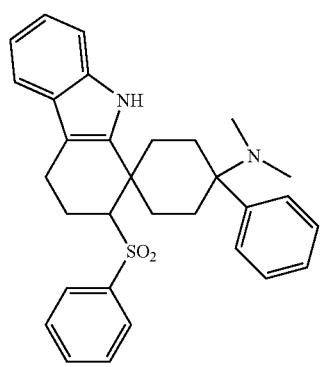

E5

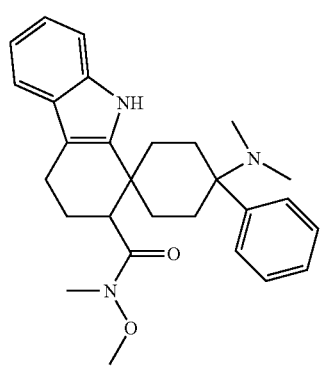

E6

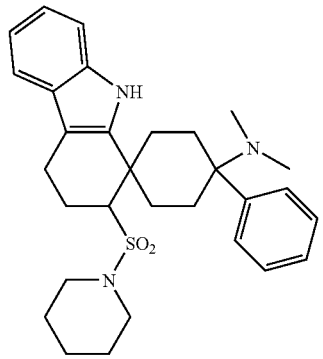

E7

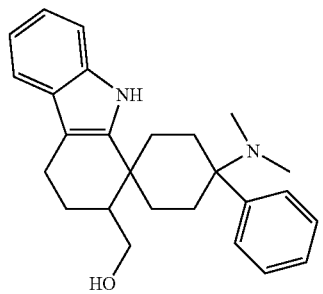

E8

Preferred embodiments of the compounds according to the invention of the general formulae (2.1) have the general formula (2.1.1):

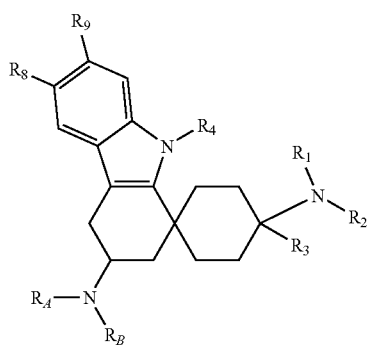

(2.1.1)

wherein $R_A$ and $R_B$ are selected independently of one another from the group comprising —H, —$C_{1-6}$-aliphatic, —C(=O)—$C_{1-6}$-aliphatic, —C(=O)—$C_{3-8}$-cycloaliphatic, —C(=O)—$C_{1-6}$-aliphatic-$C_{3-8}$-cycloaliphatic, —C(=O)—$C_{1-6}$-aliphatic-aryl, —C(=O)—$C_{1-6}$-aliphatic-heteroaryl, —C(=O)-aryl, —C(=O)-heteroaryl, —C(=O)—NH$C_{1-6}$-aliphatic, —C(=O)—NH$C_{3-8}$-cycloaliphatic, —C(=O)—NH$C_{1-6}$-aliphatic-$C_{3-8}$-cycloaliphatic, —C(=O)—NH$C_{1-6}$-aliphatic-aryl, —C(=O)—NH$C_{1-6}$-aliphatic-heteroaryl, —C(=O)—NH aryl, —C(=O)—NH heteroaryl, —C(=O)—N($C_{1-6}$-aliphatic)$_2$, —C(=O)—N($C_{3-8}$-cycloaliphatic)$_2$, —C(=O)—N($C_{1-6}$-aliphatic-$C_{3-8}$-cycloaliphatic)$_2$, —C(=O)—N($C_{1-6}$-aliphatic-aryl)$_2$, —C(=O)—N($C_{1-6}$-aliphatic-heteroaryl)$_2$, —C(=O)—N(aryl)$_2$, —C(=O)—N(heteroaryl)$_2$, —C(=O)—O$C_{1-6}$-aliphatic, —C(=O)—O$C_{3-8}$-cycloaliphatic, —C(=O)—O$C_{1-6}$-aliphatic-$C_{3-8}$-cycloaliphatic, —C(=O)—O$C_{1-6}$-aliphatic-aryl, —C(=O)—O$C_{1-6}$-aliphatic-heteroaryl, —C(=O)-Oaryl and —C(=O)—Oheteroaryl. Preferably, $R_A$ is —H and $R_B$ differs from —H.

Particularly preferred representatives of the compounds of the general formula (2.1.1) are specified below:
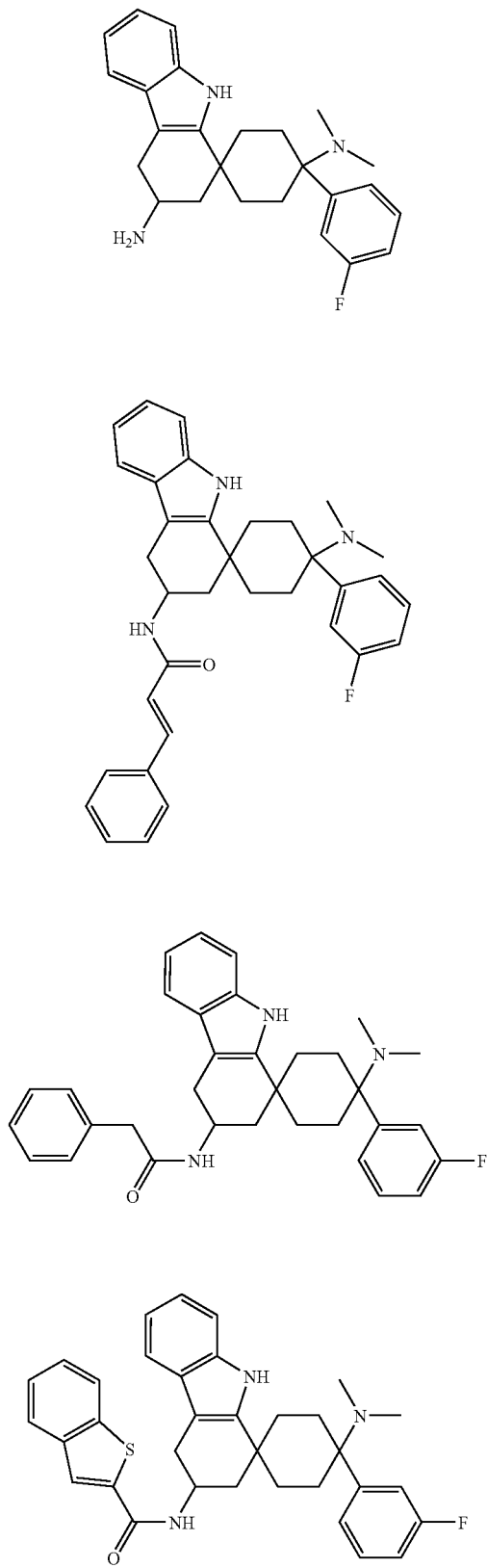
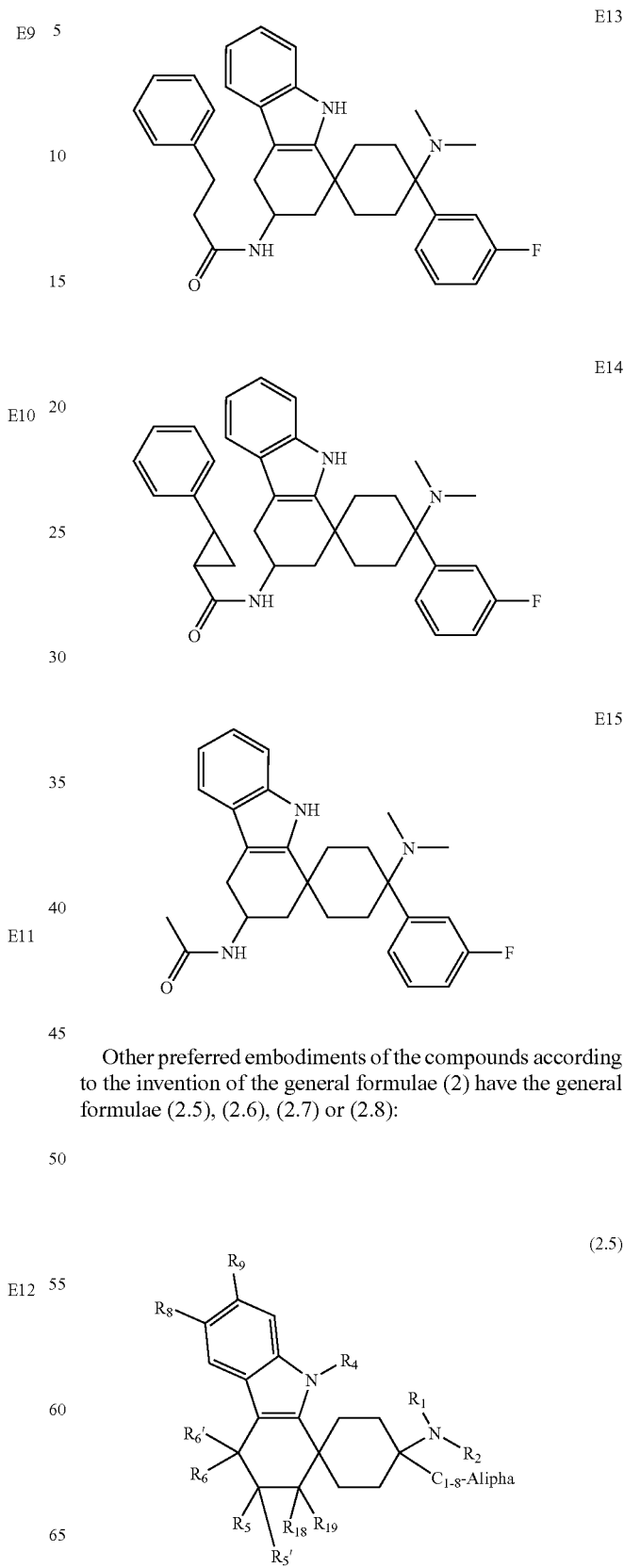
Other preferred embodiments of the compounds according to the invention of the general formulae (2) have the general formulae (2.5), (2.6), (2.7) or (2.8):

-continued
(2.6)
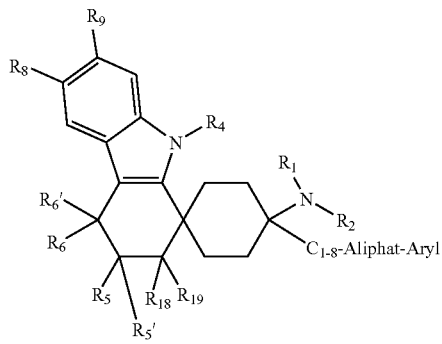
(2.7)
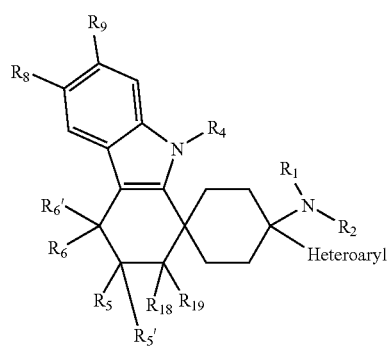
(2.8)
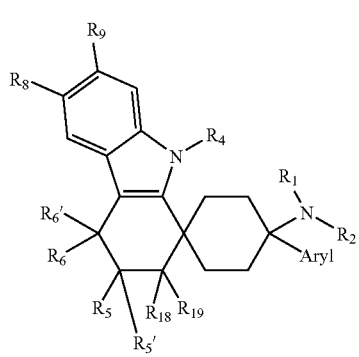
[Aliphat=Aliphatic]
Preferred representatives of the compounds of the general formulae (2.5), (2.6), (2.7) or (2.8) are shown below:
E16
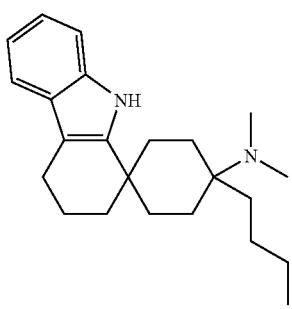
-continued
E17
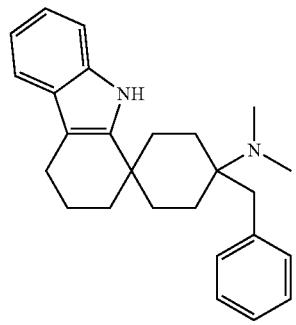
E18
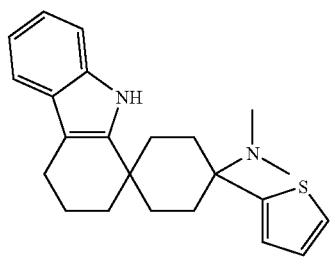
E19
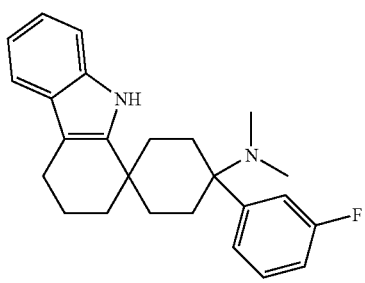
Other preferred embodiments of the compounds according to the invention of the general formulae (2) have the general formula (2.9) or (2.10):
(2.9)
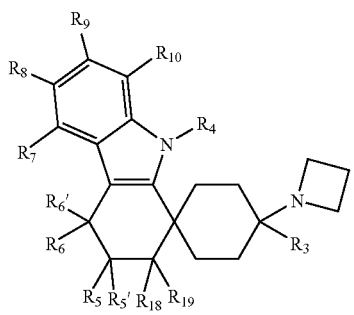

-continued (2.10)

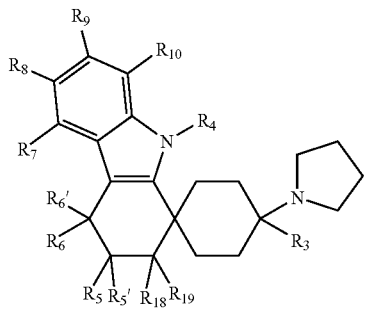

Preferred representatives of the general formulae (2.9) or (2.10) are shown below:

E20

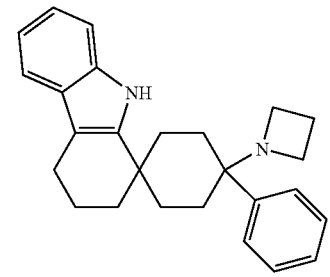

E21

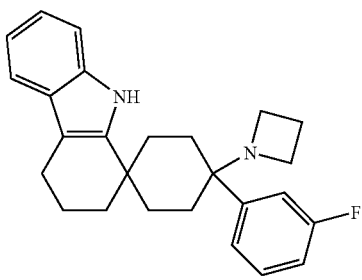

Compounds of the general formula (6) are particularly preferred according to the invention (6)

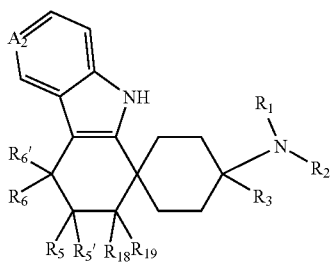

wherein
$A_2$ stands for —N= or —$CR_8$=,
$R_0$ respectively independently stands for —$C_{1-8}$-aliphatic, —$C_{3-12}$-cycloaliphatic, -aryl, -heteroaryl, —$C_{1-8}$-aliphatic-$C_{3-12}$-cycloaliphatic, —$C_{1-8}$-aliphatic-aryl, —$C_{1-8}$-aliphatic-heteroaryl, —$C_{3-8}$-cycloaliphatic-$C_{1-8}$-aliphatic, —$C_{3-8}$-cycloaliphatic-aryl or —$C_{3-8}$-cycloaliphatic-heteroaryl;
$R_1$ stands for —$CH_3$;
$R_2$ stands for —H or —$CH_3$;
or $R_1$ and $R_2$ together stand for —$(CH_2)_{3-4}$—;
$R_3$ stands for —$C_{1-6}$-aliphatic, -aryl, -heteroaryl, —$C_{1-6}$-aliphatic-aryl or —$C_{1-6}$-aliphatic-heteroaryl;
$R_5, R_5', R_6, R_6', R_8, R_{18}$ and $R_{19}$ respectively independently of one another stand for —H, —F, —Cl, —Br, —I, —$NO_2$, —$CF_3$, —$OR_{13}$, —$SR_{13}$, —S(=O)$_2R_{13}$, —S(=O)$_2OR_{13}$, —S(=O)$_2NR_{14}R_{15}$, —CN, —C(=O)$OR_{13}$, —C(=O)$NR_{13}$, —C(=O)$NR_0OR_0$, —$NR_{14}R_{15}$, —NHC(=O)$R_0$, —NHC(=O)$NHR_0$, —NHC(=O)$N(R_0)_2$, —NHC(=O)$OR_0$, —NHS(=O)$_{1-2}R_0$, =O or —$R_0$;
$R_{13}$ respectively independently stands for —H or —$R_0$; and
$R_{14}$ and $R_{15}$ independently of one another stand for —H or —$R_0$.

Most particularly preferred are compounds selected from the group comprising N,N,3,3-tetramethyl-4'-phenyl-2,3,4,9-tetrahydrospiro[carbazole-1,1'-cyclohexane]-4'-amine; N,N-dimethyl-3,4'-diphenyl-2,3,4,9-tetrahydro-spiro[carbazole-1,1'-cyclohexane]-4'-amine; 4'-(3-fluorophenyl)-N,N-dimethyl-3-phenyl-2,3,4,9-tetrahydrospiro[carbazole-1,1'-cyclohexane]-4'-amine; N,N,4,4-tetramethyl-4'-phenyl-2,3,4,9-tetrahydrospiro[carbazole-1,1'-cyclohexane]-4'-amine; N,N-dimethyl-4'-phenyl-2-(phenylsulphonyl)-2,3,4,9-tetrahydrospiro[carbazole-1,1'-cyclohexane]-4'-amine; 4'-(dimethylamino)-N-methoxy-N-methyl-4'-phenyl-2,3,4,9-tetrahydrospiro[carbazole-1,1'-cyclohexane]-2-carboxamide; N,N-dimethyl-4'-phenyl-2-(piperidin-1-ylsulphonyl)-2,3,4,9-tetrahydrospiro[carbazole-1,1'-cyclohexane]-4'-amine; (4'-(dimethylamino)-4'-phenyl-2,3,4,9-tetrahydrospiro[carbazole-1,1'-cyclohexane]-2-yl) methanol; N4',N4'-dimethyl-4'-(3-fluorophenyl)-2,3,4,9-tetrahydrospiro[carbazole-1,1'-cyclohexane]-3,4'-diamine; N-(4'-(dimethylamino)-4'-(3-fluorophenyl)-2,3,4,9-tetrahydrospiro[carbazole-1,1'-cyclohexane]-3-yl)cinnamamide; N-(4'-(dimethylamino)-4'-(3-fluorophenyl)-2,3,4,9-tetrahydrospiro[carbazole-1,1'-cyclohexane]-3-yl)-2-phenylacetamide; N-(4'-(dimethylamino)-4'-(3-fluorophenyl)-2,3,4,9-tetrahydrospiro[carbazole-1,1'-cyclohexane]-3-yl)benzo[b]thiophen-2-carboxamide; N-(4'-(dimethylamino)-4'-(3-fluorophenyl)-2,3,4,9-tetrahydrospiro[carbazole-1,1'-cyclohexane]-3-yl)-3-phenylpropanamide; N-(4'-(dimethylamino)-4'-(3-fluorophenyl)-2,3,4,9-tetrahydrospiro[carbazole-1,1'-cyclohexane]-3-yl)-2-phenylcyclopropane carboxamide; N-(4'-(dimethylamino)-4'-(3-fluorophenyl)-2,3,4,9-tetrahydrospiro[carbazole-1,1'-cyclohexane]-3-yl)acetamide; 4'-butyl-N,N-dimethyl-2,3,4,9-tetrahydrospiro[carbazole-1,1'-cyclohexane]-4'-amine; 4'-benzyl-N,N-dimethyl-2,3,4,9-tetrahydrospiro[carbazole-1,1'-cyclohexane]-4'-amine; N,N-dimethyl-4'-(thiophen-2-yl)-2,3,4,9-tetrahydrospiro[carbazole-1,1'-cyclohexane]-4'-amine; 4'-(3-fluorophenyl)-N,N-dimethyl-2,3,4,9-tetrahydrospiro[carbazole-1,1'-cyclohexane]-4'-amine; 4'-(acetidin-1-yl)-4'-phenyl-2,3,4,9-tetrahydrospiro[carbazole-1,1'-cyclohexane]; 4'-(acetidin-1-yl)-4'-(3-fluorophenyl)-2,3,4,9-tetrahydrospiro[carbazole-1,1'-cyclohexane], 4'-

(acetidin-1-yl)-4'-phenyl-2,3,4,9-tetrahydrospiro[carbazole-1,1'-cyclohexane] (GRT15126H), N,N-dimethyl-N-(4-butyl-2',3',4',9'-tetrahydro-1H-spiro[cyclohexane-1,1'-carbazole]-4-yl)amine, 4'-benzyl-N,N-dimethyl-2,3,4,9-tetrahydrospiro[carbazole-1,1'-cyclohexane]-4'-amine, 4'-(3-fluorophenyl)-N,N-dimethyl-2,3,4,9-tetrahydrospiro[carbazole-1,1'-cyclohexane]-4'-amine, N,N-dimethyl-4'-(thiophen-2-yl)-2,3,4,9-tetrahydrospiro[carbazole-1,1'-cyclohexane]-4'-amine, (S)—N,N,3-trimethyl-4'-phenyl-2,3,4,9-tetrahydrospiro[carbazole-1,1'-cyclohexane]-4'-amine, or their physiologically compatible salts and/or solvates.

The compounds according to the invention act, for example, on the relevant ORL1-receptor in association with different diseases, and therefore they are suitable as pharmaceutical active substance in a medication.

Therefore, the invention additionally relates to medications, which contain at least one compound according to the invention, as well as possibly suitable additives and/or adjuvants and/or possibly further active substances.

The compounds according to the invention have an affinity to the μ-opioid or to the ORL1-receptor comparable to the compounds disclosed as exemplary compounds in WO 2004/043967. However, compared to these compounds they exhibit a higher selectivity with respect to the kappa-opioid receptor, which is responsible for side-effects such as e.g. dysphoria, sedation and diuresis. Therefore, they are particularly suitable for drug development.

Besides at least one compound according to the invention, the medications according to the invention possibly contain suitable additives and/or adjuvants, hence also support materials, fillers, solvents, dilutants, colouring agents and/or binders, and can be administered as liquid medications in the form of injectable solutions, drops or juices, as semisolid medications in the form of granules, tablets, pellets, patches, capsules, plasters/spray plasters or aerosols. The selection of adjuvants etc. as well as the quantities thereof to be used are dependent on whether the medication is to be applied orally, perorally, parenterally, intravenously, intraperitoneally, intradermally, intramuscularly, intranasally, bucally, rectally or locally, e.g. onto the skin, mucous membranes or into the eyes. Preparations in the form of tablets, coated tablets, capsules, granules, drops, juices and syrups are suitable for oral application, solutions, suspensions, readily reconstituted dry preparations as well as sprays are suitable for parenteral, topical and inhalatory application. Compounds according to the invention in a depot, in dissolved form or in a plaster, possibly with the addition of skin-penetration promoters, are suitable preparations for percutaneous application. Preparation forms that may be applied orally or percutaneously can release the compounds according to the invention in a delayed manner. The compounds according to the invention can also be applied in parenteral long-term depot forms such as e.g. implants or implanted pumps. In principle, other additional active substances known to the skilled person can be added to the medications according to the invention.

The amount of active substance to be administered to the patient varies depending on the weight of the patient, on the type of application, the indication and the degree of severity of the disease. Usually, 0.00005 to 50 mg/kg, preferably 0.001 to 0.5 mg/kg, of at least one compound according to the invention are applied.

For all the above-mentioned forms of the medication according to the invention it is particularly preferred if, besides at least one compound according to the invention, the medication also contains a further active substance, in particular an opioid, preferably a strong opioid, in particular morphine, or an anaesthetic, preferably hexobarbital or halothane.

In a preferred form of the medication, a contained compound according to the invention is present in the form of pure diastereomer and/or enantiomer.

The ORL1-receptor was identified in particular in the pain process. Compounds according to the invention can be used accordingly for the production of a medication for the treatment of pain, in particular of acute, neuropathic or chronic pain.

Therefore, the invention additionally relates to the use of a compound according to the invention for the production of a medication for the treatment of pain, in particular of acute, visceral, neuropathic or chronic pain.

The invention further relates to the use of a compound according to the invention for the treatment of anxiety conditions, stress and stress-related syndromes, depressive illnesses, epilepsy, Alzheimer's disease, senile dementia, general cognitive dysfunctions, learning and memory disabilities (as nootropic), withdrawal symptoms, alcohol and/or drug and/or medication misuse and/or dependence, sexual dysfunctions, cardiovascular diseases, hypotension, hypertension, tinitus, pruritus, migraine, hearing impairment, deficient intestinal motility, eating disorders, anorexia, bulimia, mobility disorders, diarrhoea, cachexia, urinary incontinence, or as muscle relaxant, anticonvulsive or anaesthetic, or for coadministration in the treatment with an opioid analgesic or with an anaesthetic, for diuresis or anti-natriuresis, anxiolysis, for modulating movement activity, for modulating neurotransmitter release and for treating neuro-degenerative diseases associated therewith, for treating withdrawal symptoms and/or for reducing the addiction potential of opioids.

In this case, it can be preferred in one of the above uses if a used compound is present as a pure diastereomer and/or enantiomer, as a racemate or as non-equimolar or equimolar mixture of the diastereomers and/or enantiomers.

The invention additionally relates to a method for treating, in particular in one of the aforementioned indications, a non-human mammal or human, which or who requires a treatment for pain, in particular chronic pain, by the administration of a therapeutically effective dose of a compound according to the invention or a medication according to the invention.

The invention further relates to a method for producing the compounds according to the invention as outlined in the following description and examples.

In a preferred embodiment, the synthesis of the compounds according to the invention follows the following general synthesis diagram:

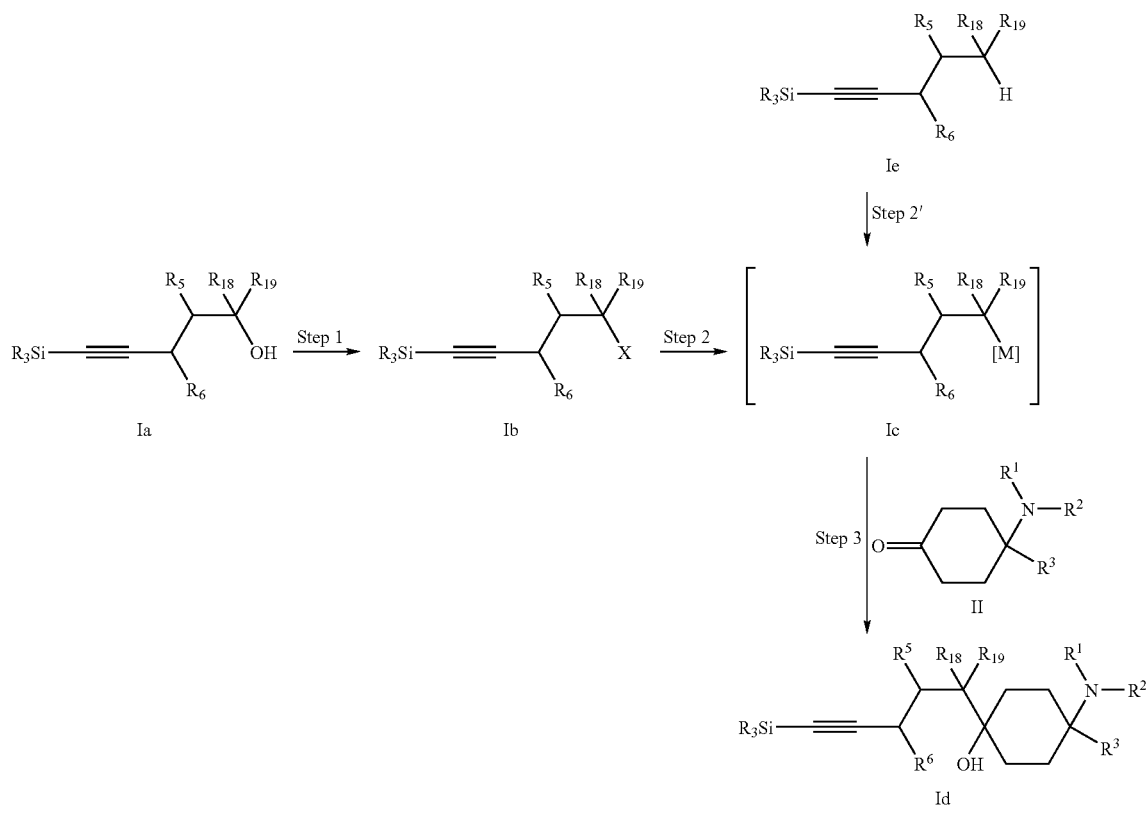

In step 1 alcohols of the general formula Ia are converted either after conversion into a leaving group (e.g. —OSO$_2$-Me —OSO$_2$-p-toluol, —OTf) or directly (in the sense of a Mukaiyama redox condensation) into halides of the general formula Ib (X—Cl, Br, I). These are converted by halogen metal exchange either to the corresponding lithium organyls ([M]=Li) or Grignard reagents ([M]=MgX) of type Ic (step 2). Alternatively, in step 2' lithium organyls of type Ic are produced working from alkines of the general formula Ie (with R$_{18}$ or R$_{19}$=e.g. SO$_2$Ph, SOPh, —CN, —C(=O)N (CH$_3$)OCH$_3$) by deprotonation with lithium amides (e.g. LDA). In step 3 the metallised organyls of the general formula Ic are converted to the corresponding alkine units of type Id in the sense of a 1,2-addition to the carbonyl group of cyclohexanones of the general formula II. The syntheses of the cyclohexanone derivatives with the general formula II are known in the specialist literature (cf. e.g. WO05066183, WO040043967, WO0290317, U.S. Pat. No. 4,065,573, Lednicer et al., *J. Med. Chem.*, 23, 1980, 424-430).

In another preferred embodiment the synthesis of the compounds according to the invention follow the following general synthesis diagram (Larock reaction and spirocyclisation):

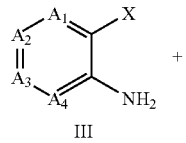

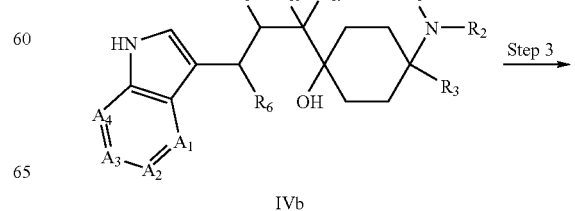

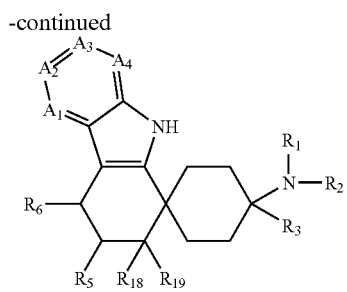

In step 1 compounds of the general formula III, in which X stands for a halogen residue or a sulphonic acid ester, are converted to indoles of the general formula IVa in the sense of an indole synthesis according to Larock with the addition of a palladium catalyst with alkines of the general formula Id. Compounds of the general formula III are commercially available (exemplary syntheses, see also WO2008009416). In step 2 compounds of the general formula IVa are desilylated in the presence of fluoride or in the presence of an organic or inorganic acid and converted to compounds of the general formula IVb. For the production of spirocyclic compounds of the general formula I, the alcohols of the general formula IVb are converted with the addition of an organic acid or trimethylsilyl ester thereof or an inorganic acid or with the addition of a transition metal salt.

With respect to further details on the synthesis of the compounds according to the invention, in particular with respect to the synthesis of suitable educt units, reference is additionally made to the following in their full scope: WO2004/043967, WO2005/063769, WO2005/066183, WO2006/018184, WO2006/108565, WO2007/124903 and WO2008/009416. A skilled person is aware that suitable educt units for the synthesis of the compounds according to the invention can be produced in a similar manner to the synthesis diagrams and exemplary embodiments disclosed in these publications.

EXAMPLES

The following examples serve to explain the invention in more detail, while not restricting it.

The yields of the compounds produced are not optimised.

All temperatures are uncorrected. The term "ether" means diethyl ether, "EE" ethyl acetate and "DCM" dichloromethane. The term "equivalents" means substance amount equivalents, "mp" melting point or melting range, "decomp." decomposition, "RT" room temperature, "abs." absolute (free from water), "rac." racemic, "conc." concentrated, "min" minutes, "h" hours, "d" days, "% vol." percent by volume, "% m" percent by mass and "M" is a concentration detail in mol/l.

Silica gel 60 (0.040-0.063 mm) from E. Merck, Darmstadt was used as the stationary phase for the column chromatography. The thin-film chromatography tests were conducted with silica gel 60 F 254 HPTLC chromatoplates from E. Merck, Darmstadt. The mixture ratios of mobile solvents for chromatography tests are always given in volume/volume.

Synthesis Specifications a) Unit Syntheses—Alkines

Triphenylphosphine diiodide

A suspension of iodine (13.0 g, 51 mmol) and toluol (100 mL) was heated with reflux for 20 min. The solution formed was cooled to room temperature and added in drops to a solution of triphenylphosphine (14.0 g, 53 mmol) in anhydrous diethyl ether (100 mL). The separated yellow precipitate was filtered off and washed with diethyl ether.

Yield: 26.4 g (96%), yellow solid

Melting point: 140-145° C.

Triethyl-(5-iodopent-1-inyl)silane

A solution of 5-(triethylsilyl)-4-pentin-1-ol (416 g, 2.1 mmol) in absolute acetonitrile (20 mL was added in drops to a solution of triphenylphosphine diiodide (2.80 g, 5.4 mmol) and imidazole (1.04 g, 15.4 mmol) with argon and stirred overnight at room temperature. The raw product was purified by means of flash chromatography (38 g, 20×2.5 cm) with cyclohexane/ethyl acetate (9:1).

Yield: 450 mg (70%), colourless oil $^1$H-NMR (DMSO-$d_6$): 0.51-0.57 (m, 6H); 0.92-0.97 (m, 9H); 1.90 (quint, 2H, J=6.8 Hz); 2.35 (t, 2H, J=6.8 Hz); 3.34 (t, 2H, J=6.8 Hz).

4-dimethylamino-4-phenyl-1-(5-triethylsilanyl-pent-4-inyl)cyclohexanol

A 1.7 M solution of tert-butyl lithium (18.4 mL, 31.2 mmol) in pentane was incorporated directly by cannula into a solution of triethyl-(5-iodopent-1-inyl)silane (4.81 g, 15.6 mmol) in anhydrous diethyl ether (150 mL) at −75° C. with argon, wherein the inside temperature was held between −70° C. and −75° C. After stirring for 2 h at −75° C. a solution of 4-(dimethylamino)-4-phenylcyclohexanone (3.39 g, 15.6 mmol, synthesis cf. WO2008009415, ketone unit Ket-10) in anhydrous diethyl ether (150 mL) was slowly added in drops, stirred for a further 30 min at −75° C. and the reaction solution was then heated to room temperature. The reaction mixture was then mixed with saturated ammonium chloride solution (100 mL), the phases were separated, the aqueous phase extracted with diethyl ether (3×50 mL), the combined organic phases washed with sodium chloride solution (50 mL), dried with sodium sulphate and concentrated to low volume in a vacuum. The raw product was purified by means of flash chromatography (400 g, 20×7.5 cm) with ethyl acetate/methanol (9:1).

Yield: 1.70 g (28%), yellow oil, a diastereomer.

Triphenyl-(5-trimethylsilylpent-4-inyl)phosphonium iodide

A solution of triethyl-(5-iodpent-1-inyl)silane (5.02 g, 16.3 mmol) and triphenylphosphine (3.94 g, 15 mmol) in absolute ethanol (100 mL) was stirred 4 h with reflux and overnight at 50° C. and then heated once again with reflux for 7 h. The reaction solution was then concentrated to low volume in a vacuum, the yellowish crystals formed were mixed with diethyl ether (50 mL) and stirred. The diethyl ether was itself concentrated to low volume in a vacuum and the crystals mixed with ethyl acetate (50 mL). After standing in the refrigerator for 24 h the crystals were aspirated, washed with cold ethyl acetate (50 mL) and dried in an exsiccator over phosphorus pentoxide.

Yield: 5.51 g (70%), white solid $^1$H-NMR (DMSO-$d_6$): 0.51 (q, J=7.8, 6H); 0.88 (t, J=7.9, 9H); 1.71 (t, J=7.4, 2H); 2.48-2.55 (m, 2H); 3.52-3.62 (m, 2H); 7.68 (m, 15H).

b) EXAMPLES

Example No. 1 and Example No. 2

Step 1

4-dimethylamino-4-phenyl-1-[3-(2-triethylsilanyl-1H-indol-3-yl)propyl]cyclohexanol A mixture of 4-dimethylamino-4-phenyl-1-(5-triethylsilanyl-pent-4-inyl)cyclohexanol (504 mg, 1.26 mmol), iodoaniline (331 mg, 1.51 mmol), [1,3-bis-(2,6-diisopropylphenyl)-imidazol-2-ylidene]-(3-chloropyridyl)palladium(II)-chloride (PEPPSI, 171 mg, 0.25 mmol) and sodium carbonate (668 mg, 6.3 mmol) was evacuated for 30 min (oil pump). It was then flushed with argon and absolute N,N-dimethylformamide (5 mL, previously flushed for 1 h with argon) was added by syringe via a Schlenk tube. The mixture was stirred for 18 h at 100° C. and changed colour to dark brown during this. The reaction mixture was then concentrated to low volume in a vacuum, the residue taken up several times in toluol (3×10 mL) and concentrated to low volume again in each case, distributed between water and ethyl acetate (20 mL each) and the phases separated again. The aqueous phase was extracted with ethyl acetate (2×30 mL), the combined organic phases were washed with 1 M sodium thiosulphate solution (30 mL) and saturated sodium chloride solution (50 mL), dried with sodium sulphate and concentrated to low volume in a vacuum. The raw product (750 mg) was purified by means of flash chromatography (38 g, 20×2.5 cm) with chloroform/methanol (97:3). The mixed fractions (489 mg) obtained were purified once again by means of MPLC [LiChroprep Si60 (15-25 μm), 130 g, 46×2.6 cm] also with chloroform/methanol (97:3).

Yield: 406 mg (66%)

Melting point: 79-83° C.

$^1$H-NMR (DMSO-$d_6$): 0.87-0.92 (m, 6H); 0.93-0.98 (m, 9H); 1.25-1.32 (m, 2H); 1.45-1.52 (m, 2H); 1.57-1.70 (m, 4H); 1.76-1.84 (m, 2H); 1.89 (s, 6H); 2.12-2.23 (m, 2H); 2.73 (t, 2H, J=7.7 Hz); 3.80 (s, 1H); 6.94 (t, 1H; J=7.0 Hz); 7.05 (t, 1H; J=7.0 Hz); 7.19-7.24 (m, 1H); 7.30-7.34 (m, 4H); 7.36 (d, 1H; J=8.2 Hz); 7.50 (d, 1H, J=8.0 Hz); 10.35 (s, 1H). $^{13}$C-NMR (DMSO-$d_6$): 3.3 (3C); 7.4 (3C); 25.8; 26.4; 28.4 (2C); 32.5 (2C); 37.7 (2C); 42.9; 58.8; 68.7; 109.3; 111.2; 117.8; 118.4; 121.1; 125.3; 126.0; 126.7 (2C); 127.2 (2C); 128.2; 129.7; 138.9.

Step 2

4-dimethylamino-1-[3-(1H-indol-3-yl)propyl]-4-phenylcyclohexanol

A solution of 4-dimethylamino-4-phenyl-1-[3-(2-triethylsilanyl-1H-indol-3-yl)propyl]cyclohexanol (852 mg, 1.8 mmol) in absolute tetrahydrofuran (50 mL) was mixed with tetra-n-butyl ammonium fluoride trihydrate (1.66 g, 5.3 mmol), stirred 6 h with reflux, then stirred over the weekend at 50° C. and then concentrated to low volume in a vacuum. The residue was purified by means of flash chromatography (38 g, 20×2.5 cm) with ethyl acetate/methanol (9:1). 80 mg of the title compound were obtained that were stirred overnight with cyclohexane (20 mL). 406 mg of the target compound were also obtained, which contained still larger amounts of impurity. This mixture was purified once again by flash chromatography (38 g, 20×2.5 cm), in which case cyclohexane/ethyl acetate (4:1) was firstly used as mobile solvent. All fractions that contained the target compound were treated with cyclohexane as above.

Yield: 241 mg (36%), yellowish solid $^1$H-NMR (CDCl$_3$): 1.36-1.48 (m, 2H); 1.63-1.71 (m, 2H); 1.76-1.90 (m, 5H); 1.95-2.01 (m, 2H); 2.03 (s, 6H); 2.13-2.26 (m, 2H); 2.80 (t, 2H, J=7.23 Hz); 7.01 (s, 1H); 7.31 (t, 1H, J=7.3 Hz); 7.19 (t, 1H, J=7.4 Hz); 7.26 (s, 2H); 7.31-7.39 (m, 4H); 7.62 (d, 1H; J=7.8 Hz); 7.95 (br s, 1H).

Step 3

N,N-dimethyl-4'-phenyl-2,3,4,9-tetrahydrospiro[carbazole-1,1'-cyclohexane]-4'-amine (Example No. 1, polar diastereomer and Example No. 2, non-polar diastereomer)

Trifluoromethane sulphonic acid trimethylsilyl ester (755 mg, 617 μL, 3.4 mmol) was added to a suspension of 4-dimethylamino-1-[3-(1H-indol-3-yl)propyl]-4-phenylcyclohexanol (320 mg, 0.85 mmol) in absolute dichloromethane (20 mL), wherein a clear brown solution formed that was stirred for 14 d at room temperature. The reaction solution was then diluted with dichloromethane (10 mL), washed with 1 N sodium carbonate solution (2×10 mL), water and saturated sodium chloride solution (10 mL each), dried with sodium sulphate and concentrated to low volume in a vacuum. The residue (270 mg) was mixed with methanol (30 mL) and stirred overnight at room temperature, wherein a light-coloured solid formed, which was filtered off and washed with a little methanol (2 mL).

Yield: 102 mg (33%), light-coloured solid

The diastereomer mixture obtained was separated by means of preparative HPLC [column: Gemini 5μ C18, 250× 4.6 mm, elutant:CH$_3$CN:H$_2$O:DEA=750:250:1; 1 ml/min].

Example No. 1 (polar diastereomer): retention time: 10.65 min, MH$^+$: 359.3.

Yield: 37 mg

Example No. 2 (non-polar diastereomer): retention time: 18.05 min, MH$^+$: 359.3

Yield: 56 mg

Example No. 3 and Example No. 4

Step 1

4-dimethylamino-1-[3-(5-fluoro-2-triethylsilanyl-1H-indol-3-yl)propyl]-4-phenylcyclohexanol A mixture of 4-dimethylamino-4-phenyl-1-(5-triethylsilanyl-pent-4-inyl)cyclohexanol (525 mg, 1.31 mmol), 4-fluoro-2-iodoaniline (374 mg, 1.58 mmol), [1,3-bis-(2,6-diisopropyl-phenyl)imidazol-2-ylidene]-(3-chloropyridyl) palladium(II)-chloride (PEPPSI, 178 mg, 0.26 mmol) and sodium carbonate (694 mg, 6.6 mmol) was evacuated for 30 min (oil pump). It was then flushed with argon and absolute N,N-dimethylformamide (5 mL, previously flushed for 1 h with argon) was added by syringe via a Schlenk tube. The mixture was stirred for 18 h at 100° C. and changed colour to dark brown during this. The reaction mixture was then concentrated to low volume in a vacuum, the residue taken up several times in toluol (3×10 mL) and concentrated to low volume again in each case, distributed between water and ethyl acetate (20 mL each) and the phases separated again. The aqueous phase was extracted with ethyl acetate (2×30 mL), the combined organic phases were washed with 1 M sodium thiosulphate solution (30 mL) and saturated sodium chloride solution (50 mL), dried with sodium sulphate and concentrated to low volume in a vacuum. The raw product (1.10 g) was purified by means of flash chromatography (50 g, 20×3.0 cm) with chloroform/methanol (97:3).

Yield: 379 mg (57%)

Melting point: 48-50° C.

$^1$H-NMR (DMSO-$d_6$): 0.83-0.99 (m, 15H); 1.23-1.34 (m, 2H); 1.43-1.52 (m, 2H); 1.55-1.64 (m, 6H); 1.72-1.85 (m, 2H); 1.89 (s, 6H); 2.69 (t, 2H, J=7.5 Hz); 3.84 (s, 1H); 6.89 (dt, 1H, J=2.5, 9.3 Hz); 7.22 (dd, 2H, J=2.5, 10.1 Hz); 7.29-7.36 (m, 5H); 10.48 (s, 1H).

$^{13}$C-NMR (DMSO-$d_6$): 3.2 (3C); 7.3 (3C); 25.6; 26.3; 28.4 (2C); 32.5 (2C); 37.7 (2C); 42.7; 58.8; 68.7; 102.7 (d, J=22 Hz); 109.2 (d, J=27 Hz), 112.0; 125.3; 126.0; 126.7 (2C); 127.2 (2C); 128.2 (d, J=9. Hz); 132.5; 135.6; 139.1; 156.4 (d, J=230 Hz).

Step 2

4-dimethylamino-1-[3-(5-fluoro-1H-indol-3-yl)propyl]-4-phenylcyclohexanol

A solution of 4-dimethylamino-1-[3-(5-fluoro-2-triethylsilanyl-1H-indol-3-yl)propyl]-4-phenylcyclohexanol (350 mg, 0.69 mmol) in absolute tetrahydrofuran (25 mL) was mixed with tetra-n-butyl ammonium fluoride trihydrate (868 mg, 2.8 mmol)), stirred 6 h with reflux, then stirred overnight at room temperature. The reaction mixture was then concentrated to low volume in a vacuum and the residue was purified by means of flash chromatography (18 g, 20×2.0 cm) with ethyl acetate/methanol (9:1).

Yield: 217 mg (80%), light beige-coloured solid

Melting point: 199-200° C.

$^1$H-NMR (DMSO-$d_6$): 1.31 (d, 2H, J=13.2 Hz); 1.44-1.48 (m, 2H); 1.61 (t, 2H, J=10.9 Hz); 1.67-1.74 (m, 2H); 1.80 (d, 2H; J=12.7 Hz); 1.90 (s, 6H); 2.18 (d, 2H, J=13.3 Hz); 2.64 (t, 2H, J=7.4 Hz); 3.81 (s, 1H); 6.89 (dt, 1H; J=2.5, 9.2 Hz); 7.18 (d, 1H, J=2.2); 7.23 (dd, 2H, J=2.5, 10.1 Hz); 7.30 (d, 1H, J=4.6 Hz); 7.32-7.36 (m, 4H); 10.82 (s, 1H).

$^{13}$C-NMR (DMSO-$d_6$): 23.6 25.2; 28.5 (2C); 32.6 (2C); 37.7 (2C); 42.4; 58.8; 68.8; 102.9 (d, J=23 Hz); 108.7 (d, J=26 Hz), 112.1 (d, J=9 Hz); 115.2; 124.2; 126.0; 126.7 (2C); 127.2 (2C); 127.4 (d, J=9 Hz); 132.9; 139.1; 156.5 (d, J=229 Hz).

Step 3

6-fluoro-N,N-dimethyl-4'-phenyl-2,3,4,9-tetrahydrospiro[carbazole-1,1'-cyclohexane]-4'-amine (Example No. 3, polar diastereomer and Example No. 4, non-polar diastereomer)

Trifluoromethane sulphonic acid trimethylsilyl ester (822 mg, 671 µL, 3.70 mmol) was added to a suspension of 4-dimethylamino-1-[3-(5-fluoro-1H-indol-3-yl)propyl]-4-phenylcyclohexanol (365 mg, 0.92 mmol) in absolute dichloromethane (50 mL), and stirred for 10 d at room temperature. The reaction solution was then diluted with dichloromethane (10 mL), washed with 1 N sodium carbonate solution (2×10 mL), water and saturated sodium chloride solution (10 mL each), the organic phase dried with sodium sulphate and concentrated to low volume in a vacuum. The residue (249 mg) was mixed with methanol (50 mL) and stirred over the weekend at room temperature, wherein a light-coloured solid formed, which was filtered off and washed with a little methanol (2 mL).

Yield: 74 mg (21%), light-coloured solid

The diastereomer mixture obtained was separated by means of preparative HPLC [column: Gemini 5µ C18, 250× 4.6 mm, elutant:$CH_3CN$:$H_2O$=750:250; 1 ml/min].

Example No. 3 (polar diastereomer): retention time: 10.91 min, MH$^+$: 377.0.

Yield: 8 mg

Example No. 4 (non-polar diastereomer): retention time: 17.51 min, MH$^+$: 377.3

Yield: 50 mg

Example No. 5

Step 1

4-Dimethylamino-4-phenyl-1-[3-(2-triethylsilanyl-1H-pyrrolo[3,2-c]pyridin-3-yl)propyl]-cyclohexanol A suspension of 4-dimethylamino-4-phenyl-1-(5-triethylsilanyl-pent-4-inyl)cyclohexanol (741 mg, 1.85 mmol), 4-amino-3-iodopyridine (488 mg, 2.22 mmol), [1,3-bis-(2,6-diisopropylphenyl)imidazol-2-ylidene]-(3-chloropyridyl)palladium(II)-chloride (PEPPSI, 251 mg, 0.37 mmol) and sodium carbonate (980 mg, 9.25 mmol) in oxygen-free N,N-dimethylformamide (10 mL) was stirred for 20 h at 100° C. The reaction mixture was then concentrated to low volume in a vacuum, the residue repeatedly taken up in toluol (10 mL) and each time concentrated to low volume again in a vacuum, this residue was taken up in ethyl acetate (30 mL) and water (30 mL) and the organic phase washed with water (2×15 mL) and sodium thiosulphate solution (2×25 mL), dried with sodium sulphate and concentrated to low volume in a vacuum. The raw product was purified by means of flash chromatography (38 g, 20×2.5 cm) with ethyl acetate/methanol (4:1).

Yield: 450 mg (44%), yellow foam

Melting point: 89-102° C.

$^1$H-NMR (DMSO-$d_6$): 0.86-0.99 (m, 15H); 1.23-1.34 (m, 2H); 1.45-1.87 (m, 7H); 1.92 (s, 6H); 2.08-2.25 (m, 2H); 2.79 (t, 2H, J=7.4 Hz); 3.87 (s, 1H); 7.18-7.28 (m, 1H); 7.34 (d, 6H, J=4.0 Hz); 8.11 (d, 1H, J=5.8 Hz); 8.84 (s, 1H); 10.86 (s, 1H).

Step 2

4-dimethylamino-4-phenyl-1-[3-(1H-pyrrolo[3,2-c]pyridin-3-yl)propyl]cyclohexanol A solution of 4-dimethylamino-4-phenyl-1-[3-(2-triethylsilanyl-1H-pyrrolo[3,2-c]pyridin-3-yl)propyl]cyclohexanol (410 mg, 0.83 mmol) in anhydrous tetrahydrofuran (25 mL) was mixed with tetra-n-butyl ammonium fluoride trihydrate (1.05 g, 3.32 mmol) and boiled with reflux for 6 h. The reaction mixture was then concentrated to low volume in a vacuum and the raw product purified by means of flash chromatography (38 g, 20×2.5 cm) with ethyl acetate/methanol (2:1). The product was taken up in dichloromethane (40 mL), the solution dried with sodium sulphate and concentrated to low volume in a vacuum.

Yield: 198 mg (63%), yellow foam $^1$H-NMR (DMSO-$d_6$): 1.21-1.36 (m, 2H); 1.42-1.50 (m, 2H); 1.54-1.68 (m, 2H); 1.71-1.80 (m, 2H); 1.94 (s, 6H); 2.10-2.24 (m, 2H); 2.74 (t, 2H, J=7.3 Hz); 3.87 (s, 1H); 7.20-7.30 (m, 2H); 7.32-7.40 (m, 6H); 8.14 (d, 1H, J=5.8 Hz); 8.85 (s, 1H); 11.25 (s, 1H).

Step 3

N,N-dimethyl-4-phenyl-5',7',8',9'-tetrahydrospiro[cyclohexane-1,6'-pyrido[4,3-b]indole]-4-amine (Example No. 5, a diastereomer)

Trifluoromethane sulphonic acid trimethylsilyl ester (409 mg, 334 µL, 1.84 mmol) was added to a solution of 4-dimethylamino-4-phenyl-1-[3-(1H-pyrrolo[3,2-c]pyridin-3-yl)propyl]-cyclohexanol (172 mg, 0.39 mmol) in anhydrous dichloromethane (30 mL) and stirred for 10 d at room temperature. The reaction mixture was then diluted with dichloromethane (10 mL), firstly washed with 1 N sodium carbonate solution (2×10 mL) and then with water and saturated sodium chloride solution (10 mL each), dried with sodium sulphate and concentrated to low volume in a vacuum. The residue (131 mg) was taken up in methanol (15 mL) and stirred overnight at room temperature and then concentrated to low volume in a vacuum.

Yield: 125 mg, brown oil

The raw product obtained was separated by means of preparative HPLC [column: Gemini 5µ C18, 250×21.2 mm, elutant:$CH_3CN:H_2O:DEA=40:60:0.1$; 15 ml/min].

Example No. 5 (a diastereomer): retention time: 9.96 min, $MH^+$: 360.2.

Yield: 17 mg

Example No. 6

Step 1

4-acetidin-1-yl-4-phenyl-1-(5-triethylsilylpent-4-inyl)cyclohexanol

In a heated apparatus in argon a 1.7 M solution of tert-butyl lithium in pentane (20.1 mL, 34.1 mmol) was slowly added in drops to a solution of triethyl-(5-iodopent-1-inyl)silane (5.26 g, 17.1 mmol) in absolute diethyl ether (150 mL) at an inside temperature of −70° C. to -75° C. After 120 min at this temperature a solution of 4-acetidin-1-yl-4-phenylcyclohexane (3.92 g, 17.1 mmol) in absolute diethyl ether (100 mL) was slowly added in drops and subsequently stirred for 30 min. The reaction solution was heated to room temperature and mixed with saturated ammonium chloride solution (100 mL). The phases were separated and the aqueous phase extracted with diethyl ether (3×50 mL). The combined organic phases were washed with saturated sodium chloride solution (50 mL), dried with sodium sulphate and concentrated to low volume in a vacuum. The residue (6.86 g) was purified by means of flash chromatography (400 g, 20×7.5 cm) with cyclohexane/ethyl acetate (2:1).

Yield: 3.50 g (50%), colourless oil $^1$H-NMR (DMSO-$d_6$): 0.55 (q, 6H; J=7.8 Hz); 0.96 (t, 9H, J=7.9 Hz); 1.24-1.92 (m, 14H); 2.19-2.26 (m, 2H); 2.83 (t, 4H, J=6.8 Hz); 3.85 (s, 1H); 7.24-7.42 (m, 5H).

$^{13}$C-NMR (DMSO-$d_6$): 4.0; 7.3; 19.7; 22.3; 29.9; 32.7; 41.2; 46.0; 57.4; 68.6; 80.9; 109.5; 126.2; 126.8; 127.5; 139.7.

LC-MS: m/z: $[M+1]^+$=412.4, $R_t$ 3.3 min.

Step 2

4-(acetidin-1-yl)-4-phenyl-1-[3-(2-(triethylsilyl)-1H-indol-3-yl)propyl]cyclohexanol A mixture of 4-acetidin-1-yl-4-phenyl-1-(5-triethylsilylpent-4-inyl)cyclohexanol (1.20 g, 2.91 mmol), 2-iodoaniline (766 mg, 3.50 mmol), [1,3-bis(2,6-diisopropylphenyl)imidazol-2-ylidene]-3-chloropyridyl-palladium(II)-chloride (PEPPSI, 198 mg, 0.29 mmol) and sodium carbonate (1.54 g, 14.6 mmol) was evacuated for 30 min (oil pump). It was then flushed with argon and absolute N,N-dimethylformamide (5 mL, previously flushed for 1 h with argon) was added by syringe via a Schlenk tube. The batch was stirred for 18 h at 100° C. and changed colour to dark brown during this. The reaction mixture was then concentrated to low volume in a vacuum, the residue taken up several times in toluol (3×30 mL) and concentrated to low volume again in each case. The residue was distributed between water and ethyl acetate (100 mL each), the phases were separated and the aqueous phase extracted with ethyl acetate (2×50 mL). The combined organic phases were washed with 1 Mسs sodium thiosulphate solution and saturated sodium chloride solution (50 mL each), dried with sodium sulphate and concentrated to low volume in a vacuum. The residue (1.59 g) was purified by means of flash chromatography (100 g, 20×4.0 cm) with dichloromethane/methanol (95:5).

Yield: 1.46 g (54%), beige-coloured firm foam

Melting point: 50-52° C.

$^1$H-NMR (DMSO-$d_6$): 0-88-0.92 (m, 6H); 0.94-0.99 (m, 9H); 1.25-1.30 (m, 2H); 1.47-1.52 (m, 2H); 1.57-1.71 (m, 10H); 1.80-1.90 (m, 2H); 2.71-2.76 (m, 2H); 2.78-2.85 (m, 2H); 3.76 (s, 1H); 6.95 (ddd, 1H, J=1.0, 7.0, 7.9 Hz); 7.05 (ddd, 1H, J=1.1; 6.9, 8.1 Hz); 7.24-7.28 (m, 2H); 7.29-7.34 (m, 2H); 7.36-7.39 (m, 2H); 7.51 (d, 1H, J=7.7 Hz); 10.36 (s, 1H).

$^{13}$C-NMR (DMSO-$d_6$): 3.2; 7.4; 15.5; 25.8; 26.4; 26.8; 32.5; 46.0; 57.3; 68.7; 111.2; 117.8; 118.4; 121.1; 125.3; 126.2; 126.8; 127.4; 128.2; 129.8; 138.9.

LC-MS: m/z: $[M+1]^+$=504.4, $R_t$ 3.2 min.

Step 3

4-acetidin-1-yl-1-[3-(1H-indol-3-yl)propyl]-4-phenylcyclohexanol

A solution of 4-(acetidin-1-yl)-4-phenyl-1-[3-(2-(triethylsilyl)-1H-indol-3-yl)propyl]cyclohexanol (740 mg, 1.5 mmol) in absolute tetrahydrofuran (50 mL) was mixed with tetra-n-butyl ammonium fluoride trihydrate (1.86 g, 5.9 mmol) and firstly stirred for 6 h with reflux and then overnight at room temperature. The reaction mixture was then concentrated to low volume in a vacuum and the residue purified by means of flash chromatography (100 g, 20×4.0 cm) with ethyl acetate/methanol (9:1).

Yield: 389 mg (66%), light yellow solid

Melting point: 176-180° C.

$^1$H-NMR (DMSO-$d_6$): 1.26-1.34 (m, 2H); 1.46-1.50 (m, 2H); 1.57-1.77 (m, 8H); 1.81-1.89 (m, 2H); 2.68 (t, 2H, J=7.4 Hz); 2.80-2.88 (m, 4H); 3.76 (s, 1H); 6.97 (t, 1H; J=7.4 Hz); 7.05 (t, 1H, J=7.2 Hz); 7.10 (d, 1H, J=2.1 Hz); 7.26 (t, 1H, J=7.0 Hz); 7.33 (d, 3H, J=8.0 Hz); 7.39 (t, 2H, J=7.5 Hz); 7.51 (d, 1H, J=7.8 Hz); 10.71 (s, 1H).

$^{13}$C-NMR (DMSO-$d_6$): 15.6; 23.7; 25.4; 26.9; 32.7; 42.5; 46.0; 57.3; 68.7; 111.2; 114.9; 117.9; 118.3; 120.6; 122.0; 126.2; 126.8; 127.2; 127.5; 136.2; 139.9.

LC-MS: m/z: $[M+1]^+$=289.3, $R_t$ 2.0 min.

Step 4

4'-(acetidin-1-yl)-4'-phenyl-2,3,4,9-tetrahydrospiro[carbazole-1,1'-cyclohexane]2-hydroxypropane-1,2,3-tricarboxylate (Example No. 6, a diastereomer)

Trifluoromethane sulphonic acid trimethylsilyl ester (771 mg, 629 µL, 3.47 mmol) was added to a solution of 4-acetidin- 1-yl-1-[3-(1H-indol-3-yl)propyl]-4-phenylcyclohexanol (337 mg, 0.87 mmol) in absolute dichloromethane (50 mL). The reaction solution was then washed with 1 N sodium carbonate solution (2×30 mL), water and saturated sodium chloride solution (30 mL each) one after the other, dried with sodium sulphate and concentrated to low volume in a vacuum. The raw product (304 mg) was mixed with methanol (50 mL) and stirred overnight at room temperature, wherein a light-coloured solid was formed. The solvent was decanted off, the filtrate concentrated to low volume in a vacuum and the residue repeatedly mixed with methanol (3×20 mL) and decanted in each case. The methanol-insoluble batches were dried in a vacuum. For purification the product with separated with citric acid as citrate.

Example No. 6
Yield: 100 mg, beige-coloured foam
LC-MS: m/z: $[M+H]^+=371.3$, $R_t=4.1$ min.

Example No. 7 and Example No. 8

Step 1

1-butyl-N,N-diethyl-4-(5-triethylsilyl)pent-4-inylidene)cyclohexanamine

In a heated apparatus a 2.5 M solution of n-butyl lithium in hexane (3.1 mL, 7.7 mmol) was slowly added in drops to a suspension of triphenyl-(5-trimethylsilylpent-4-inyl)phosphonium iodide (4.40 g, 7.7 mmol) in absolute tetrahydrofuran (200 mL) at −78° C. and in argon. After stirring for 30 min at −40° C., it was cooled again to −78° C. and at this temperature a solution of 4-butyl-4-(dimethylamino)cyclohexanone (2.20 g, 10.1 mmol) in absolute tetrahydrofuran (20 mL) was added slowly in drops and subsequently stirred for 30 min. The reaction solution was heated to room temperature and mixed with saturated ammonium chloride solution (100 mL). The pH (7) was then adjusted with 4N sodium hydroxide solution to 9-10. The phases were separated, the aqueous phase extracted with diethyl ether (3×50 mL) and the combined organic phases were washed with saturated sodium chloride solution (50 mL), dried with sodium sulphate and concentrated to low volume in a vacuum. The residue (5.40 g) was purified by means of flash chromatography (200 g, 20×5.7 cm) with cyclohexane/ethyl acetate (1:1).

Yield: 1.83 g (66%), light yellow oil
$^1$H NMR (DMSO-$d_6$): 0.52 (q, J=7.8 Hz, 6H); 0.87 (t, J=7.0 Hz, 3H); 0.93 (t, J=7.8 Hz, 9H); 1.04-1.40 (m, 12H); 1.60-1.70 (m, 2H); 2.07-2.14 (m, 2H); 2.16 (s, 6H); 2.19-2.29 (m, 2H); 5.07 (t, J=6.9 Hz, 1H).
$^{13}$C-NMR (DMSO-$d_6$): 4.0; 7.3; 14.0; 22.9; 23.0; 23.2; 25.7; 25.9; 30.2; 31.2; 32.3; 32.8; 37.0; 56.1; 81.5; 109.5; 119.2; 139.7.
LC-MS: m/z: $[M+1]^+=362.4$, $R_t$ 3.8 min.

Step 2

1-butyl-N,N-dimethyl-4-[3-(2-(triethylsilyl)-1H-indol-3-yl)propylidene]cyclohexanamine A mixture of 1-butyl-N,N-dimethyl-4-(5-triethylsilyl) pent-4-inylidene)cyclohexanamine (1.80 g, 5.0 mmol), 2-iodoaniline (1.31 g, 6.0 mmol), [1,3-bis-(2,6-diisopropylphenyl)-imidazol-2-ylidene]-(3-chloropyridyl)palladium(II)-chloride (PEPPSI, 340 mg, 0.5 mmol) and sodium carbonate (2.65 g, 25 mmol) was evacuated for 30 min (oil pump). It was then flushed with argon and absolute N,N-dimethylformamide (5 mL, previously flushed for 1 h with argon) was added by syringe via a Schlenk tube. The reaction mixture was stirred for 18 h at 100° C. and changed colour to dark brown during this. The reaction mixture was then concentrated to low volume in a vacuum, the residue taken up several times in toluol (3×50 mL) and concentrated to low volume again in each case. The residue was distributed between water and ethyl acetate (100 mL each), the phases were separated and the aqueous phase extracted with ethyl acetate (2×50 mL). The combined organic phases were washed with 1 M sodium thiosulphate solution and saturated sodium chloride solution (50 mL each), dried with sodium sulphate and concentrated to low volume in a vacuum. The raw product (2.33 g) was purified by means of flash chromatography (100 g, 20×4.0 cm) with dichloromethane/methanol (95:5).

Yield: 1.27 g (56%), viscous brown oil
$^1$H-NMR (DMSO-$d_6$): 0.85-0.95 (m, 18H); 1.03-1.17 (m, 4H); 1.19-1.35 (m, 4H); 1.44-1.65 (m, 2H); 1.77-1.95 (m, 2H); 1.98-2.09 (m, 2H); 2.16 (m, 6H); 2.22-2.30 (m, 2H); 2.73-2.78 (m, 2H); 5.18 (br s, 1H); 6.95 (ddd, J=7.9, 7.0, 1.0 Hz, 1H); 7.04 (ddd, J=8.1, 6.9, 1.1 Hz, 1H); 7.35 (d, J=8.1 Hz, 1H); 7.49 (d, J=7.8 Hz, 1H); 10.38 (s, 1H).
$^{13}$C-NMR (DMSO-$d_6$): 3.3; 7.3; 13.9; 22.9; 23.1; 25.7; 26.4; 29.5; 30.1; 31.2; 32.1; 37.0; 54.8; 111.2; 117.8; 118.4; 121.1; 124.3; 128.1; 130.0; 139.0.
LC-MS: m/z: $[M+1]^+=453.4$, $R_t$ 4.0 min.

Step 3

4-[3-(1H-indol-3-yl)propylidene]-1-butyl-N,N-dimethylcyclohexanamine

A solution of 1-butyl-N,N-dimethyl-4-[3-(2-(triethylsilyl)-1H-indol-3-yl)propylidene]cyclohexanamine (1.20 g, 2.7 mmol) in absolute tetrahydrofuran (100 mL) was mixed with tetra-n-butyl ammonium fluoride trihydrate (3.34 g, 10.6 mmol), stirred 7 h with reflux and then 18 h at room temperature. The reaction mixture was concentrated to low volume in a vacuum and the residue purified by means of flash chromatography (100 g, 20×4.0 cm) with dichloromethane/methanol (9:1). 517 mg of the target compound were obtained, but were present in the form of a salt (presumably hydrochloride). This was taken up in saturated potassium carbon solution (50 mL) and the solution extracted with dichloromethane (3×30 mL). The combined organic phases were dried with sodium sulphate and concentrated to low volume in a vacuum, as a result of which 457 mg of pure target compound were obtained. In addition, 379 mg of target compound were obtained that also contained a tetrabutyl ammonium salt as impurity. However, renewed purification by means of flash chromatography (18 g, 20×2.0 cm) with dichloromethane/methanol (9:1) only resulted in a further 32 mg of pure target compound.

Yield: 489 mg (54%), viscous brown oil
$^1$H-NMR (DMSO-$d_6$): 0.87 (t, J=7.2 Hz, 3H); 1.00-1.15 (m, 2H); 1.18-1.31 (m, 6H); 1.48-1.64 (m, 2H); 1.82-1.89 (m, 1H); 1.99-2.10 (m, 2H); 2.13 (s, 6H); 2.18-2.27 (m, 1H); 2.29-2.37 (m, 2H); 2.69 (t, J=7.4 Hz, 2H); 5.14 (t, J=6.8 Hz, 1H); 6.95 (t, J=7.4 Hz, 1H); 7.04 (t, J=7.5 Hz, 1H); 7.08 (s, 1H); 7.31 (d, J=7.8 Hz, 1H); 7.49 (d, J=7.7 Hz, 1H); 10.70 (s, 1H).
$^{13}$C-NMR (DMSO-$d_6$): 14.0; 22.9; 23.2; 25.3; 25.8; 27.7; 30.2; 31.2; 32.0; 32.8; 37.0; 56.1; 111.2; 114.3; 117.9; 118.2; 120.6; 120.8; 122.1; 127.2; 136.2; 138.5.
LC-MS: m/z: $[M+1]^+=339.3$, $R_t$ 3.1 min.

Step 4

N,N-dimethyl-N-(4-butyl-2',3',4',9'-tetrahydro-1H-spiro[cyclohexane-1,1'-carbazole]-4-yl)amine (Example No. 7, polar diastereomer and Example No. 8, non-polar diastereomer)

p-toluol sulphonic acid (323 mg, 1.7 mmol) was added to a solution 4-[3-(1H-indol-3-yl)propylidene]-1-butyl-N,N-dimethylcyclohexanamine (289 mg, 0.85 mmol) in absolute toluol (10 mL) and stirred for 18 h at 100° C. The reaction solution was then diluted with dichloromethane (30 mL) and washed with 1 N sodium carbonate solution (2×30 mL), water and saturated sodium chloride solution (30 mL each) one after the other, dried with sodium sulphate and concentrated to low volume in a vacuum. The raw product (272 mg) was mixed with methanol (100 mL) and stirred overnight at room temperature, during which very little precipitate was formed (light-coloured solid). The $^1$H-NMR spectrum and the LC-MS data showed that this concerned two isomers, and the $^1$H-NMR spectrum revealed that these were present in a ratio of approx. 1:1 and olefin side-products were present at most in very small quantity. The reaction solution was concentrated to low volume in a vacuum (259 mg, 90%). The diastereomer mixture was separated by preparative HPLC.

Example No. 7: polar diastereomer (61 mg, 21%)

LC-MS: m/z: [M+1]$^+$=339.3, R$_t$ 4.4 min.

Example No. 8: non-polar diastereomer (86 mg, 30%)

LC-MS: m/z: [M+1]$^+$=339.3, R$_t$ 4.7 min.

Example No. 9 and Example No. 10

Step 1

4-benzyl-4-dimethylamino-1-(5-(triethylsilyl)pent-4-inyl)cyclohexanol

In a heated apparatus under argon at −75° C. a 1.7 M solution of tert-butyl lithium (23.3 mL, 39.6 mmol) in pentane was added by cannula directly to a solution of triethyl-(5-iodopent-1-inyl)silane (6.10 g, 19.8 mmol) in anhydrous diethyl ether (150 mL), so that the inside temperature was held between −70° C. and −75° C. After stirring for 120 min a solution of 4-benzyl-4-dimethylaminocyclohexanone (4.58 g, 19.8 mmol) in anhydrous diethyl ether (150 mL) was slowly added in drops, subsequently stirred for 30 min, and the reaction solution was then heated to room temperature. The reaction mixture was then mixed with saturated ammonium chloride solution (100 mL), the phases were separated and the aqueous phase extracted with diethyl ether (3×50 mL). The combined organic phases were washed with sodium chloride solution (50 mL), dried with sodium sulphate and concentrated to low volume in a vacuum. The raw product was purified by means of flash chromatography (400 g, 20×7.5 cm) with cyclohexane/ethyl acetate (4:1).

Yield: 3.90 g (48%), yellow oil (contains approx. 25% 4-benzyl-1-tert-butyl-4-dimethylamino-cyclohexanol)

$^1$H-NMR (DMSO-d$_6$): 0.47-0.55 (m, 6H); 0.93 (t, 9H, J=7.9 Hz); 1.10-1.14 (m, 2H); 1.28-1.33 (m, 2H); 1.37-1.52 (m, 8H); 2.15 (t, 2H, J=6.8 Hz); 2.22 (s, 6H); 2.54-2.56 (m, 2H); 3.45 (s, 1H); 7.11-7.18 (m, 3H); 7.22-7.27 (m, 2H).

This is a uniform diastereoisomer.

LC-MS: m/z: [M+H]$^+$=414.4, R$_t$=3.3 min.

Step 2

4-benzyl-4-dimethylamino-1-[3-(2-(triethylsilyl)-1H-indol-3-yl)propyl]cyclohexanol A mixture of 4-benzyl-4-dimethylamino-1-(5-triethylsilyl)pent-4-inyl)cyclohexanol (900 mg, 1.64 mmol), 2-iodoaniline (431 mg, 1.97 mmol), [1,3-bis-(2,6-diisopropylphenyl)imidazol-2-ylidene]-(3-chloropyridyl)palladium(II)-chloride (PEPPSI, 109 mg, 0.16 mmol) and sodium carbonate (869 mg, 8.20 mmol) was degasified, mixed with oxygen-free N,N-dimethylformamide (10 mL) in argon and stirred for 18 h at 100° C. The reaction mixture was then concentrated to low volume in a vacuum, the residue repeatedly taken up in toluol (10 mL) and concentrated to low volume in a vacuum again each time. This residue was distributed between ethyl acetate (30 mL) and water (30 mL), the organic phase was washed with water (2×15 mL) and sodium thiosulphate solution (2×15 mL), dried with sodium sulphate and concentrated to low volume in a vacuum. The raw product was purified by means of flash chromatography (100 g, 20×4.0 cm) with dichloromethane/methanol (95:5).

Yield: 707 mg (85%), brown oil $^1$H-NMR (DMSO-d$_6$): 0.83-0.88 (m, 6H); 0.90-0.95 (m, 9H); 1.07-1.11 (m, 2H); 1.30-1.49 (m, 8H); 1.50-1.60 (m, 2H); 2.19 (s, 6H); 2.54 (s, 2H); 2.66 (t, 2H, J=7.9 Hz); 3.38 (s, 1H); 6.92 (ddd, 1H, J=1.0, 7.0, 7.9 Hz); 7.03 (ddd, 1H, J=1.1, 6.9, 8.1 Hz); 7.10-7.16 (m, 3H); 7.23 (t, 2H, J=7.3 Hz); 7.34 (d, 1H, J=8.1 Hz); 7.45 (d, 1H, J=8.0 Hz); 10.33 (s, 1H).

$^{13}$C-NMR (DMSO-d$_6$): 3.8; 7.8; 26.4; 26.9; 27.7; 31.7; 36.7; 37.2; 44.9; 57.9; 69.3; 111.9; 118.5; 118.8; 121.7; 125.8; 126.0; 128.2; 128.7; 130.4; 131.1; 139.4; 139.7

LC-MS: m/z: [M+H]$^+$=505.5, R$_t$=3.4 min.

Step 3

1-(3-(1H-indol-3-yl)propyl)-4-benzyl-4-(dimethylamino)cyclohexanol

A solution of 4-benzyl-4-dimethylamino-1-[3-(2-(triethylsilyl)-1H-indol-3-yl)propyl]cyclohexanol (2.50 g, 4.95 mmol) in anhydrous tetrahydrofuran (25 mL) was mixed with tetra-n-butyl ammonium fluoride trihydrate (6.25 g, 19.8 mmol), boiled with reflux for 7 h and then stirred overnight at room temperature. Since the conversion was not yet complete, the reaction mixture was boiled with reflux for a further 7 h and then stirred over the weekend at room temperature. The reaction mixture was concentrated to low volume in a vacuum and the residue purified by means of flash chromatography (400 g, 20×7.5 cm) with dichloromethane/methanol (95:5+1% conc. aqueous ammonia).

Yield: 1.32 g (68%), white solid

Melting point: 202-215° C.

$^1$H-NMR (DMSO-d$_6$): 1.12 (d, 2H, J=10.0 Hz); 1.27-1.33 (m, 2H); 1.37-1.51 (m, 6H); 1.55-1.67 (m, 2H); 2.20 (s, 6H); 2.54 (s, 2H); 2.60 (t, 2H, J=7.4 Hz); 3.39 (s, 1H); 6.90-6.96 (m, 1H); 7.00-7.06 (m, 2H); 7.09-7.18 (m, 3H); 7.20-7.27 (m, 2H); 7.30 (d, 1H, J=8.0 Hz); 7.46 (dd, 1H, J=0.5, 7.8 Hz); 10.69 (s, 1H).

$^{13}$C-NMR (DMSO-d$_6$): 23.8; 25.4; 27.2; 31.5; 36.1; 36.7; 44.3; 57.2; 68.4; 111.2; 114.9; 117.9; 118.3; 120.6; 122.0; 125.3; 127.2; 127.6; 130.6; 136.2; 139.3.

LC-MS: m/z: [M+H]$^+$=391.3, R$_t$=2.1 min.

Step 4

4'-benzyl-N,N-dimethyl-2,3,4,9-tetrahydrospiro[carbazole-1,1'-cyclohexane]-4'-amine (Example No. 9, non-polar diastereomer and Example No. 10, polar diastereomer)

Trifluoromethane sulphonic acid trimethylsilyl ester (1.30 mL, 1.59 g, 7.16 mmol) was added to a solution of 1-(3-(1H-indol-3-yl)propyl)-4-benzyl-4-(dimethylamino)cyclohexanol (700 mg, 1.79 mmol) in anhydrous dichloromethane (30 mL) and stirred for 2 d at room temperature. The reaction mixture was then diluted with dichloromethane (10 mL), and firstly washed with 1 N sodium carbonate solution (2×10 mL), then with water and saturated sodium chloride solution (10 mL each), dried with sodium sulphate and concentrated to low volume in a vacuum. The residue was taken up in methanol (30 mL), stirred over the weekend at room temperature and decanted off from the separated precipitate (fraction 1). The solution was concentrated to low volume, the residue taken up in methanol (2×10 mL) and decanted off from the precipitated solid again in each case. The remaining solution was concentrated to low volume in a vacuum, as a result of which fraction 2 was obtained.

Example No. 9: fraction 2 (methanol-soluble fraction, non-polar diastereomer) was purified by preparative HPLC.

Yield: 510 mg (75%), brown oil
LC-MS: m/z: [M+1]$^+$=373.3, $R_t$ 4.1

Example No. 10: fraction 1 (methanol-insoluble fraction, polar diastereomer) was purified by preparative HPLC.

Yield: 135 mg (20%), beige-coloured solid
Melting point: 174-186° C.
LC-MS: m/z: [M+1]$^+$=373.3, $R_t$ 3.8
LC-MS: m/z: [M+1]$^+$=373.3, $R_t$ 3.8
$^1$H-NMR (DMSO-d$_6$): 1.14-1.41 (m, 6H); 1.55-1.64 (m, 2H); 1.65-1.74 (m, 2H); 2.09-2.22 (m, 2H); 2.36 (s, 6H); 2.63 (s, 2H); 6.83-6.89 (m, 1H); 6.92-6.98 (m, 1H); 7.16-7.32 (m, 7H); 10.42 (s, 1H).
$^{13}$C-NMR (DMSO-d$_6$): 19.2; 21.0; 27.0; 30.6; 30.7; 33.6; 36.4; 37.0; 56.9; 107.4; 110.9; 117.1; 117.7; 119.5; 125.6; 126.9; 127.7; 130.5; 135.9; 139.2; 142.3.

Example No. 11 and Example No. 12

Step 1

4-dimethylamino-4-(3-fluorophenyl)-1-(5-(triethylsilyl)pent-4-inyl)cyclohexanol

In a heated apparatus a 1.7 M solution of tert-butyl lithium (27.5 mL, 46.8 mmol) in pentane was injected directly by cannula into a solution of ? (7.20 g, 23.4 mmol) in anhydrous diethyl ether (150 mL) at –75° C. with argon, so that the inside temperature was held between –70° C. and –75° C. After stirring for 120 min a solution of 4-dimethylamino-4-(3-fluorophenyl)-cyclohexanone (5.51 g, 23.4 mmol) in anhydrous diethyl ether (150 mL) was slowly added in drops, subsequently stirred for 30 min, and the reaction solution was then heated to room temperature. The reaction mixture was then mixed with saturated ammonium chloride solution (100 mL), the phases were separated, the aqueous phase extracted with diethyl ether (3×50 mL). The combined organic phases were washed with sodium chloride solution (50 mL), dried with sodium sulphate and concentrated to low volume in a vacuum. The raw product was purified by means of flash chromatography (400 g, 20×7.5 cm) with cyclohexane/ethyl acetate (3:1).

Yield: 3.46 g (35%), yellow oil
$^1$H-NMR (DMSO-d$_6$): 0.54 (q, 6H, J=7.9, 8.1 Hz); 0.95 (t, 9H, J=7.9 Hz); 1.25-1.33 (m, 2H); 1.44-1.65 (m, 6H); 1.81 (t, 2H, J=12.5 Hz); 1.92 (s, 6H); 2.11-2.24 (m, 4H); 3.90 (s, 1H); 7.02-7.17 (m, 3H); 7.38 (dd, 1H, J=14.5, 7.9 Hz).

This is a uniform diastereoisomer.

Step 2

4-dimethylamino-4-(3-fluorophenyl)-1-[3-(2-(triethylsilyl)-1H-indol-3-yl)propyl]cyclohexanol A mixture of 4-dimethylamino-4-(3-fluorophenyl)-1-(5-(triethylsilyl)pent-4-inyl)cyclohexanol (970 mg, 2.32 mmol), 2-iodoaniline (609 mg, 2.78 mmol), [1,3-bis-(2,6-diisopropylphenyl)imidazol-2-ylidene]-(3-chloropyridyl)palladium (II)-chloride (PEPPSI, 156 mg, 0.23 mmol) and sodium carbonate (1.23 g, 11.6 mmol) was degasified, mixed with oxygen-free N,N-dimethylformamide (10 mL) in argon and stirred for 7 h at 100° C. The reaction mixture was then concentrated to low volume in a vacuum, the residue repeatedly taken up in toluol (10 mL) and concentrated to low volume in a vacuum again each time. This residue was distributed between ethyl acetate (30 mL) and water (30 mL), the organic phase was washed with water (2×15 mL) and sodium thiosulphate solution (2×15 mL), dried with sodium sulphate and concentrated to low volume in a vacuum. The raw product was purified by means of flash chromatography (100 g, 20×4.0 cm) with cyclohexane/ethyl acetate (4:1).

Yield: 1.11 mg (94%), yellow oil
$^1$H-NMR (DMSO-d$_6$): 0.83-1.00 (m, 15H); 1.22-1.33 (m, 2H); 1.45-1.82 (m, 8H); 1.89 (s, 6H); 2.10-2.23 (m, 2H); 2.72 (t, 2H, J=7.7 Hz); 3.84 (s, 1H); 6.94 (ddd, 1H, J=1.0, 7.0, 7.9 Hz); 7.01-7.16 (m, 4H); 7.33-7.40 (m, 2H); 7.50 (d, 1H, J=7.8 Hz); 10.37 (s, 1H).
$^{13}$C-NMR (DMSO-d$_6$): 3.3; 7.4; 25.8; 26.3; 26.4; 28.4; 32.4; 37.7; 43.0; 54.8; 58.8; 68.6; 111.2; 112.8 (d, J=21 Hz); 113.5 (d, J=21 Hz); 117.8; 118.3; 121.1; 122.8; 125.3; 128.2; 128.8 (d, J=8 Hz); 129.7; 138.9; 142.5 (d, J=5 Hz); 161.9 (d, J=242 Hz).
LC-MS: m/z: [M+H]$^+$=509.4, $R_t$=3.2 min.

Step 3

1-(3-(H-indol-3-yl)propyl)-4-(dimethylamino)-4-(3-fluorophenyl)cyclohexanol

A solution of 4-dimethylamino-4-(3-fluorophenyl)-1-[3-(2-(triethylsilyl)-1H-indol-3-yl)propyl]cyclohexanol (1.11 g, 2.18 mmol) in anhydrous tetrahydrofuran (25 mL) was mixed with tetra-n-butyl ammonium fluoride trihydrate (2.75 g, 8.72 mmol) and boiled with reflux for 3 h. The reaction mixture was then concentrated to low volume in a vacuum and the raw product was purified by means of flash chromatography (100 g, 20×4.0 cm) with dichloromethane/methanol (93:7).

Yield: 550 mg (64%), white solid
Melting point: 196-204° C.
$^1$H-NMR (DMSO-d$_6$): 1.26-1.36 (m, 2H); 1.42-1.50 (m, 2H); 1.54-1.65 (m, 2H); 1.67-1.83 (m, 4H); 1.90 (s, 6H); 2.12-2.23 (m, 2H); 2.67 (t, 2H, J=7.3 Hz); 3.84 (s, 1H); 6.93-6.99 (m, 1H); 7.02-7.18 (m, 5H); 7.31-7.34 (m, 1H); 7.38 (d, 1H, J=6.9 Hz); 7.50 (d, 1H, J=7.7 Hz); 10.72 (s, 1H).
$^{13}$C-NMR (DMSO-d$_6$): 23.8; 25.4; 28.5; 32.5; 37.7; 42.7; 58.8; 68.7; 111.2; 112.8 (d, J=21 Hz); 113.5 (d, J=21 Hz); 114.9; 117.9; 118.3; 120.7; 122.0; 122.8; 127.2; 128.8 (d, J=8 Hz); 136.3; 142.5; 161.9 (d, J=242 Hz).
LC-MS: m/z: [M+H]$^+$=395.3, $R_t$=1.90 min.

Step 4

4'-(3-fluorophenyl)-N,N-dimethyl-N-2,3,4,9-tetrahydrospiro[carbazole-1,1'-cyclohexane]-4'-amine (Example No. 11, polar diastereomer and Example No. 12, non-polar diastereomer)

Trifluoromethane sulphonic acid trimethylsilyl ester (2.25 g, 1.84 mL, 10.1 mmol) was added to a solution of 1-(3-(1H-indol-3-yl)propyl)-4-(dimethylamino)-4-(3-fluorophenyl)-cyclohexanol (1.00 g, 2.53 mmol) in anhydrous dichloromethane (30 mL) and stirred for 8 d at room temperature. The reaction mixture was then diluted with dichloromethane (30 mL), firstly washed with 1 N sodium carbonate solution (2×30 mL), then with water and saturated sodium chloride solution (30 mL each), dried with sodium sulphate and concentrated to low volume in a vacuum. The residue was taken up in methanol (15 mL), stirred overnight at room temperature and decanted off from the separated precipitate. The solution was concentrated to low volume in a vacuum and the residue was taken up in methanol (2×10 mL) and decanted off again from the separated precipitate. The solid is a mixture of two diastereomers in a ratio of 2:1. These (432 mg) are separated by preparative HPLC.

Example No. 11: (polar diastereomer)
Yield: 66 mg (7%)
Melting point: 170-182° C.
$^1$H-NMR (DMSO-$d_6$), characteristic signals: 1.92 (s, 2H, NMe$_2$), 2.06 (s, 4H, NMe$_2$); 10.17 (s, 0.33H, indole-NH), 10.55 (s, 0.67H, indole-NH).
LC-MS: m/z: [M+H]$^+$=377.3, R$_t$=3.7 min.
Example No. 12: (non-polar diastereomer)
Yield: 156 mg (16%)
LC-MS: m/z: [M+H]$^+$=377.3, R$_t$=3.9 min.

Example No. 13 and Example No. 14

Step 1

4-dimethylamino-4-(thiophen-2-yl)-1-(5-(triethylsilyl)pent-4-inyl)cyclohexanol In a heated apparatus a 1.7 M solution of tert-butyl lithium in pentane (22.3 mL, 37.9 mmol) was slowly added in drops to a solution of triethyl-(5-iodopent-1-inyl)silane (5.64 g, 18.9 mmol) in absolute diethyl ether (50 mL) at an inside temperature of −70° C. to −75° C. with argon. After 120 min at this temperature a solution of 4-dimethylamino-4-(thiophen-2-yl)cyclohexane (4.22 g, 18.9 mmol) in absolute diethyl ether (100 mL) was slowly added in drops and subsequently stirred for 30 min. The reaction solution was then heated to room temperature and mixed with saturated ammonium chloride solution (100 mL). The phases were separated and the aqueous phase extracted with diethyl ether (3×50 mL). The combined organic phases were washed with saturated sodium chloride solution (50 mL), dried with sodium sulphate and concentrated to low volume in a vacuum. The residue (7.02 g) was purified by means of flash chromatography (100 g, 20×4.0 cm) with cyclohexane /ethyl acetate (2:1).
Yield: 3.00 g (39%), yellow viscous oil
$^1$H-NMR (DMSO-$d_6$): 0.54 (q, 6H; J=7.9 Hz); 0.95 (t, 9H, J=7.8 Hz); 1.23-1.66 (m, 8H); 1.84-1.96 (m, 2H); 1.99 (s, 6H); 2.10-2.11 (m, 2H); 2.22 (t, 2H; J=6.3 Hz); 3.94 (s, 1H); 6.91 (d, 1H; J=3.0 Hz); 7.04 (dd, 1H, J=1.2, 4.9 Hz); 7.38 (d, 1H; J=4.9 Hz).
$^{13}$C-NMR (DMSO-$d_6$): 4.0; 7.3; 19.7; 22.3; 31.0; 32.4; 37.7; 41.7; 58.4; 68.5; 80.9; 109.4; 123.1; 123.9; 126.1; 144.8.
LC-MS: m/z: [M+1]$^+$=406.7, R$_t$ 3.2 min.

Step 2

4-dimethylamino-4-(thiophen-2-yl)-1-(3-(2-(triethylsilyl)-1H-indol-3-yl)propyl)cyclohexanol A mixture of 4-dimethylamino-4-(thiophen-2-yl)-1-(5-(triethylsilyl)pent-4-inyl)cyclohexanol (3.00 g, 7.4 mmol), 2-iodoaniline (1.94 g, 8.9 mmol), [1,3-bis-(2,6-diisopropylphenyl)-imidazol-2-ylidene]-(3-chloropyridyl)palladium (II)-chloride (PEPPSI, 503 mg, 0.74 mmol) and sodium carbonate (3.92 g, 37 mmol) was evacuated for 30 min (oil pump). It was then flushed with argon and absolute N,N-dimethylformamide (10 mL, previously flushed for 1 h with argon) was added by syringe via a Schlenk tube. The reaction mixture was stirred for 18 h at 100° C. and changed colour to dark brown during this. The reaction mixture was then concentrated to low volume in a vacuum, the residue taken up several times in toluol (3×30 mL) and concentrated to low volume again in each case. The residue was distributed between water and ethyl acetate (100 mL each), the phases were separated and the aqueous phase extracted with ethyl acetate (2×50 mL). The combined organic phases were washed with 1 M sodium thiosulphate solution and saturated sodium chloride solution (50 mL each), dried with sodium sulphate and concentrated to low volume in a vacuum. The residue (4.40 g) was purified by means of flash chromatography (200 g, 20×5.7 cm) with dichloromethane/methanol (95:5).
Yield: 2.20 g (62%), brown viscous oil
$^1$H-NMR (DMSO-$d_6$): 0.89-0.99 (m, 15H); 1.26-1.71 (m, 8H); 1.81-1.93 (m, 2H); 1.96 (s, 6H); 2.01-2.10 (m, 2H); 2.72 (t, 2H, J=7.5 Hz); 3.88 (s, 1H); 6.89-6.97 (m, 2H); 7.01-7.07 (m, 2H); 7.35-7.38 (m, 2H); 7.50 (d, 1H; J=7.8 Hz); 10.37 (s, 1H).
$^{13}$C-NMR (DMSO-$d_6$): 3.2; 7.4; 25.3; 25.8; 26.4; 30.9; 32.2; 37.6; 43.4; 58.3; 68.6; 111.2; 117.8; 118.3; 121.0; 123.0; 123.9; 125.2; 126.1; 128.2; 129.8; 138.9; 144.9.
LC-MS: m/z: [M+1]$^+$=497.8, R$_t$ 3.1 min.

Step 3

1-(3-(H-indol-3-yl)propyl)-4-(dimethylamino)-4-(thiophen-2-yl)cyclohexanol

A solution of 4-dimethylamino-4-(thiophen-2-yl)-1(3-(2-(triethylsilyl)-1H-indol-3-yl)propyl)cyclohexanol (2.30 g, 4.6 mmol) in absolute tetrahydrofuran (100 mL) was mixed with tetra-n-butyl ammonium fluoride trihydrate (5.68 g, 20 mmol), stirred with reflux for 4 h and then stirred overnight at room temperature. Since the conversion was not yet complete, the reaction mixture was stirred with reflux for a further 6 h. The reaction mixture was concentrated to low volume in a vacuum and the residue purified by means of flash chromatography (100 g, 20×4.0 cm) with dichloromethane/methanol (95:5).
Yield: 1.56 g (89%), light-coloured solid
Melting point: 163-165° C.
$^1$H-NMR (DMSO-$d_6$): 1.26-1.37 (m, 2H); 1.41-1.47 (m, 2H); 1.54-1.64 (m, 2H); 1.69-1.77 (m, 2H); 1.85-1.94 (m, 2H); 1.98 (s, 6H); 2.02-2.10 (m, 2H); 2.67 (t, 2H, J=7.4 Hz); 3.88 (s, 1H); 6.90 (dd, 1H, J=1.1, 3.6 Hz); 7.00 (ddd, 1H, J=1.1; 7.0; 8.0 Hz); 7.02-7.05 (m, 2H); 7.09 (d, 1H, J=2.2 Hz);

7.32 (td, 1H, J=0.9; 8.1 Hz); 7.38 (dd, 1H, J=1.1; 5.1 Hz); 7.50 (d, 1H, J=7.9 Hz); 10.71 (s, 1H).

$^{13}$C-NMR (DMSO-d$_6$): 23.7; 25.4; 31.0; 32.4; 37.7; 43.0; 58.3; 68.6; 111.2; 114.9; 117.9; 118.3; 120.6; 122.0; 123.0; 123.9; 126.1; 127.2; 136.2; 145.0.

LC-MS: m/z: [M+1]$^+$=383.6, R$_t$ 1.9 min.

Step 4

N,N-dimethyl-4'-(thiophen2-yl)-2,3,4,9-tetrahydrospiro[carbazole-1,1'-cyclohexane]-4'-amine (Example No. 13, polar diastereomer and Example No. 14, non-polar diastereomer)

Trifluoromethane sulphonic acid trimethylsilyl ester (1.95 g, 159 mL, 8.8 mmol) in absolute 1,2 dichloroethane (100 mL) was added to a suspension of 1-(3-(1H-indol-3-yl)propyl)-4-(dimethylamino)-4-(thiophen-2-yl)cyclohexanol (800 mg, 2.1 mmol), and a clear solution formed. The solution was stirred for 6 h at 50° C. and then overnight at room temperature. The reaction solution was washed with 1 N sodium carbonate solution (2×30 mL), water and saturated sodium chloride solution (30 mL each) one after the other, dried with sodium sulphate and concentrated to low volume in a vacuum. The raw product (720 mg) was mixed with methanol (100 mL) and stirred overnight at room temperature, during which a light-coloured solid was formed. This was filtered off, washed with methanol (10 mL) and dried in a vacuum, as a result of which a diastereomer mixture in a ratio of 5:1 was obtained (290 mg, (38%)). This was separated by preparative HPLC.

Example No. 13: (polar diastereomer)
Yield: 37 mg (5%)
LC-MS: m/z: [M+1]$^+$=365.2, R$_t$ 3.5
Example No. 14: (non-polar diastereomer)
Yield: 174 mg (23%).
LC-MS: m/z: [M+1]$^+$=365.2, R$_t$ 3.8.

Example No. 15

Step 1

2-((S)-3-bromo-2-methylpropoxy)tetrahydropyrane

A solution of (S)-3-bromo-2-methylpropan-1-ol (7.30 g, 5 mL, 47.7 mmol) in anhydrous dichloromethane (100 mL) was mixed with 3,4-dihydro-2H-pyrane (4.63 g, 5.02 mL, 55 mmol) and pyridinium tosylate (50 mg) with ice cooling and then stirred for 1 h at room temperature. The reaction mixture was then washed with 5% sodium hydrogencarbonate solution and water (3×30 mL each). The combined organic phases were dried with sodium sulphate and concentrated to low volume in a vacuum.

Yield: 11.1 g (98%), colourless oil
$^1$H-NMR (DMSO-d$_6$): 0.96 (d, 1.5H, J=6.7 Hz); 0.97 (d, 1.5H, J=6.7 Hz); 1.40-1.80 (m, 6H); 1.97-2.13 (m, 1H); 3.22-3.29 (m, 1H); 3.39-3.48 (m, 1H); 3.51-3.60 (m, 3H); 3.69-3.79 (m, 1H); 4.53-4.58 (m, 1H).

This is a diastereoisomer mixture.

Step 2

Triethyl-[(R)-4-methyl-5-(tetrahydro-2H-pyran-2-yloxy)pent-1-inyl]silane

A solution of triethylsilyl acetylene (6.25 g, 8 mL, 44.7 mmol) in anhydrous tetrahydrofuran (150 mL) was mixed with a 2.5 M solution of n-butyl lithium (19.6 mL, 49.2 mmol) in hexane at −70° C. in argon. After stirring for 15 min at this temperature hexamethyl phosphoric triamide (19.4 g, 18.8 mL, 108 mmol) was added and the mixture stirred a further 15 min. A solution of 2-((S)-3-bromo-2-methylpropoxy)tetrahydropyrane (10.6 g, 44.7 mmol) in anhydrous tetrahydrofuran (40 mL) was added in drops to this solution and this was the slowly heated to room temperature. After adding saturated ammonium chloride solution (40 mL), the mixture was concentrated to low volume in a vacuum, the residue taken up in water (150 mL) and extracted with cyclohexane/diethyl ether (1:1.3×100 mL). The combined organic phases were dried with sodium sulphate and concentrated to low volume in a vacuum. The raw product (11 g) was purified by flash chromatography (400 g, 20×7.5 cm) with ethyl acetate/cyclohexane (1:30).

Yield: 4.58 g (35%), colourless oil
$^1$H-NMR (DMSO-d$_6$): 0.47-0.58 (m, 6H); 0.90-0.98 (m, 12H); 1.41-1.52 (m, 4H); 1.56-1.74 (m, 1H); 1.80-1.92 (m, 1H); 2.17-2.36 (m, 2H); 3.16-3.27 (m, 1H); 3.36-3.45 (m, 1H); 3.48-3.58 (m, 1H); 3.68-3.58 (m, 1H); 3.68-3.78 (m, 1H); 4.50-4.57 (m, 1H).
$^{13}$C-NMR (DMSO-d$_6$): 4.0; 7.3; 16.0; 16.1; 18.9; 19.0; 23.1; 23.2; 24.98; 25.0; 26.3; 30.1; 30.2; 32.3; 32.4; 60.9; 61.1; 70.0; 70.3; 82.2; 97.6; 98.1; 107.0; 107.1.

This is a diastereoisomer mixture.

Step 3

(R)-2-methyl-5-triethylsilanylpent-4-in-1-ol

A solution of triethyl-[(R)-4-methyl-5-(tetrahydro-2H-pyran-2-yloxy)pent-1-inyl]silane (3.84 g, 13 mmol) in tetrahydrofuran (50 mL) was mixed with 2 N hydrochloric acid (50 mL) and stirred for 6 h at 50° C. The reaction mixture was then adjusted to pH 7 with 2 N sodium hydroxide solution (50 mL), concentrated to low volume in a vacuum, and the aqueous phase obtained extracted with ethyl acetate (3×30 mL). The combined organic phases were dried with sodium sulphate and concentrated slightly to low volume in a vacuum. The raw product (3.33 g) was purified by flash chromatography (200 g, 20×5.7 cm) with ethyl acetate/cyclohexane (1:7).

Yield: 1.79 g (65%), colourless oil
$^1$H-NMR (DMSO-d$_6$): 0.53 (q, 6H, J=8.2 Hz); 0.93 (q, 9H, J=6.6 Hz); 0.95 (d, 3H, J=8.0 Hz); 1.67 (dt, 1H, J=13.3; 6.6 Hz), 2.12 (dd, 1H, J=16.9, 7.0 Hz); 2.29 (dd, 1H, J=16.9, 5.4 Hz); 3.24-3.30 (m, 2H); 4.52 (t, 1H, J=5.3 Hz).

Step 4

Triethyl-((R)-5-iodo-4-methylpent-1-inyl)silane

A solution of (R)-2-methyl-5-triethylsilanylpent-4-in-1-ol (2.18 g, 10.3 mmol) in anhydrous acetonitrile (50 mL) was added in drops to a solution of triphenylphosphine diiodide (10.6 g, 20.6 mmol) and imidazole (4.2 g, 61.8 mmol) in anhydrous acetonitrile (100 mL) in argon and stirred for 24 h at room temperature. The solvent was then concentrated to low volume in a vacuum and the residue purified by flash chromatography (100 g, 20×4.5 cm) with ethyl acetate/cyclohexane (1:9).

Yield: 2.60 g (78%), colourless oil
$^1$H-NMR (DMSO-d$_6$): 0.44-0.59 (m, 6H); 0.87-1.03 (m, 12H); 1.63-1.75 (m, 1H); 2.28-2.32 (m, 2H); 3.29-3.35 (m, 2H, superposed by HDO signal).
Rotation value: $[\alpha]_D^{24}$=−2.48° (c 1.0, MeOH).

Step 5

(R)-4-dimethylamino-1-(2-methyl-5-(triethylsilyl)pent-4-inyl)-4-phenylcyclohexanol A 1.7 M solution of tert-butyl lithium (7.8 mL, 13.3 mmol) in pentane was added in drops to a solution of triethyl-((R)-5-iodo-4-methylpent-1-inyl)silane (2.15 g, 6.6 mmol) in anhydrous diethyl ether (100 mL) at −85° C. in argon, wherein the inside temperature was held at −85° C. After stirring for 2 h at −85° C. a solution of 4-dimethylamino-4-phenylhexanone (1.43 g, 6.6 mmol) in anhydrous diethyl ether (30 mL) was added in drops at this temperature and stirred for a further 30 min. A solution of trimethylchlorosilane (1.44 g, 1.69 mL, 13.3 mmol) in diethyl ether (12 mL) was then added to the solution in drops and slowly heated to room temperature. The reaction mixture was then mixed with saturated ammonium chloride solution (20 mL) and the separated solid (2.00 g) was filtered off. The phases were separated and the aqueous [phase?] extracted with diethyl ether (3×30 mL). The combined diethyl ether phases were washed with sodium chloride solution (20 mL), dried with sodium sulphate, filtered and concentrated to low volume in a vacuum. No target product could be isolated from this phase. The separated solid (2.00 g) was then mixed with saturated sodium hydrogencarbonate solution (50 mL) and the resulting suspension extracted with ethyl acetate (3×30 mL). The combined ethyl acetate phases were dried with sodium sulphate and concentrate to low volume in a vacuum. The raw product (351 mg) was purified by flash chromatography (18 g, 20×2.0 cm) with ethyl acetate/cyclohexane (1:2).

Yield: 237 mg (9%), colourless oil $^1$H-NMR (DMSO-d$_6$): 0.54 (q, 6H, J=8.4 Hz); 0.96 (t, 9H, J=7.8 Hz); 1.03 (d, 3H, J=6.7 Hz); 1.20-1.40 (m, 3H); 1.52-1.70 (m, 3H); 1.74-1.89 (m, 3H); 1.91 (s, 6H); 2.10-2.34 (m, 4H); 3.85 (s, 1H); 7.19-7.39 (m, 5H).

This is a uniform diastereoisomer.

Step 6

(R)-4-dimethylamino-1-[2-methyl-3-(2-(triethylsilyl)-1H-indol-3-yl)propyl]-4-phenyl-cyclohexanol A solution of (R)-4-dimethylamino-1-(2-methyl-5-(triethylsilyl)pent-4-inyl)-4-phenylcyclohexanol (106 mg, 0.25 mmol), [1,3-bis-(2,6-diisopropylphenyl)imidazol-2-ylidene]-(3-chloropyridyl)palladium(II)-chloride (PEPPSI, 34 mg, 0.05 mmol), 2-iodoaniline (68 mg, 0.31 mmol) and sodium carbonate (136 mg, 1.28 mmol) in oxygen- and water-free N,N-dimethylformamide (5 mL) was stirred for 18 h at 100° C. The reaction mixture was concentrated to low volume in a vacuum, the residue mixed with toluol several times and the mixture concentrated to low volume again in each case. This residue was distributed between water and ethyl acetate (10 mL each), the phases were separated and the aqueous phase extracted with ethyl acetate (3×10 mL). The combined organic phases were washed with 1 M sodium thiosulphate solution and water (10 mL each), dried with sodium sulphate, filtered and concentrated to low volume in a vacuum. The raw product was purified by flash chromatography (10 g, 20×1.5 cm) with ethyl acetate/cyclohexane (1:2).

Yield: 89 mg (71%), yellowish oil $^1$H-NMR (CDCl$_3$): 0.87-1.13 (m, 18H); 1.48-1.57 (m, 4H); 1.73-1.95 (m, 4H); 2.00 (s, 6H); 2.03-2.10 (m, 2H); 2.11-2.40 (m, 2H); 2.69 (dd, 1H, J=14.0, 8.6 Hz); 2.92 (dd, 1H, J=14.0, 6.8 Hz); 7.06-7.40 (m, 8H); 7.70 (d, 1H, J=7.8 Hz); 7.90 (s, 1H).

$^{13}$C-NMR (CDCl$_3$): 3.9; 7.4; 22.4; 29.0; 29.1; 29.8; 33.5; 334.1; 35.9; 38.0; 48.7; 59.6; 71.8; 110.7; 118.8; 119.6; 122.0; 125.2; 126.4; 127.1; 127.4; 129.0; 131.4; 138.7.

LC-MS (method 1): m/z: [M+H]$^+$=505.4, R$_t$ 4.2 min.

Step 7

(R)-1-(3-(1H-indol-3-yl)-2-methylpropyl)-4-(dimethylamino)-4-phenylcyclohexanol A solution of (R)-4-dimethylamino-1-[2-methyl-3-(2-(triethylsilyl)-1H-indol-3-yl)propyl]-4-phenylcyclohexanol (175 mg, 0.34 mmol) in anhydrous tetrahydrofuran (30 mL) was mixed with tetra-n-butyl ammonium fluoride trihydrate (109 mg, 0.34 mmol) and stirred for 4 h with reflux. The reaction mixture was then concentrated to low volume in a vacuum and the residue was purified by flash chromatography (10 g, 20×1.5 cm) with ethyl acetate/methanol (95:5).

Yield: 115 mg (86%), colourless foam

Melting point: 56-59° C.

$^1$H-NMR (CDCl$_3$): 1.06 (d, 3H, J=6.6 Hz); 1.30-1.41 (m, 2H); 1.49 (dd, 2H, J=14.5, 7.0 Hz); 1.72-1.98 (m, 4H); 2.02 (s, 6H); 2.04 (s, 1H); 2.08-2.30 (m, 3H); 2.61 (dd, 1H, J=14.3, 7.7 Hz); 2.84 (dd, 1H, J=14.2, 6.4 Hz); 7.02 (d, 1H, J=2.2 Hz); 7.08-7.40 (m, 8H); 7.65-7.67 (m, 1H); 8.09 (s, 1H).

$^{13}$C-NMR (CDCl$_3$): 22.7; 27.2; 29.2; 29.3; 30.1; 33.6; 34.1; 34.7; 38.1; 48.1; 60.4; 71.8; 111.0; 115.6; 119.1; 119.2; 121.7; 122.3; 126.6; 127.2; 127.6; 127.9; 136.4; 137.9.

$^1$H-NMR (DMSO-d$_6$): 0.92 (d, 3H, J=6.6 Hz); 1.23-1.40 (m, 4H); 1.45-1.86 (m, 6H); 1.84 (s, 6H); 1.91 (s, 2H); 2.00-2.31 (m, 3H); 2.43 (dd, 1H, J=14.1, 8.6 Hz); 2.81 (dd, 1H, J=14.0, 5.5 Hz); 6.92-7.10 (m, 2H); 7.17-7.27 (m, 1H); 7.29-7.38 (m, 6H); 7.53 (d, 1H, J=7.7 Hz); 10.73 (s, 1H).

LC-MS (method 1): m/z: [M+H]$^+$=391.4, R$_t$ 3.3 min.

Step 8

(S)—N,N,3-trimethyl-4'-phenyl-2,3,4,9-tetrahydrospiro[carbazole-1,1'-cyclohexane]-4'-amine (Example No. 15, a diastereomer)

A solution of (R)-1-(3-(1H-indol-3-yl)-2-methylpropyl)-4-(dimethylamino)-4-phenylcyclohexanol (100 mg, 0.25 mmol) in anhydrous 1,2-dichloroethane (10 mL) was mixed with trifluoromethane sulphonic acid trimethylsilyl ester (222 mg, 181 µL, 1 mmol) and stirred for 4 h at 50° C. After adding dichloromethane (10 mL) the solution was washed with 1 M potassium carbonate solution (2×10 mL), water (10 mL) and saturated sodium chloride solution (10 mL), dried with sodium sulphate and concentrated to low volume in a vacuum. The residue (90 mg) was taken up in methanol (10 mL) and stirred for 16 h at room temperature. The precipitated solid was separated from the solution by decanting, the remaining solid once again mixed with methanol, stirred and decanted, as a result of which Example No. 15 was obtained.

Example No. 15: yield: 38 mg (41%), white solid

Melting point: 208-211° C.

$^1$H-NMR (DMSO-d$_6$): 1.07 (d, 3H, J=6.5 Hz); 1.26 (br d, 2H, J=12.0 Hz); 1.52-1.71 (m, 3H); 1.80-2.00 (m, 2H); 2.04 (s, 6H); 2.22 (d, 1H, J=13.0 Hz); 2.53-2.70 (m, 3H); 2.76 (dd, 1H, J=14.9, 4.5 Hz); 3.17 (d, 1H, J=5.2 Hz); 6.85-7.01 (m, 2H); 7.22-7.45 (m, 7H); 10.56 (s, 1H).

LC-MS: m/z: [M+H]$^+$=373.3, 3.8 min.

Studies on the Efficacy of the Compounds According to the Invention

Measurement of the ORL 1-Bond

The compounds were examined with membranes of recombinant CHO-ORL 1 cells in a receptor binding assay with $^3$H-nociceptin/orphanin FQ. This test system was conducted in accordance with the method outlined by Ardati et al. (Mol. Pharmacol., 51, 1997, pp. 816-824). The concentration of $^3$H-nociceptin/orphanin FQ amounted to 0.5 nM in these tests. The binding assays were conducted in each case on 20 μg of membrane protein per 200 μl of preparation in 50 mM of HEPES, pH 7.4, 10 nM of $MgCl_2$ and 1 mM of EDTA. The binding to the ORL 1-receptor was determined using 1 mg of WGA-SPA beads (Amersham-Pharmacia, Freiburg) in each case by incubating the preparation for one hour at RT and then conducting measurements in the Trilux scintillation counter (Wallac, Finland). The affinity is indicated as nanomolar $K_i$ value or in % inhibition at c=1 μM in Table 1.

Measurement of the μ-Bond

The affinity to the human μ-opiate receptor was determined in a homogeneous preparation in microtiter plates. For this, dilution series of the respective compound to be tested were incubated for 90 minutes at room temperature with a receptor membrane preparation (15-40 μg of protein per 250 μl of incubation batch) of CHO-K1 cells, which express the human μ-opiate receptor (RB-HOM receptor membrane preparation of NEN, Zaventem, Belgium), in the presence of 1 nmol/l of the radioactive ligand [$^3$H']-naloxone (NET719, NEN, Zaventem, Belgium) and of 1 mg WGA-SPA beads (wheat germ agglutinin SPA beads from Amersham/Pharmacia, Freiburg, Germany) in a total volume of 250 μl. 50 mmol/l of tris-HCl supplemented by 0.05% by wt. of sodium azide and 0.06% by wt. of bovine serum albumin was used as incubation buffer. 25 μmol/l of naloxone were additionally added to determine the non-specific bond. After the ninety-minute incubation time had ended, the microtiter plates were centrifuged for 20 minutes at 1000 g and the radioactivity measured in a β-counter (Microbeta-Trilux, PerkinElmer Wallac, Freiburg, Germany). The percentage displacement of the radioactive ligand from its bond to the human μ-opiate receptor was determined with a concentration of the test substances of 1 μmol/l and was specified as percentage inhibition (% inhibition) of the specific bond. In some instances, working from the percentage displacement by different concentrations of the compounds of the general formula I according to the invention, $IC_{50}$ inhibition concentrations were calculated that effect a 50 percent displacement of the radioactive ligand. Ki values for the test substances were obtained by conversion using the Cheng-Prusoff equation. In some cases, the determination of the Ki value was omitted and only the inhibition with a test concentration of 1 μM was determined.

Measurement of the Kappa-Bond

The determination occurs in a homogeneous batch in microtiter plates. For this, dilution series of the respective substances to be tested were incubated for 90 minutes at room temperature with a receptor membrane preparation (7 μg of protein per 250 μl of incubation batch) of CHO-K1 cells, which express the human p-opiate receptor, in the presence of 1 nmol/l of the radioactive ligand [$^3$H']—Cl-977 and 1 mg WGA-SPA beads (wheat germ agglutinin SPA beads from Amersham/Pharmacia, Freiburg, Germany) in a total volume of 250 μl. 50 mmol/l of tris-HCl supplemented by 0.05% by wt. of sodium azide and 0.06% by wt. of bovine serum albumin was used as incubation buffer. 100 μmol/l of naloxone were additionally added to determine the non-specific bond. After the ninety-minute incubation time had ended, the microtiter plates were centrifuged for 20 minutes at 500 rpm and the radioactivity measured in a β-counter (Microbeta-Trilux 1450, PerkinElmer Wallac, Freiburg, Germany). The percentage displacement of the radioactive ligand from its bond to the human μ-opiate receptor was determined with a concentration of the test substances of 1 μmol/l and was specified as percentage inhibition (% inhibition) of the specific bond. Working from the percentage displacement by different concentrations of the compounds to be tested, $IC_{50}$ inhibition concentrations can be calculated that effect a 50 percent displacement of the radioactive ligand. Ki values for the test substances can be calculated by conversion using the Cheng-Prusoff equation.

Analgesia Testing in the Tail Flick Test in Rats

The analgesic efficacy of the test compounds was examined in the hot beam (tail flick) test in rats using the method of D'Amour and Smith (J. Pharm. Exp. Ther. 72, 74, 79 (1941)). Female Sprague Dawley rats with a weight of between 130 and 190 g were used for this. The animals were placed individually into special test cages and the base of the tail subjected to a focussed hot beam from a lamp (tail flick type 50/08/1.bc, Labtec, Dr. Hess). The lamp intensity was adjusted so that the time from switching on the lamp to the sudden flicking away of the tail (pain latency) amounted to 2.5-5 seconds in untreated animals. Before being given a test compound, the animals were pre-tested twice within 30 minutes and the mean value of these measurements calculated as pre-test mean. The pain measurement was conducted 20, 40 and 60 min after intravenous administration. The analgesic effect was determined as increase in pain latency (% MPE) according to the following formula: $[(T_1-T_0)/(T_2-T_0)] \times 100$. In this case, $T_0$ is the latency time before and $T_1$ the latency time after substance application, $T_2$ is the maximum exposure time (12 sec). To determine the dose dependency, the respective test compound was applied in 3-5 logarithmically increasing doses, which respectively include the threshold dose and maximum effective dose, and the $ED_{50}$ values determined by means of regression analysis. The $ED_{50}$ calculation occurred in the effect maximum, 20 minutes after intravenous substance application.

Chung Model: Mononeuropathic Pain after Spinal Nerve Ligature

Animals: Male Sprague Dawley rats (140-160 g) from a commercial breeder (Janvier, Genest St. Isle, France) were held under a 12:12 h light-dark rhythm. The animals were kept with a free choice of feed and tap water. A break of one week was adhered to between delivery of the animals and the operation. The animals were tested multiple times after operation over a period of 4-5 weeks, in which case a wash out time of at least one week was adhered to.

Model description: Under pentobarbital narcosis (Narcoren®, 60 mg/kg i.p., Merial GmbH, Hallbergmoos, Germany), the left L5, L6 spinal nerves were exposed by removing a piece of paravertebral muscle and a portion of the left spinal process of the L5 lumbar vertebral body. The spinal nerves L5 and L6 were carefully isolated and bound with a firm ligature (NC silk black, USP 5/0, metric 1, Braun Melsungen A G, Melsungen, Germany) (Kim and Chung 1992). After ligature the muscle and adjacent tissue were sutured and the wound closed by metal clamps.

After a one-week recovery time the animals are placed in cages with a wire base for measurement of the mechanical allodynia. The pull-away threshold was determined at the ipsi- and/or contralateral rear paw by means of an electronic von Frey filament (Somedic A B, Malmö, Sweden). The median of five stimulations gave a data point. The animals were tested 30 min before application and at various times after application of test substance or vehicle solution. The data were determined as % maximum possible effect (% MPE) from the pre-testing of individual animals (=0% MPE) and the test values of an independent sham control group (=100% MPE). Alternatively the pull-away thresholds were shown in gram.

Statistical evaluation: $ED_{50}$ values and 95% confidence intervals were determined by means of semi-logarithmic regression analysis at the time of maximum effect. The data were analysed by means of a variance analysis with repeated measurements as well as a Bonferroni post hoc analysis procedure. The group size usually amounted to n=10.

REFERENCES

Kim, S. H. and Chung, J. M.: An experimental model for peripheral neuropathy produced by segmental spinal nerve ligature in the rat, Pain, 50 (1992) 355-363.

hERK-K+ Channel Binding Assay

In the hERK binding assay the displacement of [$^3$H] dofetilide by test substances on cell membranes (isolated from hERK-transfected human embryonic kidney cells, HE 293) was tested. Non-specific bonds are determined in the presence of dofetilide. The incubation time amounts to 60 min at 37° C. After the incubation time has elapsed, the test plate is aspirated above a filter plate. Receptor molecules bonded by [$^3$H] dofetilide and remaining in the filter can now be quantified accordingly by the measurement of radioactivity, from which findings concerning the displacement of [$^3$H] dofetilide by test substances are given. Further details can be read in the method part of Finlayson et al. (2001).

Literature: [$^3$H] dofetilide binding in SHSY5Y and HEK293 cells expressing a HERG-like K+ channel? Finlayson K, Pennington A J, Kelly J S. Eur J. Pharmacol. 2001 Feb. 2; 412(3):203-12.

Results

| No. | % Inhibition (ORL1) [1 µM] | Ki (ORL1) Mean [µM] | % Inhibition (µ) [1 µM] | Ki (µ) Mean [µM] | Tail flick Rat, i.v. | SNL Rat, i.v. |
|---|---|---|---|---|---|---|
| Ex. 1 | 33 | 0.240 | 62 | 0.460 | nd | nd |
| Ex. 2 | 99 | 0.001 | 98 | 0.002 | 100% MPE at 100 µg/kg | 19% MPE at 5 µg/kg |
| Ex. 3 | nd | 0.53 | nd | 0.27 | nd | nd |
| Ex. 4 | 82 | 0.016 | 100 | 0.011 | nd | nd |
| Ex. 5 | 40 | nd | 67 | nd | nd | nd |
| Ex. 6 | 96 | 0.011 | 96 | 0.007 | nd | nd |
| Ex. 7 | 18 | 0.63 | 57 | 0.28 | nd | nd |
| Ex. 8 | 100 | 0.002 | 97 | 0.002 | nd | nd |
| Ex. 11 | 74 | nd | 91 | nd | nd | nd |
| Ex. 12 | 96 | nd | 98 | nd | nd | nd |
| Ex. 15 | 96 | nd | 97 | nd | nd | nd | nd = not determined

The properties of the compounds according to the invention of Examples 1 and 2 and the properties of the corresponding compounds, which have the same parent substance and only differ in the residue —$CR_{18}R_{19}$—(≡X), are compared in the following table:

| No. | X | Diastereomer | Ki (kappa)/ Ki (ORL1) | Ki (ORL1) Mean [µM] | Ki (kappa) Mean [µM] | Ki (hERG) Mean [µM] |
|---|---|---|---|---|---|---|
| Ex. 1 | —$CH_2$— | polar | 4 | 0.240 | 1.02 | 13% (1 µM) |
| C-1 | —NH— | polar | 1 | 0.006 | 0.007 | 19% (1 µM) |
| Ex. 2 | —$CH_2$— | non-polar | 11 | 0.001 | 0.011 | n.e. |
| C-2 | —NH— | non-polar | 2.5 | 0.0002 | 0.0005 | 0.49 |

As the above comparison shows, the compounds according to the invention have a higher selectivity with respect to the kappa-opioid receptor (defined as $1/[K_{i(ORL1)}/K_{i(kappa)}]$) compared to the structurally similar spiro amines (X═—NH—).

It can therefore be assumed that with the administration of the compounds according to the invention those side-effects, which are usually associated with a binding of the kappa-opioid receptor (e.g. dysphoria, sedation and diuresis), occur only on a small scale if at all.

Moreover, the above comparison shows that the compounds according to the invention, in particular the respective more non-polar diastereomer, has a lower affinity to the hERG ion channel compared to the structurally similar spiro amines (X═—NH—).-

Therefore, it can be additionally assumed that with administration of the compounds according to the invention those side-effects, which are usually associated with a binding of the hERG ion channel (e.g. cardiovascular side-effects), occur only on a small scale if at all.

The invention claimed is:

1. A compound of the formula (1):

(1)

[Chemical structure of formula (1)]

wherein
$A_1$ stands for —$CR_7$=,
$A_2$ stands for —$CR_8$=,
$A_3$ stands for —$CR_9$=,
$A_4$ stands for —$CR_{10}$=;
$Y_1, Y_1', Y_2, Y_2', Y_3, Y_3', Y_4$ and $Y_4'$ are selected respectively independently of one another from the group consisting of —H, —F, —Cl, —Br, —$R_0$, —SH, —$SR_0$, —S($=$O)$_{1-2}$—$R_0$, —$NH_2$, —$NHR_0$, and —N($R_0$)$_2$;
W stands for —$NR_4$—;
$R_0$ respectively independently stands for —$C_{1-8}$-aliphatic, -aryl, or —$C_{1-8}$-aliphatic-aryl;
$R_1$ and $R_2$, independently of one another, stand for —H or —$R_0$; or $R_1$ and $R_2$ together stand for —$CH_2CH_2OCH_2CH_2$—, —$CH_2CH_2NR_{11}CH_2CH_2$— or —($CH_2$)$_{3-6}$—;
$R_3$ stands for —$R_0$ or 2-thienyl;
$R_4$ stands for —H or —$R_0$;
$R_5, R_5', R_6, R_6', R_7, R_8, R_9, R_{10}, R_{18}$ and $R_{19}$ respectively independently of one another stand for —H, —F, —Cl, —Br, —$SR_{13}$, —S($=$O)$_2R_{13}$, —C($=$O)$OR_{13}$, —C($=$O)$NR_{13}$, —C($=$O)$NR_0OR_0$, —$NR_{14}R_{15}$, —NHC($=$O)$R_0$, $CH_2OH$ or —$R_0$;
$R_{13}$ respectively independently stands for —H or —$R_0$;
$R_{14}$ and $R_{15}$ independently of one another stand for —H or —$R_0$;
wherein
"aliphatic" respectively is a branched or unbranched, saturated or a mono- or polyunsaturated, unsubstituted or mono- or polysubstituted, aliphatic hydrocarbon residue;
wherein with respect to "aliphatic", "mono- or polysubstituted" means the mono- or polysubstitution of one or more hydrogen atoms by —F, —Cl, —Br, or —$R_0$;
"aryl", respectively independently, stands for a carbocyclic ring system with at least one aromatic ring, but without heteroatoms in this ring, wherein, if necessary, the aryl residues can be condensed with further saturated, (partially) unsaturated or aromatic ring systems, and each aryl residue can be present in unsubstituted or mono- or polysubstituted form, wherein the aryl substituents can be the same or different and in any desired and possible position of the aryl and are selected from the group consisting of —F, —Cl, —Br, and —$R_0$;

said compound being in the form of a single stereoisomer or mixture thereof, the free compound and/or a physiologically compatible salt thereof.

2. Compound according to claim 1, which has the formula (2):

(2)

[Chemical structure of formula (2)]

3. Compound according to claim 2, which has the formula (2.1), (2.2), (2.3) or (2.4):

(2.1)

[Chemical structure of formula (2.1)]

(2.2)

[Chemical structure of formula (2.2)]

(2.3)

[Chemical structure of formula (2.3)]

(2.4)
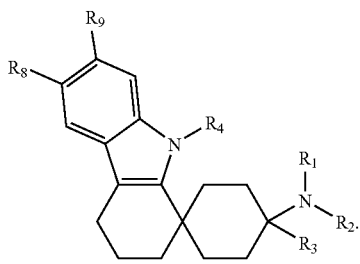

4. Compound according to claim 2, which has the formula (2.5), (2.6), (2.7) or (2.8):

(2.5)
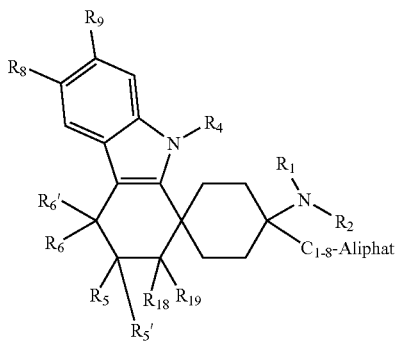

(2.6)
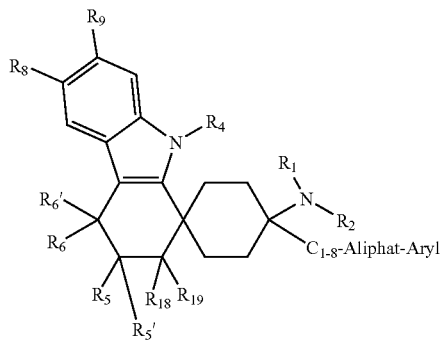

(2.7)
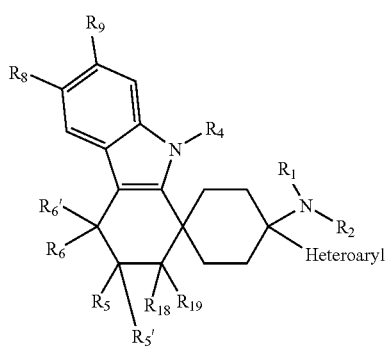

(2.8)
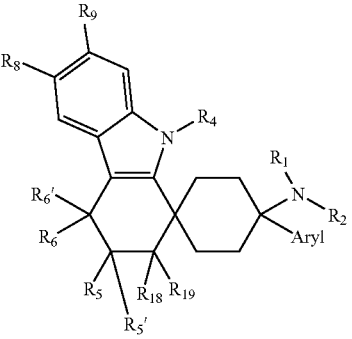

wherein
Aliphat=aliphatic; and
Heteroaryl=2-thienyl.

5. Compound according to claim 1, which has the formula (6):

(6)
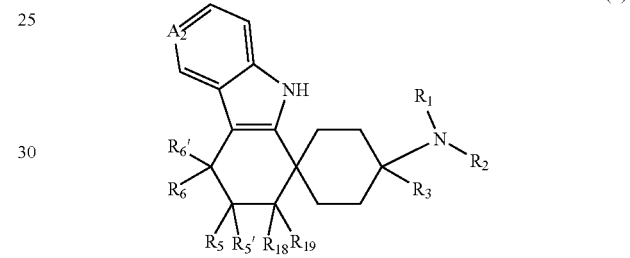

wherein
$A_2$ stands for —$CR_8$=,
$R_1$ stands for —$CH_3$;
$R_2$ stands for —H or —$CH_3$;
or $R_1$ and $R_2$ together stand for —$(CH_2)_{3-4}$—;
$R_3$ stands for —$C_{1-6}$-aliphatic, -aryl, 2-thienyl, or —$C_{1-6}$-aliphatic-aryl;
$R_5$, $R_5'$, $R_6$, $R_6'$, $R_8$, $R_{18}$ and $R_{19}$ respectively independently of one another stand for —H, —F, —Cl, —Br, —$SR_{13}$, —S(=O)$_2R_{13}$, —$NR_{14}R_{15}$ or —$R_0$;
$R_{13}$ respectively independently stands for —H or —$R_0$; and
$R_{14}$ and $R_{15}$ independently of one another stand for —H or —$R_0$.

6. Compound according to claim 1, which is selected from the group consisting of: N,N,3,3-tetramethyl-4'-phenyl-2,3,4,9-tetrahydrospiro[carbazole-1,1'-cyclohexane]-4'-amine; N,N-dimethyl-3,4'-diphenyl-2,3,4,9-tetrahydro-spiro[carbazole-1,1'-cyclohexane]-4'-amine; 4'-(3-fluorophenyl)-N,N-dimethyl-3-phenyl-2,3,4,9-tetrahydrospiro[carbazole-1,1'-cyclohexane]-4'-amine; N,N,4,4-tetramethyl-4'-phenyl-2,3,4,9-tetrahydrospiro[carbazole-1,1'-cyclohexane]-4'-amine; N,N-dimethyl-4'-phenyl-2-(phenylsulphonyl)-2,3,4,9-tetrahydrospiro[carbazole-1,1'-cyclohexane]-4'-amine; 4'-(dimethylamino)-N-methoxy-N-methyl-4'-phenyl-2,3,4,9-tetrahydrospiro-[carbazole-1,1'-cyclohexane]-2-carboxamide; (4'-(dimethylamino)-4'-phenyl-2,3,4,9-tetrahydrospiro[carbazole-1,1'-cyclohexane]-2-yl)methanol; N4',N4'-dimethyl-4'-(3-fluorophenyl)-2,3,4,9-tetrahydrospiro[carbazole-1,1'-cyclohexane]-3,4'-diamine; N-(4'-(dimethylamino)-4'-(3-fluorophenyl)-2,3,4,9-tetrahydrospiro[carbazole-1,1'-cyclohexane]-3-yl)cinnamamide;

N-(4'-(dimethylamino)-4'-(3-fluorophenyl)-2,3,4,9-tetrahydrospiro[carbazole-1,1'-cyclohexane]-3-yl)-2-phenylacetamide; N-(4'-(dimethylamino)-4'-(3-fluorophenyl)-2,3,4,9-tetrahydrospiro[carbazole-1,1'-cyclohexane]-3-yl)-3-phenylpropanamide; N-(4'-(dimethylamino)-4'-(3-fluorophenyl)-2,3,4,9-tetrahydrospiro[carbazole-1,1'-cyclohexane]-3-yl)-2-phenylcyclopropane carboxamide; N-(4'-(dimethylamino)-4'-(3-fluorophenyl)-2,3,4,9-tetrahydrospiro-[carbazole-1,1'-cyclohexane]-3-yl)acetamide; 4'-butyl-N,N-dimethyl-2,3,4,9-tetrahydrospiro[carbazole-1,1'-cyclohexane]-4'-amine; 4'-benzyl-N,N-dimethyl-2,3,4,9-tetrahydrospiro[carbazole-1,1'-cyclohexane]-4'-amine; N,N-dimethyl-4'-(thiophen-2-yl)-2,3,4,9-tetrahydrospiro[carbazole-1,1'-cyclohexane]-4'-amine; 4'-(3-fluorophenyl)-N,N-dimethyl-2,3,4,9-tetrahydrospiro[carbazole-1,1'-cyclohexane]-4'-amine; 4'-(azetidin-1-yl)-4'-phenyl-2,3,4,9-tetrahydrospiro[carbazole-1,1'-cyclohexane]; 4'-(azetidin-1-yl)-4'-(3fluorophenyl)-2,3,4,9-tetrahydrospiro[carbazole-1,1'-cyclohexane]; 4'-(azetidin-1-yl)-4'-phenyl-2,3,4,9-tetrahydrospiro[carbazole-1,1'-cyclohexane]; N,N-dimethyl-N-(4-butyl-2',3',4',9'-tetrahydro-1H-spiro[cyclohexane-1,1'-carbazole]-4-yl)amine; 4'-benzyl-N,N-dimethyl-2,3,4,9-tetrahydrospiro[carbazole-1,1'-cyclohexane]-4'-amine; 4'-(3-fluorophenyl)-N,N-dimethyl-2,3,4,9-tetrahydrospiro[carbazole-1,1'-cyclohexane]-4'-amine; N,N-dimethyl-4'-(thiophen-2-yl)-2,3,4,9-tetrahydrospiro[carbazole-1,1'-cyclohexane]-4'-amine; and (S)—N,N,3-trimethyl-4'-phenyl-2,3,4,9-tetrahydrospiro[carbazole-1,1'-cyclohexane]-4'-amine, said compound being in the form of a single stereoisomer or mixture thereof, the free compound and/or a physiologically compatible salt thereof.

7. A pharmaceutical composition comprising at least one compound according to claim 1, said compound being in the form of a single stereoisomer or mixture thereof, the free compound and/or a physiologically compatible salt thereof, and optionally suitable additives and/or adjuvants and/or further active substances.

* * * * *